United States Patent
Landry et al.

(10) Patent No.: US 9,526,786 B2
(45) Date of Patent: Dec. 27, 2016

(54) THERMOSTABILIZATION OF PROTEINS

(71) Applicants: Donald W. Landry, New York, NY (US); James H. Woods, Ann Arbor, MI (US); Roger K. Sunahara, Ann Arbor, MI (US); Diwahar L. Narasimhan, Ann Arbor, MI (US); Joanne MacDonald, New York, NY (US); Milan N. Stojanovic, Fort Lee, NJ (US); John J. Tesmer, Ann Arbor, MI (US); Remy L. Brim, Farmington Hills, MI (US)

(72) Inventors: Donald W. Landry, New York, NY (US); James H. Woods, Ann Arbor, MI (US); Roger K. Sunahara, Ann Arbor, MI (US); Diwahar L. Narasimhan, Ann Arbor, MI (US); Joanne MacDonald, New York, NY (US); Milan N. Stojanovic, Fort Lee, NJ (US); John J. Tesmer, Ann Arbor, MI (US); Remy L. Brim, Farmington Hills, MI (US)

(73) Assignees: The Trustee of Columbia University in the City of New York, New York, NY (US); The Regents of the University of Michigan, Ann Arbor, MI (US)

( * ) Notice: Subject to any disclaimer, the term of this patent is extended or adjusted under 35 U.S.C. 154(b) by 248 days.

(21) Appl. No.: 14/166,619

(22) Filed: Jan. 28, 2014

(65) Prior Publication Data
US 2014/0348813 A1 Nov. 27, 2014

Related U.S. Application Data

(63) Continuation of application No. 12/667,895, filed as application No. PCT/US2008/069659 on Jul. 10, 2008, now Pat. No. 8,637,009.

(60) Provisional application No. 60/948,976, filed on Jul. 10, 2007, provisional application No. 60/987,661, filed on Nov. 13, 2007.

(51) Int. Cl.
| | |
|---|---|
| A61K 47/22 | (2006.01) |
| C12N 9/18 | (2006.01) |
| C12N 9/16 | (2006.01) |
| A61K 31/505 | (2006.01) |
| A61K 45/06 | (2006.01) |
| A61K 38/46 | (2006.01) |
| A61K 47/12 | (2006.01) |
| A61K 47/18 | (2006.01) |
| C12Q 1/44 | (2006.01) |

(52) U.S. Cl.
CPC .......... *A61K 47/22* (2013.01); *A61K 31/505* (2013.01); *A61K 38/465* (2013.01); *A61K 45/06* (2013.01); *A61K 47/12* (2013.01); *A61K 47/18* (2013.01); *C12N 9/18* (2013.01); *C12Q 1/44* (2013.01); *C12Y 301/01084* (2013.01); *G01N 2333/918* (2013.01)

(58) Field of Classification Search
CPC .................. C12Y 301/01084; C12Y 101/00; C12N 9/18; A61K 38/465
USPC .................. 424/94.6; 435/188, 196, 197, 19
See application file for complete search history.

(56) References Cited

U.S. PATENT DOCUMENTS

| | | | |
|---|---|---|---|
| 5,462,868 | A | 10/1995 | Britt et al. |
| 5,730,985 | A | 3/1998 | Barber et al. |
| 5,977,314 | A | 11/1999 | Landry et al. |
| 8,318,156 | B2 | 11/2012 | Landry et al. |
| 8,637,009 | B2 * | 1/2014 | Landry et al. ............. 424/94.6 |
| 2002/0048271 | A1 | 4/2002 | Rastinejad et al. |
| 2010/0034799 | A1 | 2/2010 | Landry et al. |
| 2011/0142816 | A1 | 6/2011 | Landry et al. |

FOREIGN PATENT DOCUMENTS

| | | |
|---|---|---|
| GB | 2257972 | 1/1993 |
| WO | WO 2008/008358 | 1/2008 |

OTHER PUBLICATIONS

Ascenzi et al., The *Rhodococcus* sp. Cocaine Esterase: A Bacterial Candidate for Novel Pharmacokinetic-based Therapies for Cocaine Abuse, IUBMB Life, Jul. 2003, pp. 397-402, vol. 55, No. 7.
Australian Office Action dated Mar. 20, 2012 in related Application No. 2007272955, 5 pages.
Australian Office Action dated Nov. 1, 2012 in related Application No. 2008275025, 7 pages.
Baird et al., Natural and Artificial Enzymes Against Cocaine. I. Monoclonal Antibody 15A10 and the Reinforcing Effects of Cocaine in Rats, J. Pharmacol. Exp. Ther., 2000, pp. 1127-1134, vol. 295, No. 3.
Bresler et al., Gene Cloning and Nucleotide Sequencing and Properties of a Cocaine Esterase from *Rhodococcus* sp. Strain MBI, Appl., Environ. Microbiol., Mar. 2000, pp. 904-908, vol. 66, No. 3.

(Continued)

*Primary Examiner* — Younus Meah
(74) *Attorney, Agent, or Firm* — Dentons US LLP

(57) ABSTRACT

Provided are compositions comprising a cocaine esterase (CocE) and a compound that thermostabilizes the CocE. Also provided are methods of thermostabilizing a cocaine esterase. Additionally provided are methods of treating a mammal undergoing a cocaine-induced condition. Methods of determining whether a compound is a thermostabilizing agent for a protein are also provided. Uses of the above-described compositions for the treatment of a cocaine-induced condition is additionally provided. Additionally provided is an isolated nucleic acid encoding a CocE polypeptide having the substitutions L169K and G173Q, and the CocE polypeptide encoded by that nucleic acid, and pharmaceutical compositions thereof. Further provided is the use of that composition for the manufacture of a medicament for the treatment of a cocaine-induced condition and for the treatment of a cocaine-induced condition.

17 Claims, 37 Drawing Sheets

(56) References Cited

OTHER PUBLICATIONS

Britt et al., Identification of a Cocaine Esterase in a Strain of Pseudomonas maltophilia, Journal of Bacteriology, 1992, pp. 2087-2094, vol. 174, No. 7.
Broun et al., Catalytic plasticity of fatty acid modification enzymes underlying chemical diversity of plant lipids, Science, 1998, pp. 1315-1317, vol. 282.
Browne et al., The Influence of Plasma Butyrylcholinesterase Concentration on the In Vitro Hydrolysis of Cocaine in Human Plasma, Biopharm. Drug Dispos., 1998, pp. 309-314, vol. 19.
Canada Office Action issued Dec. 23, 2013 in related Canadian Application No. CA 2,657,246, 3 pages.
Canada Office Action issued Oct. 9, 2014 in related Canadian Application No. CA 2,691,842, 3 pages.
Carmona et al., Attenuation of Cocaine-Induced Locomotor Activity by Butyrylcholinesterase, Exp. Clin. Psychopharmacol., 1998, pp. 274-279, vol. 6, No. 3.
Carmona et al., Butyrylcholinesterase Accelerates Cocaine Metabolism: In Vitro and In Vivo Effects in Nonhuman Primates and Humans, Drug Metab. Dispos., 2000, pp. 367-371, vol. 28, No. 3.
Carmona et al., Plasma Butyrylcholinesterase Activity and Cocaine Half-life Differ Significantly in Rhesus and Squirrel Monkeys, Life Sci., 1996, pp. 939-943, vol. 59, No. 11.
Carroll et al., Pharmacotherapies for Treatment of Cocaine Abuse: Preclinical Aspects, J. Med. Chem., Jul. 29, 1999, pp. 2721-2736, vol. 42, No. 15.
Chica et al., Semi-rational approaches to engineering enzyme activity: combining the benefits of directed evolution and rational design, Curr. Opi. Biotechnol., 2005, pp. 378-384, vol. 16.
Chinese Office Action dated Jun. 1, 2011 in related Application No. 200780033496, includes English translation, 10 pages.
Chinese Office Action dated Jun. 26, 2012 in related Application No. 200780033496, in English, 4 pages.
Colombian Office Action dated Dec. 25, 2012 in related Application No. 10002.809, includes English translation, 14 pages.
Colombian Office Action dated Aug. 14, 2012 in related Application No. 09 010.531, includes English translation, 8 pages.
Cooper et al. Rapid and Robust Protection Against Cocaine-Induced Lethality in Rats by the Bacterial Cocaine Esterase, Mol. Pharmacol., 2006 pp. 1885-1891, vol. 70, No. 6.
Cooper et al., Cocaine Esterase Blocks Cocaine-Induced Seizures and Cardiovascular Effects in the Rat, FASEB Journal, 2005, p. A512, abstract No. 311.7, 1 page.
Cooper et al., Inhibition of cocaine toxicity by cocaine esterase in the rat, FASEB Journal, 2005, p. A512, abstract No. 311.6, 1 pages.
Deng et al., Anticocaine Catalytic Antibodies, J. Immunol. Methods, 2002, pp. 299-310, vol. 269.
Devos et al., Practical limits of function prediction, Proteins: Structure, Function, and Genetics, 2000, pp. 98-107, vol. 41.
Duysen et al., Wild-type and A328W Mutant Human Butyrylcholinesterase Tetramers Expressed in Chinese Hamster Ovary Cells have a 16-Hour Half-Life in the Circulation and Protect Mice from Cocaine Toxicity, J. Pharmacol. Exp. Ther., 2002, pp. 751-758, vol. 302, No. 2.
European Office Action issued Sep. 26, 2013 in related Application No. EP 07810316.5, 6 pages.
European Office Action issued Feb. 6, 2013 in related Application No. EP 08781619.5, 4 pages.
European Supplementary Search Report and Search Opinion issued Jan. 13, 2010 in related European Application No. EP 07810316 (8 pages).
European Supplementary Search Report issued Sep. 1, 2011 in related European Application No. EP 08781619.5 (10 pages).
Flores et al., Increasing the Thermal Stability of an Oligomeric Protein, Beta-Glucuronidase, Journal of Molecular Biology, 2002, pp. 325-337, vol. 315.

Gao et al., An engineered cocaine hydrolase blunts and reverses cardiovascular responses to cocaine in rats, J. Pharmacol. Exp. Ther., 2004, pp. 1046-1052, vol. 310, No. 3.
Gao et al., Gene Transfer of Cocaine Hydrolase Suppresses Cardiovascular Responses to Cocaine in Rats, Molecular Pharmacology, 2005, pp. 204-211, vol. 67, No. 1.
Gorelick, Enhancing Cocaine Metabolism with Butyrylcholinesterase as a Treatment Strategy, Drug Alcohol Depend., 1997, pp. 159-165, vol. 48.
Harris et al., Effect of Pegylation on Pharmaceuticals, Nature Reviews, Drug Discovery, Mar. 2003, pp. 214-221, vol. 2.
Harris et al., Pegylation: A Novel Process for Modifying Pharmacokinetics, Clinical Pharmacokinetics, 2001, pp. 539-551, vol. 40, No. 7.
Hoffman et al., Administration of Purified Human Plasma Cholinesterase Protects against Cocaine Toxicity in Mice, J. Toxicol. Clin. Toxicol., May 1996, pp. 259-266, vol. 34, No. 3.
International Search Report and Written Opinion dated Feb. 9, 2009 in corresponding PCT Application No. PCT/US/2008/069659 filed Jul. 10, 2008, 12 pages.
International Search Report and Written Opinion dated Sep. 29, 2008 in related PCT Application No. PCT/US07/15762 filed Jul. 10, 2007, 6 pages.
Israel Official Action dated Oct. 4, 2011 in related Application No. 196411 in English, 2 pages.
Israel Official Action dated Jan. 16, 2013 in related Application No. 196411 in English, 1 page.
Israel Official Action dated Feb. 14, 2012 in related Application No. 202917 filed Jul. 10, 2008, 2 pages.
Kim et al., Directed Evolution of Thermus Maltogenic Amylase Toward Enhanced Thermal Resistance, Applied and Environmental Microbiology, Aug. 2003, pp. 4866-4874, vol. 69. No. 8.
Ko et al., Cocaine Esterase: Interactions with Cocaine and Immune Responses in Mice, J. Pharmacol. Exp. Ther., 2007, pp. 926-933, vol. 320, No. 2.
Koetzner et al., Characterization of Butyrylcholinesterase Antagonism of Cocaine-Induced Hyperactivity, Drug Metab. Dispos., 2002, pp. 716-723, vol. 30, No. 6.
Korkegian et al., Computational Thermostabilization of an Enzyme, Science, May 6, 2005, pp. 857-860, vol. 308 No. 5723.
Landry et al., Antibody-Catalyzed Degradation of Cocaine, Science, Mar. 26, 1993, pp. 1899-1901, vol. 259.
Larsen et al., Crystal structure of a bacterial cocaine esterase, Nature Structural Biology, 2002, pp. 17-21, vol. 9, No. 1.
Larsen et al., Crystallographic and Biochemical Analysis of Cocaine-Degrading Antibody 15A10, Biochemistry, 2004, pp. 8067-8076, vol. 43.
Lehmann and Wyss, Engineering Proteins for Thermostability. The Use of Sequence Alignments Versus Rational Design ad Directed Evolution, Current Opinion in Biotechnology, 2001, pp. 371-375, vol. 12.
Lejeune et al., Quantitative analysis of the stabilization by substrate of Staphylococcus aureus PC1 β-lactamase, Chem Biol, 2001, pp. 831-842, vol. 8.
Lopez-Camacho et al., Amino Acid Substitutions Enhancing Thermostability of Bacillus Polymyxa Beta-GlucosidaseA, Biochemistry Journal, 1996, pp. 833-838, vol. 314.
Lynch et al., Cocaine Detoxification by Human Plasma Butyrylcholinesterase, Toxicol. Appl. Pharmacol., 1997, pp. 363-371, vol. 145.
Malaysian Official Action and Search Report dated Feb. 15, 2012 in related Application No. PI 20090140 filed Jul. 10, 2007, 3 pages.
Marshall et al, Rational Design and Engineering of Therapeutic Proteins, Drug Discovery Today, 2003, pp. 212-221, vol. 8, No. 5.
Mattes et al., Therapeutic Use of Butyrylcholinesterase for Cocaine Intoxication, Toxicol. Appl. Pharmacol., 1997, pp. 372-380, vol. 145.
Mets et al., A Catalytic Antibody Against Cocaine Prevents Cocaine's Reinforcing and Toxic Effects in Rats, Proc. Natl. Acad. Sci., Aug. 1998, pp. 10176-10181, vol. 95.
Miyazaki et al., Directed Evolution Study of Temperature Adaptation in a Psychrophilic Enzyme, Journal of molecular Biology, 2000, pp. 1015-1026, vol. 297.

(56) References Cited

OTHER PUBLICATIONS

New Zealand Official Action dated Jun. 14, 2010 in related Application No. 574376 filed Jul. 10, 2007, 3 pages.
New Zealand Official Action dated May 31, 2010 in related Application No. 582626 filed Jul. 10, 2008, 2 pages.
New Zealand Official Action dated Nov. 15, 2010 in related Application No. 582626 filed Jul. 10, 2008, 2 pages.
New Zealand Official Action dated Jan. 11, 2012 in related Application No. 597462 filed Jan. 5, 2012, 3 pages.
New Zealand Examination Report dated Mar. 11, 2014 in related Application 621859 filed Feb. 27, 2014, 2 pages.
New Zealand Examination Report dated Nov. 28, 2011 in related Application 574376 filed Jul. 10, 2007, 2 pages.
New Zealand Examination Report dated Jul. 11, 2013 in related Application 612929 filed Jul. 10, 2007, 3 pages.
Norman et al., A Chimeric Human/Murine Anticocaine Monoclonal Antibody Inhibits the Distribution of Cocaine to the Brain in Mice, J. Pharmacol. Exp. Ther., 2007, pp. 145-153, vol. 320, No. 1.
Pan et al, Computational Redesign of Human Butyrylcholinesterase for Anticocaine Medication, Proc. Natl. Acad. Sci., Nov. 15, 2005, pp. 16656-16661, vol. 102, No. 46.
Pancook et al., Application of Directed Evolution Technology to Optimize the Cocaine Hydrolase Activity of Human Butyrylcholinesterase, FASEB Journal, 2003, p. A565, abstract No. 364.9.
Rogers et al., Towards Cocaine Esterase Therapeutics, J. Am. Chem. Soc., Jul. 20, 2005, pp. 10016-10017, vol. 127, No. 28.
Scandurra et al., Protein Thermostability in Extremophiles, Biochimie, 1998, pp. 993-941, vol. 80.
Score Sequence Search Report cited by the Examiner on Dec. 20, 2014 in related U.S. Appl. No. 12/987,654, 14 pages.
Seffernick et al., Melamine Deaminase and Atrazine Chlorohydrolase: 98 percent Identical but Functionally Different, J. Bacteriol., Apr. 2001, pp. 2405-2410, vol. 183, No. 8.
Sen et al., Developments in Directed Evolution for Improving Enzyme Functions, Appl. Biochem. Biotechnol., 2007, pp. 212-223, vol. 143.
South Korean Office Action issued Mar. 20, 2014 in related South Korean Application No. 10-2009-7002743, in Korean, 7 pages.
South Korean Office Action issued Mar. 20, 2014 in related South Korean Application No. 10-2009-7002743, in English, 11 pages.
South Korean Office Action issued Mar. 20, 2014 in related South Korean Application No. 10-2009-7002743, in Korean, 3 pages.
South Korean Office Action issued Mar. 20, 2014 in related South Korean Application No. 10-2009-7002743, in English, 6 pages.
Srinivasan et al., Substrate-Induced Stability of Glyceraldehyde 3-Phospate Dehydrogenase from Mung Beans (*Vigna radiata* L.), Plant Physiol, 1992, pp. 2109-2112, vol. 100.
Sun et al., Cocaine Metabolism Accelerated by a Re-Engineered Human Butyrylcholinesterase, J. Pharmacol. Exp. Ther., 2002, pp. 710-716, vol. 302, No. 2.
Sun et al., Re-Engineering Butyrylcholinesterase as a Cocaine Hydrolase, Molecular Pharmacology, 2002, pp. 220-224, vol. 62, No. 2.
Turner et al, Biochemical Characterization and Structural Analysis of a Highly Proficient Cocaine Esterase, Biochemistry, 2002, pp. 12297-12307, vol. 41, No. 41.
Uchiyama et al., Directed Evolution to Improve the Thermostability of Prolyl Endopeptidase, Journal of Biochemistry, 2000, pp. 441-447, vol. 128.
US Office Action dated Nov. 28, 2011 in related U.S. Appl. No. 12/373,510, filed Oct. 2, 2009, 22 pages.
Veronese et al., Introduction and Overview of Peptide and Protein Pegylation, Advanced Drug Delivery Reviews, 2002, pp. 453-456, vol. 54.
Whisstock et al., Prediction of protein function from protein sequence, Q. Rev. Biophysics, 2003, pp. 307-340, vol. 26, No. 3.
White et al., Improved Thermostability of the North American Firefly Luciferase: Saturation Mutagenesis at Position 354, Biochemistry Journal, 1996, pp. 343-350, vol. 319.
Wishart et al., A Single Mutation Converts a Novel Phosphotyrosine Binding Domain into a Dual-Specificity Phosphatase, J. Biol. Chem., 1995, pp. 26782-26785, vol. 270, No. 45.
Witowski et al., Conversion of beta-ketoacyl Synthase to a Malonyl Decarboxylase by Replacement of the Active Cysteine with Glutamine, Biochemistry, 1999, pp. 11643-11650, vol. 38.
Xie et al., An Improved Cocaine Hydrolase: The A328Y Mutant of Human Butyrylcholinesterase is 4-Fold More Efficient, Mol. Pharmacol., 1999, pp. 83-91, vol. 55.
Zhan et al., Fundamental Reaction Mechanism for Cocaine Hydrolysis in Human Butyrylcholinesterase, Journal of the American Chemical Society, 2003, pp. 2462-2474, vol. 125.

* cited by examiner

THERMOSTABILIZATION OF PROTEINS

CROSS-REFERENCE TO RELATED APPLICATIONS

The present application is a Continuation of U.S. National Phase application Ser. No. 12/667,895 filed 10 Jul. 2008 now U.S. Pat. No. 8,637,009 issued 28 Jan. 2014; which claims the benefit of priority to International Application No. PCT/US08/69659 filed 10 Jul. 2008; which claims the benefit of U.S. Provisional Application Ser. No. 60/948,976 filed 10 Jul. 2007 and U.S. Provisional Application Ser. No. 60/987,661 filed 13 Nov. 2007; each of which is incorporated herein by reference in its entirety.

STATEMENT REGARDING FEDERALLY SPONSORED RESEARCH OR DEVELOPMENT

This invention was made with government support under Grant DA021416 awarded by The National Institutes of Health, and Grant IIS-0324845 awarded by the National Science Foundation. The Government has certain rights in the invention.

FIELD

The present application generally relates to anti-cocaine therapeutics.

BACKGROUND

Abuse of cocaine is an intractable social and medical problem that is resistant to remediation through pharmacotherapy. Cocaine acts to block the reuptake of monoamines, dopamine, norepinephrine, and serotonin thus prolonging and magnifying the effects of these neurotransmitters in the central nervous system (Benowitz, 1993). Cocaine toxicity is marked by both convulsions and cardiac dysfunction (e.g., myocardial infarction, cardiac arrhythmias, increased blood pressure, stroke, or dissecting aneurysm, and increased myocardial oxygen demand), due to effects on neurotransmitter systems and myocardial sodium channel blockade (Bauman and DiDomenico, 2002; Wilson and Shelat, 2003; Knuepfer, 2003). Because of cocaine's ability to readily cross the blood brain barrier and its widespread effects on the central and peripheral nervous systems, overdose can result in sudden death (see Bauman and DiDomenico, 2002 for review).

Although the mechanism of cocaine's action is well understood, this information has not yet resulted in the development of an effective antagonist of cocaine that could be used in abuse and overdose situations. The rapid and pleiotropic effects of cocaine present a complex problem for the treatment of acute cocaine toxicity (Carroll and Kuhar, 1999). The two types of therapies that are available for the treatment of opioid abuse, antagonism (e.g., naltrexone) and replacement (e.g., methadone), do not have parallels in the case of cocaine, although attempts at the latter are being considered (e.g., Grabowski et al., 2004). One approach is to prevent or reduce the cocaine from reaching sites of action by administering either endogenous esterases, cocaine specific antibodies, or a catalytic antibody.

Naturally occurring cocaine is hydrolyzed at the benzoyl ester by serum butyrylcholinesterase (BChE) to nontoxic ecgonine methyl ester and benzoic acid. In the liver, carboxylesterase hCE-2 hydrolyzes the methyl ester to yield benzoylecgonine and methanol. The elimination half-life of cocaine in the blood ranges from 0.5 to 1.5 hr (Inaba, 1989). There have been a few attempts to use naturally occurring BChE or genetically engineered BChE to increase cocaine breakdown (see, e.g., Carmona et al., 2000; Xie et al., 1999; Sun et al., 2002a; Sun et al., 2002b; Duysen et al., 2002; Gao and Brimijoin S, 2004; Gao et al., 2005). Other researchers have utilized a monoclonal antibody, Mab 15A10, as a catalytic antibody to cocaine (see e.g., Landry et al, 1993; Mets et al., 1998), while others are exploring the use of cocaine vaccines (see e.g., Kosten et al., 2002).

A bacterium, *Rhodococcus* sp. MB 1, indigenous to the soil surrounding the coca plant, has evolved the capacity to utilize cocaine as its sole carbon and nitrogen source. The bacterium expresses a cocaine esterase (CocE) that acts similarly to BChE to hydrolyze the benzoyl ester of cocaine, yielding ecgonine methyl ester and benzoic acid (FIG. 1) (Bresler et al., 2000; Turner et al., 2002; Larsen et al., 2002). The gene for CocE has been isolated and cloned (Bresler et al., 2000), and the crystal structure of CocE has been determined (Turner et al., 2002; Larsen et al., 2002).

The purified enzyme (MW~65 kDa) catalyzes cocaine very efficiently with Michaelis-Menten kinetics $k_{cat}=7.2$ s$^{-1}$ and $K_m=640$ nM (Turner et al., 2002; Larsen et al., 2002), nearly three orders of magnitude greater than endogenous esterases and, most likely, would act quickly enough to detoxify humans who have overdosed on cocaine (Landry et al., 1993; Mets et al., 1998). Additionally, the esterase also metabolizes cocaethylene, a potent metabolite of cocaine and alcohol, almost as efficiently as it metabolizes cocaine ($k_{cat}=9.4$ s$^{-1}$ and $K_m=1600$ nM) (Turner et al., 2002; Larsen et al., 2002).

One aspect of the *Rhodococcus* CocE that limits its usefulness is its low thermostability—its $t_{1/2}$ at 37° C. is about 15 minutes, whereas its $t_{1/2}$ at 4° C. is >6 mo (PCT Patent Application PCT/US2007/015762, incorporated by reference herein). Thermostability was genetically engineered into CocE, with several mutant proteins having an increased $t_{1/2}$ at 37° C. up to ~326 min (Id.).

There is a need for additional methods and compositions for thermostabilization of CocE. The present invention addresses that need.

SUMMARY

The inventors have discovered that certain compounds thermostabilize wild-type CocE, and further thermostabilize CocE mutants that were already more thermostable than wild-type CocE.

Thus, the application is directed to compositions comprising a cocaine esterase (CocE) and a compound, where the CocE in the presence of the compound is more thermostable than the CocE in the absence of the compound.

The application is also directed to methods of thermostabilizing a cocaine esterase (CocE). The methods comprise combining the CocE with the compound

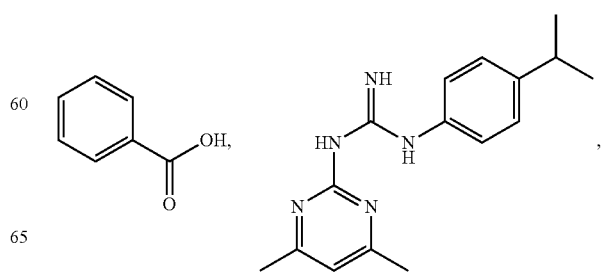

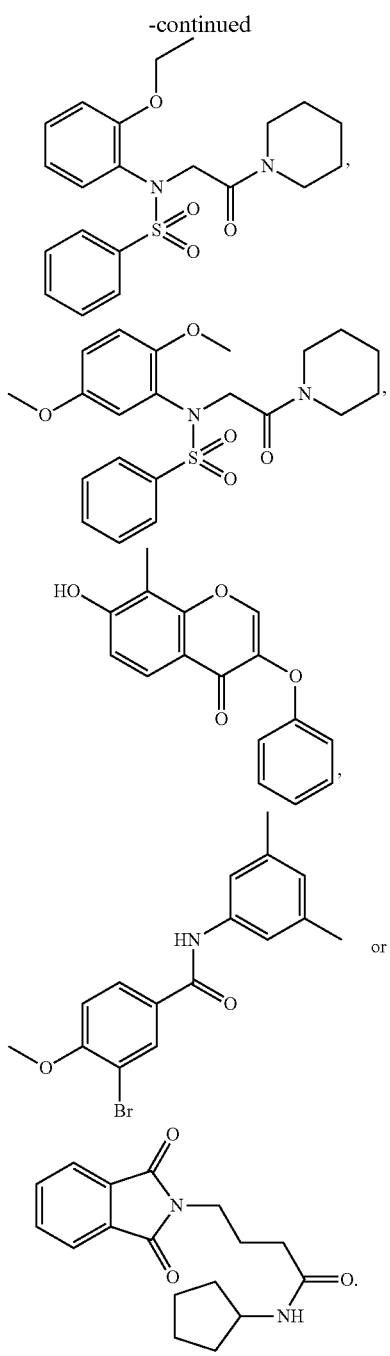

-continued

The application is additionally directed to methods of treating a mammal undergoing a cocaine-induced condition. The methods comprise administering the above-described composition to the mammal in a manner sufficient to reduce the effects of the cocaine-induced condition on the mammal.

Also, the application is directed to methods of treating a mammal undergoing a cocaine overdose. The methods comprise administering the above-described composition to the mammal in a manner sufficient to reduce the effects of the cocaine on the mammal.

The application is further directed to methods of treating a mammal having a cocaine dependence. The methods comprise administering the above-described composition to the mammal in a manner sufficient to reduce the effects of the cocaine dependence on the mammal.

Additionally, the application is directed to methods of determining whether a compound is a thermostabilizing agent for a protein. The methods comprise measuring the thermostability of the protein with and without the compound. With these methods, a compound that causes the protein to be more thermostable is a thermostabilizing agent for the protein.

The application is also directed to the use of the above compositions for the manufacture of a medicament for the treatment of a cocaine-induced condition.

The application is additionally directed to the use of the above compositions for the treatment of a cocaine-induced condition.

It has also been discovered that the CocE mutant L169K/G173Q has an unexpectedly high degree of thermostablity. See Example 5.

Thus, the application is additionally directed to an isolated nucleic acid encoding a CocE polypeptide comprising an amino acid sequence that has at least 85% sequence identity with the polypeptide of SEQ ID NO:1, wherein the encoded CocE polypeptide has (a) the substitutions L169K and G173Q, and (b) esterase activity with increased thermostability at 37° C. as compared to wild-type CocE.

The application is also directed to the CocE polypeptide comprising an amino acid sequence that has at least 85% sequence identity with the polypeptide of SEQ ID NO:1, wherein the encoded CocE polypeptide has the substitutions L169K and G173Q, and esterase activity with increased thermostability at 37° C. as compared to wild-type CocE. Compositions comprising the polypeptide in a pharmaceutically acceptable carrier are also provided.

In additional embodiments, the application is directed to a method of treating a mammal undergoing a cocaine-induced condition. The method comprises administering the composition described immediately above to the mammal in a manner sufficient to reduce the effects of the cocaine-induced condition on the mammal. The use of that composition for the manufacture of a medicament for the treatment of a cocaine-induced condition is also provided, as is the use of that composition for the treatment of a cocaine-induced condition.

BRIEF DESCRIPTION OF THE DRAWINGS

FIG. 2A is a graph of cocaine denaturation over time in the absence of CocE.

FIG. 2B is a graph of cocaine denaturation over time in the presence of 62.5 ng/ml CocE.

FIG. 2C is a graph of cocaine denaturation over time in the presence of 250 ng/ml CocE.

FIG. 7A is a chemical structure of phenylboronic acid (PBA).

FIG. 7B is a graph showing the thermostabilization of CocE by phenylboronic acid (PBA).

FIG. 7C is a reaction scheme showing the enzymatic cleavage of 4-nitrophenylacetate.

FIG. 7D is a photograph of a nondenaturing gel. FIG. 7E is a densitometry curve.

FIG. 10A is the structure of compound 6031818.

FIG. 10B is a graph showing the compound is a weak inhibitor of 4-nitrophenyl acetate cleavage.

FIG. 10C is a graph showing the compound does not inhibit cocaine cleavage at all.

FIG. 11A is the structure of compound 6031818.

FIG. 11B shows the ability of that compound to thermostabilize CocE when 4NPA is used as a substrate.

FIG. 11C shows the ability of that compound to thermostabilize CocE when cocaine is used as a substrate.

FIG. 12A shows the structure of compound 6169221.

FIG. 12B shows the compound did not inhibit 4-nitrophenyl acetate cleavage.

FIG. 12C shows the compound did not inhibit cocaine cleavage.

FIG. 13A is the structure of compound 6169221.

FIG. 13B shows the ability of that compound to thermostabilize CocE when 4NPA is used as a substrate.

FIG. 13C shows the ability of that compound to thermostabilize CocE when cocaine is used as a substrate.

FIG. 14A is the chemical structure of compound 5804236.

FIG. 14B is a graph showing the compound did not inhibit 4-nitrophenyl acetate cleavage.

FIG. 14C is a graph showing the compound did not inhibit cocaine cleavage.

FIG. 15A is the chemical structure of compound 5804236.

FIG. 15B is a graph showing the ability of that compound to thermostabilize CocE when 4NPA is used as a substrate.

FIG. 15C is a graph showing the ability of that compound to thermostabilize CocE when cocaine is used as a substrate.

FIG. 16A is a circular dichroism spectrum of CocE WT.

FIG. 16B is a graph showing the melting temperature of CocE WT.

FIG. 16C is a circular dichroism spectrum of T172R mutant.

FIG. 16D is a graph showing the melting temperature of T172R mutant.

FIG. 17A is a circular dichroism spectrum of CocE WT in the presence of benzoic acid.

FIG. 17B is a graph showing the melting temperature of CocE WT in the presence of benzoic acid.

FIG. 17C is a circular dichroism spectrum of CocE WT in the presence of phenylboronic acid.

FIG. 17D is a graph showing the melting temperature of CocE WT in the presence of phenylboronic acid.

FIG. 18A is a circular dichroism spectrum of the L169K mutant.

FIG. 18B is a graph showing the melting temperature of the L169K mutant.

FIG. 18C is a circular dichroism spectrum of the L169K mutant in the presence of phenylboronic acid.

FIG. 18D is a graph showing the melting temperature of the L169K mutant in the presence of phenylboronic acid.

FIG. 19A is circular dichroism spectra of PBS, compound 6031818, and CocE in the presence of compound 6031818.

FIG. 19B is a graph showing the melting temperature of CocE WT in the presence of 6031818.

FIG. 19C is circular dichroism spectra of CocE WT in the presence of 6031818.

FIG. 19D shows the irreversible melting of CocE WT in the presence of 6031818.

FIG. 22A shows cocaine esterase is composed of three distinct domains, as demarcated.

FIG. 22B shows point mutations predicted by computational methods superimposed on the crystal structure of wt-CocE. Coordinates were obtained from the RCSB database (pdb:1JU4) by Larsen et al (2002). Structure models were generated and rendered with PyMol (DeLano Scientific, Palo Alto, Calif.).

FIG. 28A is a graph showing 0.1 mg i.v. CocE or mutants administered at different time points before cocaine administration (180 mg/kg, i.p.).

FIG. 28B is a graph showing 0.3 mg i.v. CocE or mutants administered at different time points before cocaine administration (180 mg/kg, i.p.).

FIG. 28C is a graph showing 1 mg i.v. CocE or mutants administered at different time points before cocaine administration (180 mg/kg, i.p.).

FIG. 31A high resolution crystal structures of wt-CocE.
FIG. 31B high resolution crystal structure of T172R.
FIG. 31C high resolution crystal structures of wt-CocE.
FIG. 31D high resolution crystal structure of G173Q.
FIG. 31E high resolution crystal structures of wt-CocE.
FIG. 31F high resolution crystal structure of L169K.

FIG. 33A is an omit map of the DBC molecule showing carbon density at 5 sigma, oxygen density at 12 sigma, and sulfur density at 20 sigma.

FIG. 33B depicts the previously reported binding site of the transition-state analog phenyl boronic acid (pdb:1JU3), which is analogous to the DBC binding site. Omit map density for the L169K mutant is shown, which coordinates a water molecule which hydrogen bonds to the DBC ring.

FIG. 37A is a graph showing a time course of protection of mice from a lethal cocaine dose by 1 mg CocE L169K/G173Q mutant; 1 mg CocE L169K mutant; 1 mg CocE T172R/G173Q mutant; and 1 mg wild type CocE.

FIG. 37B is a graph showing a time course of protection of mice from a lethal cocaine dose by 1 mg CocE L169K/G173Q; 0.32 mg CocE L169K/G173Q; and 0.1 mg CocE L169K/G173Q.

DETAILED DESCRIPTION

Figure 1:
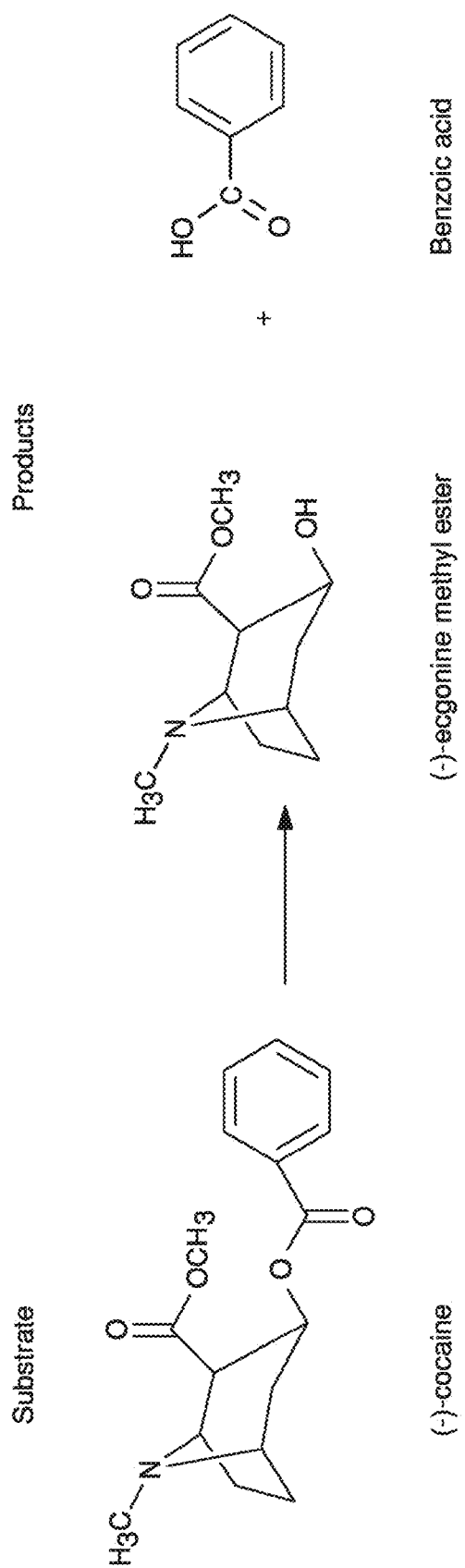
FIG. 1 shows the metabolism of cocaine catalyzed by *Rhodococcus* cocaine esterase (CocE).

The inventors have discovered that certain compounds thermostabilize wild-type CocE, and further thermostabilize CocE mutants that were already more thermostable than wild-type CocE. See Examples 1-3.

Thus, the application is directed to compositions comprising a cocaine esterase (CocE) and a compound, where the CocE in the presence of the compound is more thermostable than the CocE in the absence of the compound.

The resulting increase in thermostability of the CocE in the presence of the compound increases the half-life of the enzyme at 37° C. at least about 5 minutes, preferably at least about 10, 15, 20, 25, 30, 35 or 40 minutes, or more.

Thermostability of a given polypeptide can be assessed by a variety of methods known to the art, including for example measuring circular dichroism (CD) spectroscopy (as in, e.g., Example 2, below) or differential scanning calorimeter. See also PCT Patent Application PCT/US2007/015762, published as WO/2008/008358, incorporated by reference. Preferably, thermostability is determined by measuring enzyme activity over time at a low and high temperature with and without the compound, to determine whether, and to what degree, the compound causes the enzyme to maintain enzymatic activity at the higher temperature more than without the compound. A preferred low temperature is room temperature (i.e., ~25° C.); a preferred high temperature is 37° C. However, any temperature ranges can be used. The skilled artisan could determine the best temperature range for any particular application without undue experimentation.

As used herein, a CocE is an enzyme having an amino acid sequence at least 80% identical to SEQ ID NO:1 and is capable of specifically catalyzing the cleavage of cocaine into ecgonine methyl ester and benzoic acid. Preferably, the CocE has an amino acid sequence at least 90%, more preferably, 95%, even more preferably 99% identical to SEQ ID NO:1. In some preferred embodiments, the CocE has an amino acid sequence identical to SEQ ID NO:1.

In other embodiments, the CocE has a mutation, such as those described in PCT Patent Application PCT/US2007/015762, including mutants that have increased thermostability over the wild type (SEQ ID NO:1) and mutants that do not. Preferred mutants are those where the CocE has the amino acid sequence of SEQ ID NO:1 except for the substitution L163V, V225I, I218L, A310D, A149S, S159A, S265A, S56G, W220A, S140A, F189L, A193D, T254R, N42V, V262L, L508G, Y152H, V160A, T172R, Y532F, T74S, W285T, L146P, D533S, A194R, G173Q, C477T, K531A, R41I, L119A, K46A, F84Y, T172R/G173Q, L169K, F189A, N197K, R182K, F189K, V190K, Q191K, or A194K, or any combination of these mutated amino acid residues. In some of these embodiments, the CocE has the amino acid sequence of SEQ ID NO:1 except for the substitution T172R, S159A, N197K, L169K, F189K, G173Q, or T172R/G173Q. In other of these embodiments, the CocE has the amino acid sequence of SEQ ID NO:1 except for the substitution L169K/G173Q.

A compound within the scope of these embodiments can increase the thermostability of the wild type and/or a mutant CocE described above.

The CocE can also be pegylated or otherwise treated to increase the duration of action, heat stability, and/or decrease immunogenicity. Pegylation can further enhance the thermostability of the CocE-compound compositions and, when used in vivo, increase serum half life by decreasing renal clearance, proteolysis, macrophage uptake, and immunological response.

The CocE-compound compositions can be encapsulated into red blood cells (RBC) so as to increase the duration of action and heat stability, and decrease immunogenicity. In preferred compositions, the compound is:

-continued
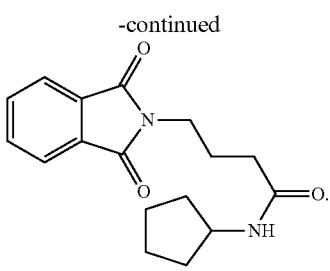
More preferably, the compound is
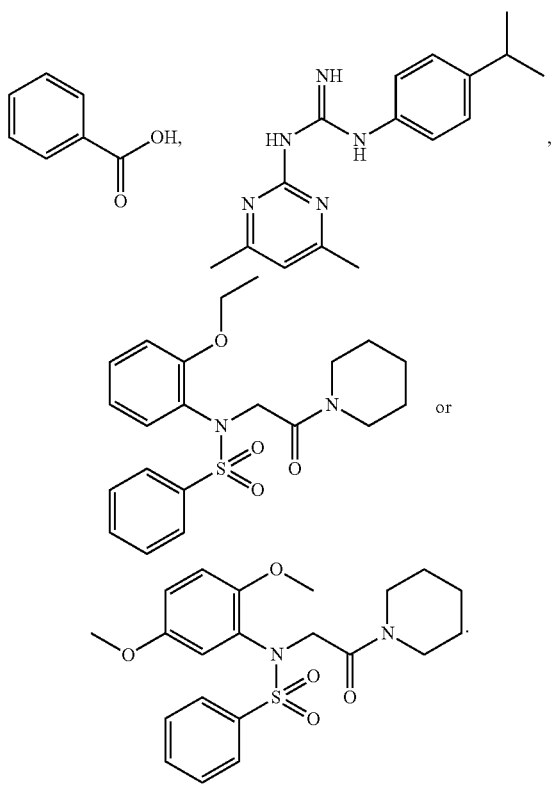
Even more preferably, the compound is
(6031818)
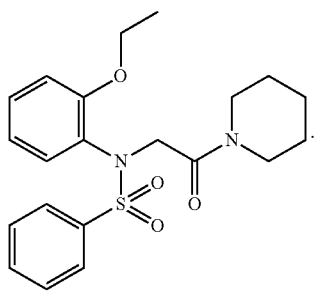
In other preferred embodiments, the compound is
(benzoic acid)
The compound can also be
(5804236)
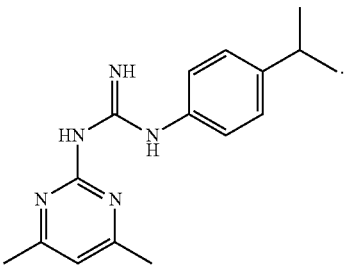
The compound can additionally be
(6169221)
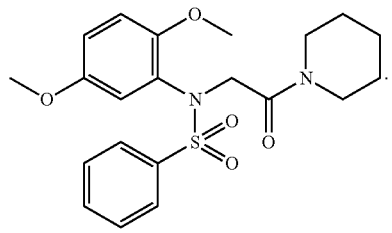
Additionally, the compound can be
(F6 460)
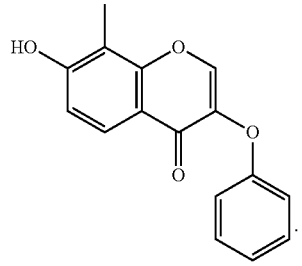
Further, the compound can be
(G2 30460)
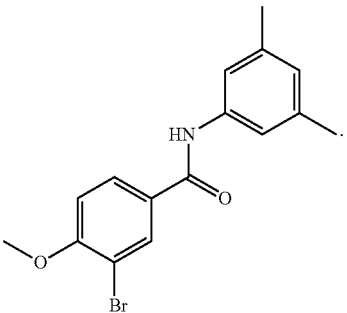
The compound can also be
(G3 30390)
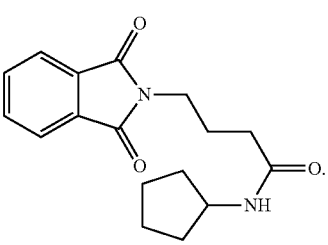 [SMILES: O=C(CCCN1C(=O)c2ccccc2C1=O)NC1CCCC1]

The compositions of the present invention can comprise more than one of any of the above-identified compounds that thermostabilize CocE.

In some embodiments of these compositions, in particular where they are used for therapeutic purposes, the composition is in a pharmaceutically acceptable carrier.

The CocE-compound compositions described herein can be formulated by any conventional manner using one or more pharmaceutically acceptable carriers and/or excipients (see e.g., Gennaro (2005) Remington the Science and Practice of Pharmacy 21st ed. Lippincott Williams & Wilkins, ISBN 0781746736). Such formulations will contain a therapeutically effective amount of the CocE-compound compositions, preferably in purified form, together with a suitable amount of carrier so as to provide the form for proper administration to the subject. The formulation should suit the mode of administration. The CocE-compound compositions of use with the current application can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The CocE-compound compositions can also be administered in combination with one or more additional agents disclosed herein and/or together with other biologically active or biologically inert agents. Such biologically active or inert agents can be in fluid or mechanical communication with the agent(s) or attached to the agent(s) by ionic, covalent, Van der Waals, hydrophobic, hydrophilic or other physical forces.

The CocE-compound compositions described herein can be administered parenterally, including by intravenous, intramuscular, subcutaneous, or intraperitoneal injections. Excipients, commonly used in the parenteral delivery of small drug molecules, including solubility enhancers, osmotic agents, buffers, and preservatives, can also be included in biomolecule formulations. Inclusion of antiaggregation and antiadsorption agents, such as surfactants and albumin, when formulating and delivering biomolecules can add increased stability and decrease the risk of the active biomolecule interacting with an interface, which can lead to unfolding, aggregation, and/or precipitation. The CocE-compound compositions can be lyophilized for added stability during storage, and re-processed before parenteral administration.

Pulmonary delivery of the CocE-compound compositions is also contemplated. Additionally, controlled-release (or sustained-release) preparations can be formulated to extend the activity of the mutant CocE polypeptide and reduce dosage frequency, as is known in the art.

The CocE-compound compositions can be encapsulated and administered in a variety of carrier delivery systems. Examples of carrier delivery systems for use with mutant CocE polypeptides described herein include microspheres (see e.g., Varde & Pack (2004) Expert Opin. Biol. 4(1) 35-51), hydrogels (see generally, Sakiyama et al. (2001) FASEB J. 15, 1300-1302), polymeric implants (see generally, Teng et al. (2002) Proc. Natl. Acad. Sci. U.S.A. 99, 3024-3029), smart polymeric carriers (see generally, Stayton et al. (2005) Orthod Craniofacial Res 8, 219-225; Wu et al. (2005) Nature Biotech (2005) 23(9), 1137-1146), and liposomes (see e.g., Galovic et al. (2002) Eur. J. Pharm. Sci. 15, 441-448; Wagner et al. (2002) J. Liposome Res. 12, 259-270).

The application is also directed to methods of thermostabilizing a cocaine esterase (CocE). The methods comprise combining the CocE with the compound

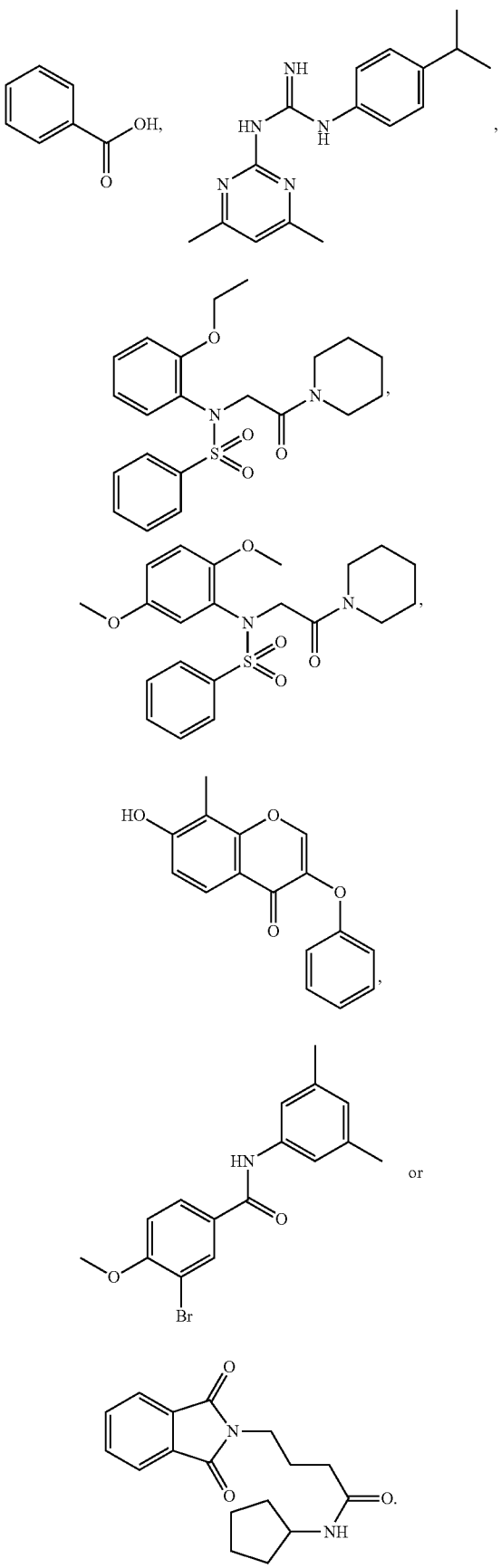

Preferably, the compound is
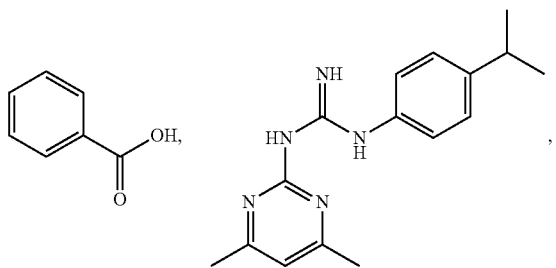
More preferably, the compound is
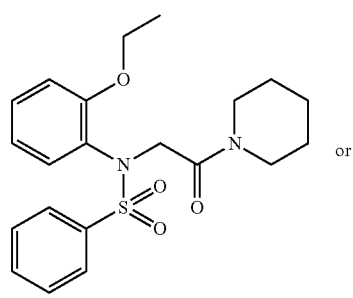
(6031818)
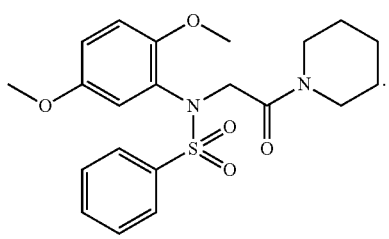
In other preferred embodiments, the compound is
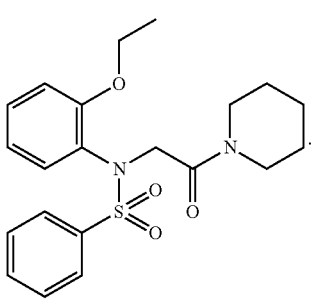
(benzoic acid)
The compound can also be
(5804236)
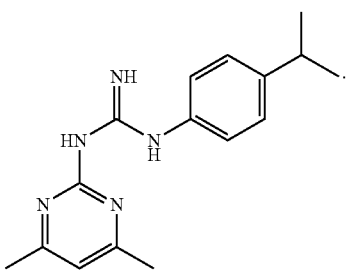
The compound can additionally be
(6169221)
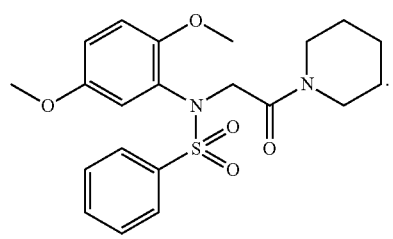
Additionally, the compound can be
(F6 460)
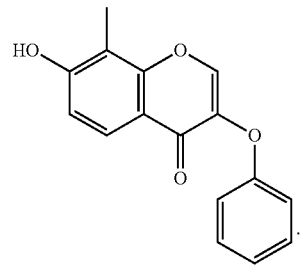
Further, the compound can be
(G2 30460)
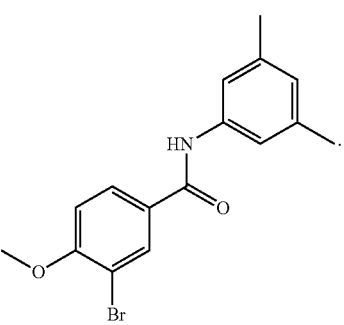
The compound can also be
(G3 30390)
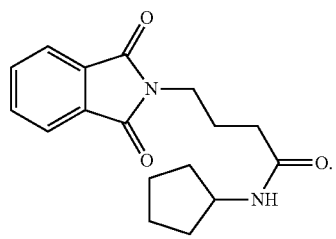 [SMILES: O=C(CCCN1C(=O)c2ccccc2C1=O)NC1CCCC1]

In these methods, the CocE can be combined with more than one thermostabilizing compound, for example one of the compounds described above, or with any other compound.

Preferably, the CocE comprises an amino acid sequence at least 90% identical to SEQ ID NO:1; more preferably at least 95% identical to SEQ ID NO:1; even more preferably at least 99% identical to SEQ ID NO:1. In other preferred embodiments, the CocE comprises the amino acid sequence of SEQ ID NO:1. In additional embodiments, the CocE is a thermostable mutant of a wild-type CocE having the amino acid sequence of SEQ ID NO:1. Preferred examples of such thermostable mutants is the CocE having the amino acid sequence of SEQ ID NO:1 except for the substitution T172R, S159A, N197K, L169K, F189K, G173Q, or T172R/G173Q. Additionally, the CocE can have the amino acid sequence of SEQ ID NO:1 except for the substitution L169K/G173Q.

The methods of these embodiments can be performed where the CocE is in vitro, for example to thermostabilize CocE upon purification or during storage. Preferably, however, the CocE is in a living mammal. Toward those embodiments, an aspect of this application is directed toward catalytic degradation approaches to anti-cocaine therapeutics. Provided are treatments, both prophylactic and therapeutic, of cocaine-induced conditions through the administration of thermostable, esterase-active, CocE-compound compositions to a subject in need thereof. It is the increase in thermostability provided by the thermostabilizing compound that enables a much more rapid and effective response to symptoms of cocaine toxicity that sets the CocE-compound compositions described above apart from other treatment options.

The application is additionally directed to methods of treating a mammal undergoing a cocaine-induced condition. The methods comprise administering the above-described CocE-compound composition to the mammal in a manner sufficient to reduce the effects of the cocaine-induced condition on the mammal.

A determination of the need for treatment will typically be assessed by a history and physical exam consistent with the cocaine-induced condition. It is contemplated that the present methods can be used for treatment of any cocaine-induced condition including, but are not limited to, cocaine overdose, cocaine toxicity, and cocaine dependence and/or addiction. The diagnosis of such conditions is within the skill of the art. For example, the diagnosis of cocaine toxicity can include assessment of convulsions, grand-mal seizures, cardiac arrest, myocardial infarction, cardiac arrhythmias, increased blood pressure, stroke, drug-induced psychosis, dissecting aneurysm, and increased myocardial oxygen demand. As another example, in the case of cocaine dependence and/or addiction, withdrawal symptoms include subjective sensations of mild to severe dysphora, depression, anxiety, or irritability. Subjects with an identified need of therapy include those with a diagnosed cocaine-induced condition, an indication of a cocaine-induced condition, and subjects who have been treated, are being treated, or will be treated for a cocaine-induced condition. These methods can be used to treat any mammal, including, but not limited to, rodents, rabbits, guinea pigs, horses, cows, dogs, cats, sheep and pigs, and most preferably humans.

An effective amount of the CocE-compound compositions described herein is generally that which can reduce the cocaine-toxicity or the severity of a cocaine-induced condition. Reduction in severity includes, for example, an arrest or a decrease in symptoms, physiological indicators, biochemical markers, or metabolic indicators. When used in the methods of the invention, a therapeutically effective amount of CocE-compound compositions described herein can be employed in pure form or, where such forms exist, in pharmaceutically acceptable salt form and with or without a pharmaceutically acceptable excipient. For example, CocE-compound compositions can be administered at a reasonable benefit/risk ratio applicable to any medical treatment, in an amount sufficient to substantially reduce the cocaine concentration in the blood and/or tissues of the subject.

Toxicity and therapeutic efficacy of CocE-compound compositions can be determined by standard pharmaceutical procedures in cell cultures and/or experimental animals for determining the LD50 (the dose lethal to 50% of the population) the ED50, (the dose therapeutically effective in 50% of the population), or other parameters.

The amount of CocE-compound compositions that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses. Administration of the CocE-compound composition can occur as a single event or over a time course of treatment. For example, a CocE-compound composition can be administered daily, weekly, bi-weekly, or monthly. For some conditions, treatment could extend from several weeks to several months or even a year or more.

The specific therapeutically effective dose level for any particular subject will depend upon a variety of factors including the cocaine-induced condition being treated and the severity of the cocaine-induced condition; activity of the mutant CocE polypeptide employed; the specific composition employed; the age, body weight, general health, sex and diet of the patient; the time of administration; the route of administration; the plasma half-life of the mutant CocE polypeptide; the rate of excretion of the mutant CocE polypeptide employed; the duration of the treatment; drugs used in combination or coincidental with the mutant CocE polypeptide employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Shama (2004) Applied Biopharmaceutics & Pharmacokinetics, McGraw-Hill/Appleton & Lange, ISBN 0071375503). It will be understood by a skilled practitioner that the total daily usage of the CocE-compound compositions for use in embodiments of the invention disclosed herein can be decided without undue experimentation by the attending physician within the scope of sound medical judgment.

The CocE-compound compositions described herein can also be used in combination with other therapeutic modalities. Thus, in addition to the therapies described herein, one can also provide to the subject other therapies known to be efficacious for particular cocaine-induced conditions.

Thus, in some embodiments of these methods, the mammal is addicted to cocaine. In other embodiments, the mammal is undergoing a cocaine overdose.

The CocE for these methods can be a thermostable mutant of a wild-type CocE having the amino acid sequence of SEQ ID NO:1. Preferred such mutants have the amino acid sequence of SEQ ID NO:1 except for the substitution T172R, S159A, N197K, L169K, F189K, G173Q, T172R/G173Q, or L169K/G173Q. CocE mutants having more than one mutation, preferably more than one thermostabilizing mutation, are also useful for these treatment methods.

These methods are not limited to the use of any particular thermostabilizing compound. Preferably, the compound is
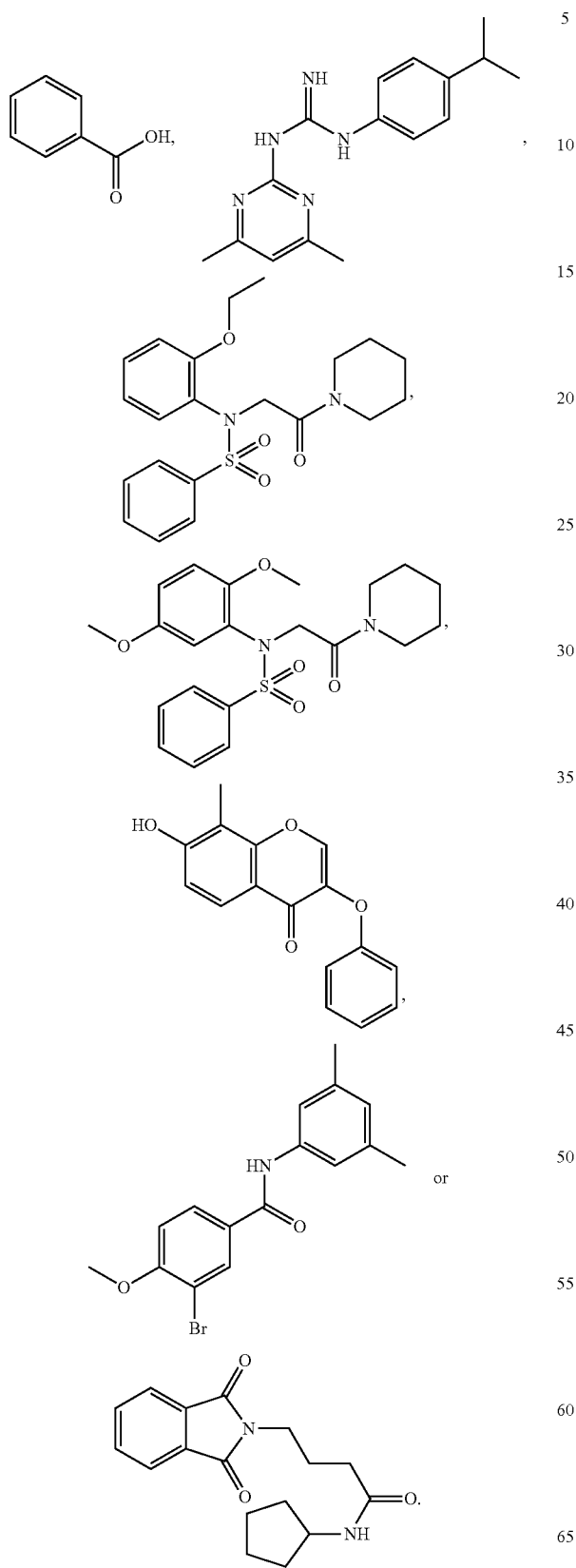
or
More preferably, the compound is
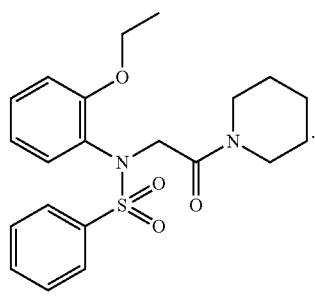
(6031818)
In other preferred embodiments, the compound is
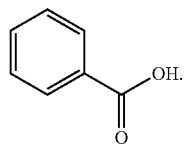
(benzoic acid)
The compound can also be
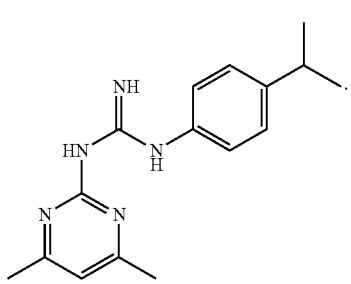
(5804236)
The compound can additionally be
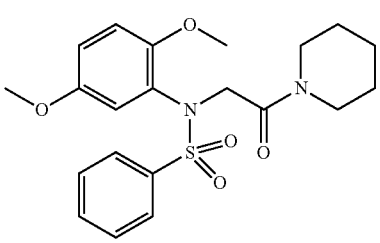
(6169221)
Additionally, the compound can be
(F6 460)
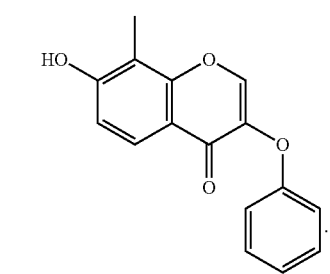

Further, the compound can be

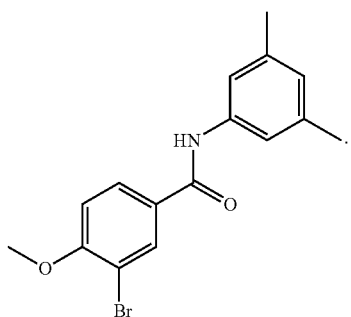

(G2 30460)

The compound can also be

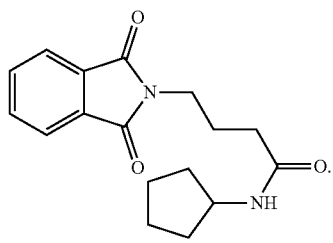

(G3 30390)

In these methods, the CocE can be combined with more than one thermostabilizing compound, for example one of the compounds described above, or with any other compound.

The application is also directed to methods of treating a mammal undergoing a cocaine overdose. The methods comprise administering the above-described composition to the mammal in a manner sufficient to reduce the effects of the cocaine on the mammal.

These methods can be used to treat any mammal, including, but not limited to, rodents, rabbits, guinea pigs, horses, cows, dogs, cats, sheep and pigs, and most preferably humans.

As with the treatment methods described above, the composition can be administered by any method known in the art. The skilled artisan could determine the best mode of administration for any particular individual without undue experimentation. In some preferred embodiments, the CocE-compound composition is administered to the mammal intravenously.

The CocE for these methods can be a thermostable mutant of a wild-type CocE having the amino acid sequence of SEQ ID NO:1. Preferred such mutants have the amino acid sequence of SEQ ID NO:1 except for the substitution T172R, S159A, N197K, L169K, F189K, G173Q, or T172R/G173Q. In another thermostable mutant, the CocE has the amino acid sequence of SEQ ID NO:1 except for the substitution L169K/G173Q. CocE mutants having more than one mutation, preferably more than one thermostabilizing mutation, are also useful for these treatment methods.

These methods are not limited to the use of any particular thermostabilizing compound. Preferably, the compound is

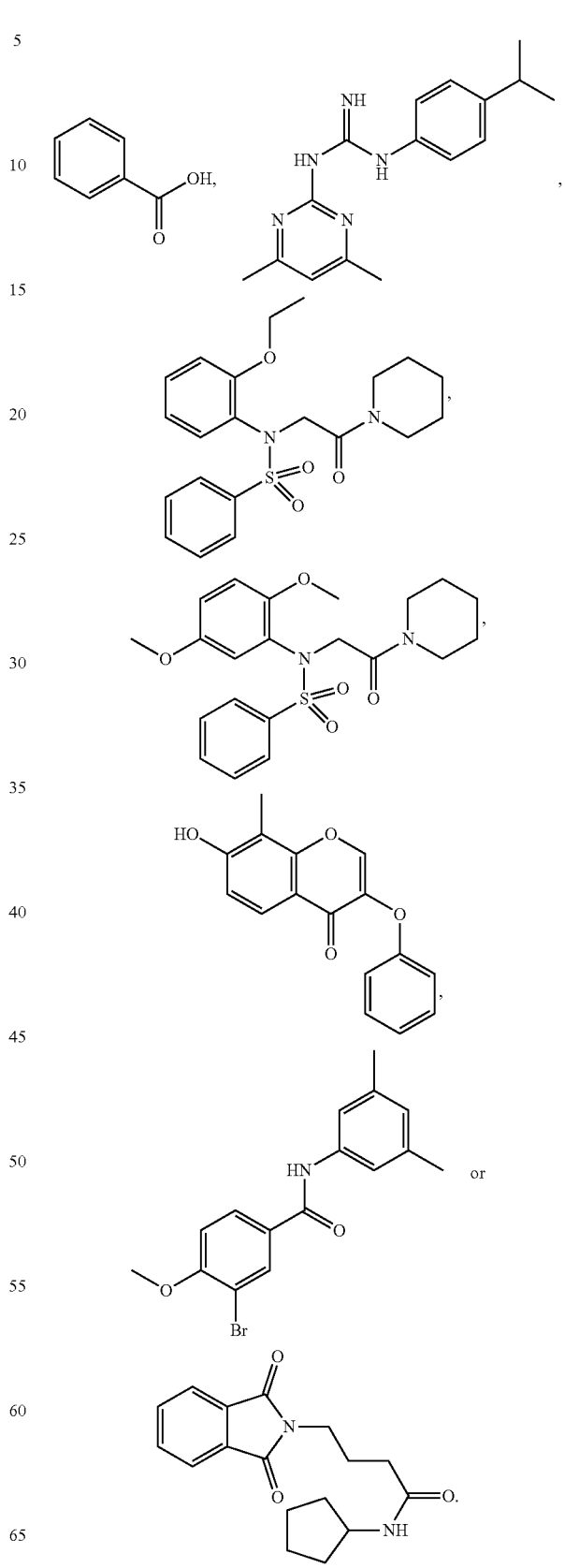

More preferably, the compound is

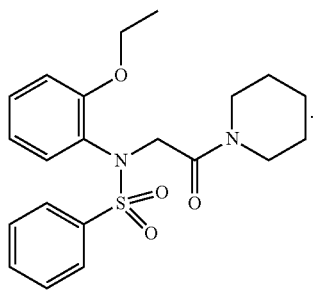
(6031818)

In other preferred embodiments, the compound is

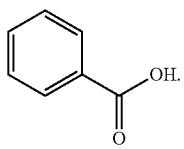
(benzoic acid)

The compound can also be

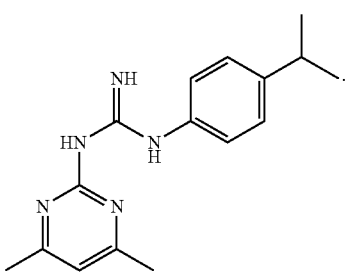
(5804236)

The compound can additionally be

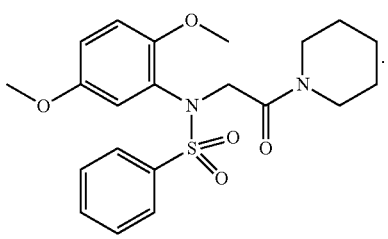
(6169221)

Additionally, the compound can be

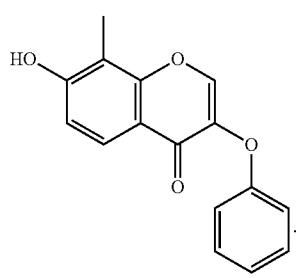
(F6 460)

Further, the compound can be

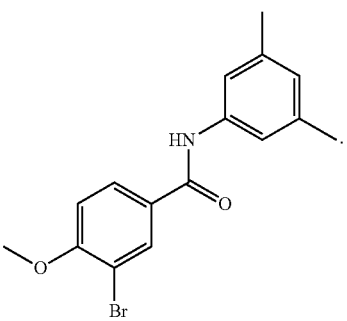
(G2 30460)

The compound can also be

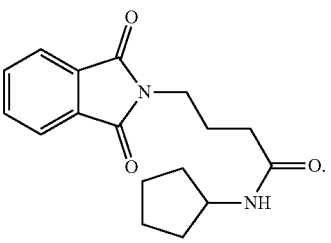
(G3 30390)

In these methods, the CocE can be combined with more than one thermostabilizing compound, for example one of the compounds described above, or with any other compound.

The invention is further directed to methods of treating a mammal having a cocaine dependence. The methods comprise administering the above-described composition to the mammal in a manner sufficient to reduce the effects of the cocaine dependence on the mammal.

These methods can be used to treat any mammal, including, but not limited to, rodents, rabbits, guinea pigs, horses, cows, dogs, cats, sheep and pigs, and most preferably humans.

As with the treatment methods described above, the composition can be administered by any method known in the art. The skilled artisan could determine the best mode of administration for any particular individual without undue experimentation. In some preferred embodiments, the CocE-compound composition is administered to the mammal intravenously.

The CocE for these methods can be a thermostable mutant of a wild-type CocE having the amino acid sequence of SEQ ID NO:1. Preferred such mutants have the amino acid sequence of SEQ ID NO:1 except for the substitution T172R, S159A, N197K, L169K, F189K, G173Q, or T172R/G173Q. In another thermostable mutant, the CocE has the amino acid sequence of SEQ ID NO:1 except for the substitution L169K/G173Q. CocE mutants having more than one mutation, preferably more than one thermostabilizing mutation, are also useful for these treatment methods.

These methods are not limited to the use of any particular thermostabilizing compound. Preferably, the compound is

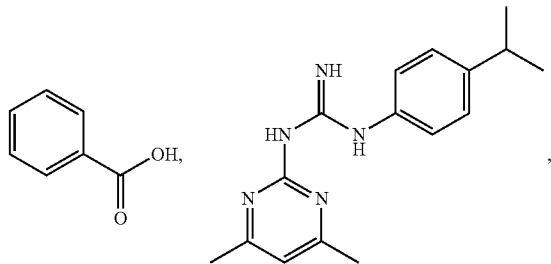
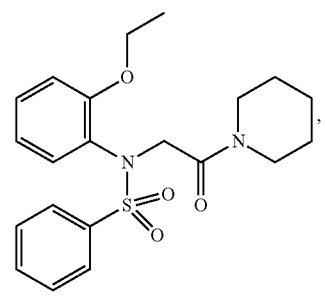
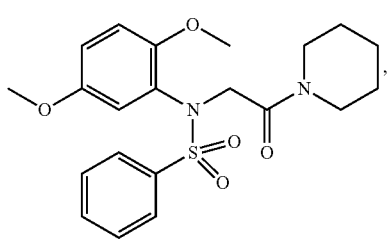
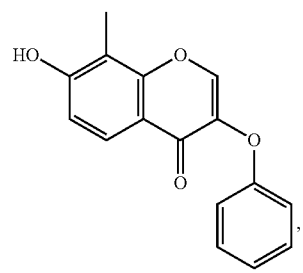
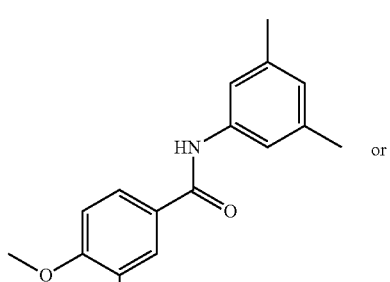
or
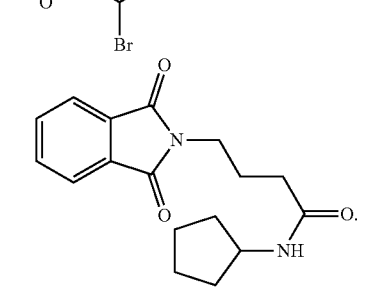
More preferably, the compound is
(6031818)
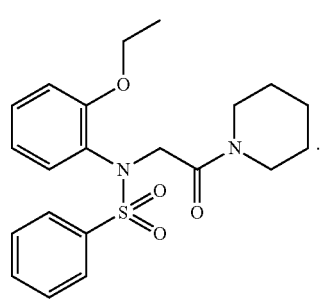
In other preferred embodiments, the compound is
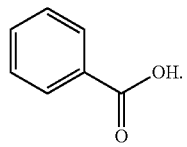
(benzoic acid)
The compound can also be
(5804236)
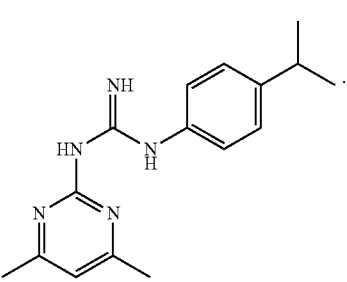
The compound can additionally be
(6169221)
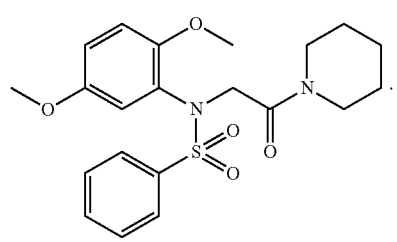
Additionally, the compound can be
(F6 460)
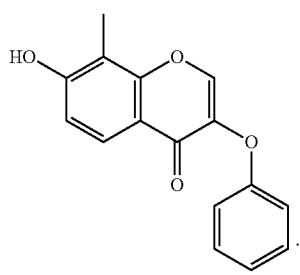

Further, the compound can be

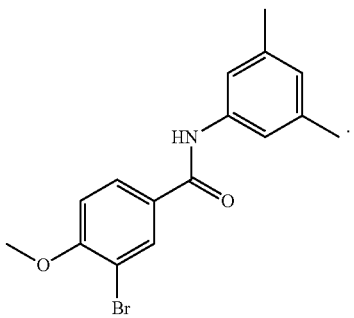
(G2 30460)

The compound can also be

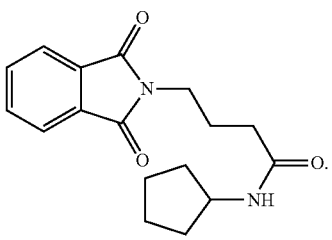 [SMILES: O=C(CCCN1C(=O)c2ccccc2C1=O)NC1CCCC1]
(G3 30390)

In these methods, the CocE can be combined with more than one thermostabilizing compound, for example one of the compounds described above, or with any other compound.

Additionally, the application is directed to methods of determining whether a compound is a thermostabilizing agent for a protein. The methods comprise measuring the thermostability of the protein with and without the compound. With these methods, a compound that causes the protein to be more thermostable is a thermostabilizing agent for the protein. Preferably, the protein is a CocE.

With these methods, the protein can be isolated (i.e., in a test tube outside of a living cell), or produced by cells in culture or in vivo for the thermostability determination.

The activity of the isolated protein with and without the compound can be measured at one or more temperatures to determine the thermostability of the protein imparted by the compound. The temperature at which the activity assay is performed determines the degree of thermostability detection. Thus, initial screening can, for example, be performed at 30° C., and after initial compound selection, screening can be performed with incrementally increasing temperatures (for example, 34° C., 37° C., 40° C., 42.5° C., 45° C., etc.), until a compound of suitable thermostability is achieved. The incremental temperature increases are determined empirically during the procedure, and are affected by the number of hits at particular temperatures and the determined Tm of the initial compounds.

Where the protein is CocE, detection of esterase activity can be performed using a variety of methods, where substrates generally are coupled to a specific detection system. Appropriate substrates for use in determining esterase activity can include cocaine, tritiated ($^3$H) cocaine, cocaine substrate derivatives such as a thio-cocaine derivative, and/or substrates that report general esterase activity such as 4-nitrophenyl acetate. The detection system can be directly coupled to the specifics of the substrate, for example: cleavage of unmodified cocaine can be detected by monitoring changes in cocaine absorbance at 240 nm, or by monitoring pH changes that result from the accumulation of the acidic benzoic acid product, or through the use of cocaine aptamers (see e.g., Stojanovic, M. N., de Prada, P. & Landry, D. W. (2001) J Am Chem Soc 123, 4928-4931; Stojanovic, M. N. & Landry, D. W. (2002) J Am Chem Soc 124, 9678-9679) by monitoring changes in fluorescence upon degradation of cocaine; cleavage of tritiated ($^3$H) cocaine can be detected by acidification and detection of tritiated benzoic acid product through separation by chromatography; cleavage of cocaine derivatives such as thio-cocaine can be monitored by the detection of reactive sulfhydryl groups, through the addition of Ellman's reagent and determination of absorbance changes at 412 nm, or by the addition and visualization of precipitating sulfhydryl reacting heavy metals; cleavage of 4-nitrophenyl acetate can be detected by monitoring changes in absorbance at 420 nm (see e.g., Halgasova, N. et al. (1994) Biochem J 298 Pt 3, 751-755; O'Conner, C. J. & Manuel, R. D. (1993) J Dairy Sci. 76, 3674-3682). See also PCT Publication WO/2008/008358 for further elaboration of the above.

Protein-compound compositions identified through the above procedures, or a similar high throughput assay, can be further evaluated using in vitro procedures described herein and in PCT Publication WO/2008/008358 (e.g., $K_{cat}$ and $K_m$ values, stability at 37°, melting temperature ($T_m$), endotoxin levels, ability to degrade substrate in plasma). Protein-compound compositions exhibiting thermostability over the protein itself can be further evaluated when appropriate using in vivo procedures described herein and in PCT Publication WO/2008/008358 (e.g., potency, duration of action, effects with repeated dosing, and/or immunological evaluation).

Thus, for these screening methods, the protein is preferably an enzyme. More preferably, the protein is a protease. Even more preferably, the protein is an esterase. Most preferably, the protein is a cocaine esterase (CocE), having an amino acid sequence at least 80% identical to SEQ ID NO:1 and is capable of specifically catalyzing the cleavage of cocaine into ecgonine methyl ester and benzoic acid. Preferably, the CocE has an amino acid sequence at least 90%, more preferably, 95%, even more preferably 99% identical to SEQ ID NO:1. In some preferred embodiments, the CocE has an amino acid sequence identical to SEQ ID NO:1.

Since it is desirable that the thermostabilizing compound is effective at a low concentration, it is preferable in these screening methods that the compound is present in the composition at a concentration of less than about 1 mM. More preferably, the compound is present in the composition at a concentration of less than about 0.1 mM. Most preferably, the compound is present in the composition at a concentration of less than about 0.025 mM.

Preferably in these screening methods the thermostability is measured by measuring protein function at a low temperature and a high temperature in the presence and absence of the compound, where the low temperature is near the optimum temperature for protein function and where the protein is less stable at the high temperature than at the low temperature. Preferably, the high temperature is about 37° C., particularly when the protein is a CocE. However, for other enzymes, the high temperature can be greater than about 40° C., greater than about 50° C., greater than about 60° C., greater than about 70° C., greater than about 80° C., greater than about 90° C., greater than about 95° C., or even greater than about 98° C., e.g., with thermostable polymerases for PCR.

Any aspect of protein function can be measured to determine thermostability with and without the compound. Preferred examples of protein function for this purpose is enzyme activity and ligand binding.

The application is also directed to the use of the above compositions for the manufacture of a medicament for the treatment of a cocaine-induced condition. Preferably, the cocaine-induced condition is cocaine overdose, cocaine toxicity, cocaine addiction, or cocaine dependence. Most preferably, the cocaine-induced condition is cocaine overdose.

The CocE for these uses can be a thermostable mutant of a wild-type CocE having the amino acid sequence of SEQ ID NO:1. Preferred such mutants have the amino acid sequence of SEQ ID NO:1 except for the substitution T172R, S159A, N197K, L169K, F189K, G173Q, or T172R/G173Q. In another thermostable mutant, the CocE has the amino acid sequence of SEQ ID NO:1 except for the substitution L169K/G173Q. CocE mutants having more than one mutation, preferably more than one thermostabilizing mutation, are also useful for these treatment methods.

These uses are not limited to the utilization of any particular thermostabilizing compound. Preferably, the compound is

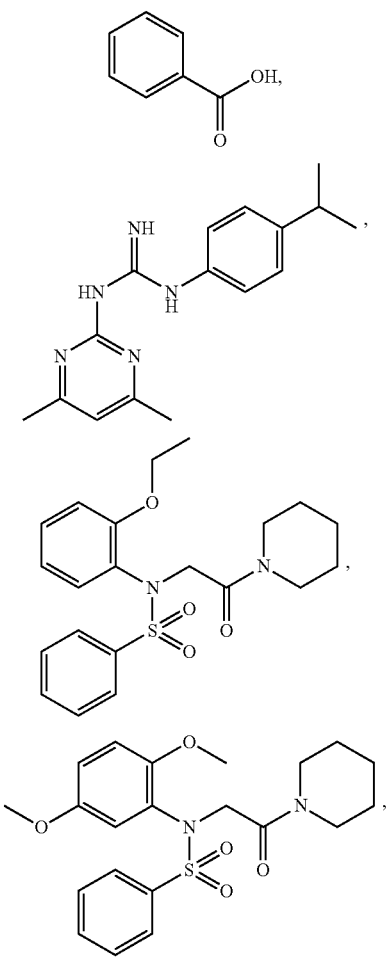

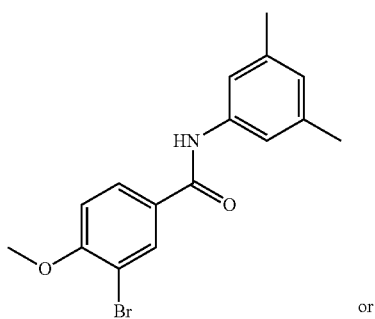

or

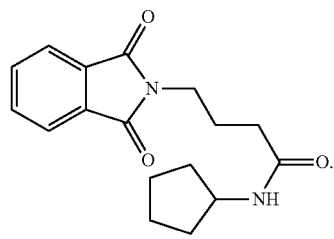 [SMILES: O=C(CCCN1C(=O)c2ccccc2C1=O)NC1CCCC1]

More preferably, the compound is (6031818)

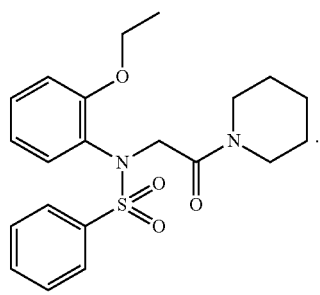

In other preferred embodiments, the compound is

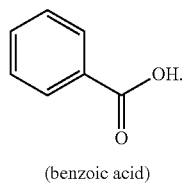

(benzoic acid)

The compound can also be (5804236)

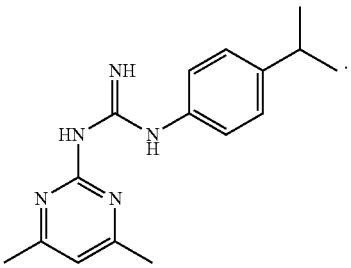

The compound can additionally be

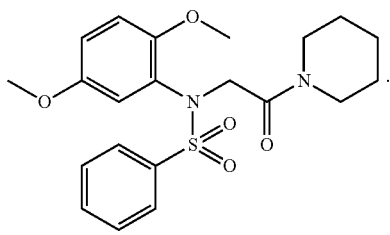

(6169221)

Additionally, the compound can be

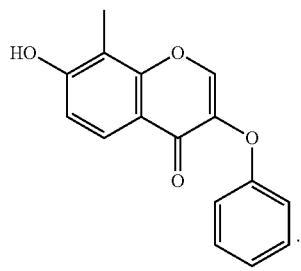

(F6 460)

Further, the compound can be

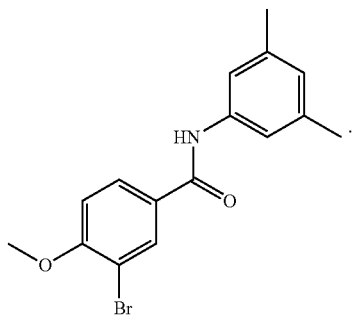

(G2 30460)

The compound can also be

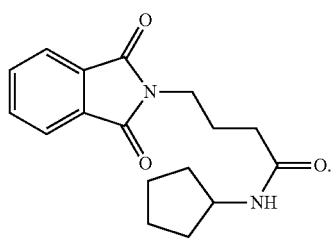

(G3 30390)

In these uses, the CocE can be combined with more than one thermostabilizing compound, for example one of the compounds described above, or with any other compound.

The application is additionally directed to the use of the above compositions for the treatment of a cocaine-induced condition. Preferably, the cocaine-induced condition is cocaine overdose, cocaine toxicity, cocaine addiction, or cocaine dependence. Most preferably, the cocaine-induced condition is cocaine overdose.

The CocE for these uses can be a thermostable mutant of a wild-type CocE having the amino acid sequence of SEQ ID NO:1. Preferred such mutants have the amino acid sequence of SEQ ID NO:1 except for the substitution T172R, S159A, N197K, L169K, F189K, G173Q, or T172R/G173Q. In another thermostable mutant, the CocE has the amino acid sequence of SEQ ID NO:1 except for the substitution L169K/G173Q. CocE mutants having more than one mutation, preferably more than one thermostabilizing mutation, are also useful for these treatment methods.

These uses are not limited to the utilization of any particular thermostabilizing compound. Preferably, the compound is -continued

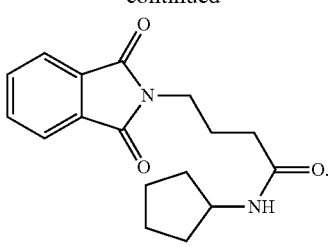

More preferably, the compound is

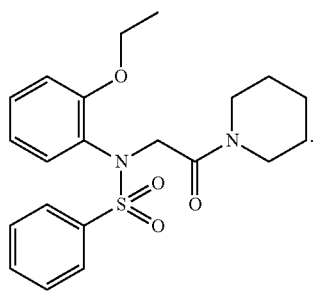 [SMILES: CCOc1ccccc1N(CC(=O)N1CCCCC1)S(=O)(=O)c1ccccc1]

(6031818)

In other preferred embodiments, the compound is

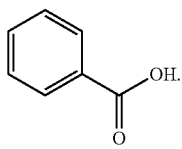

(benzoic acid)

The compound can also be (5804236)

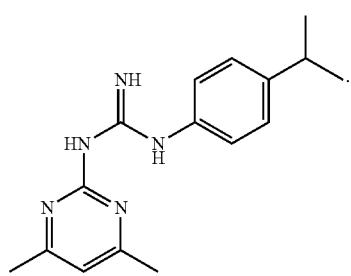

The compound can additionally be (6169221)

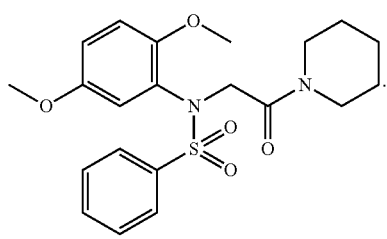

Additionally, the compound can be (F6 460)

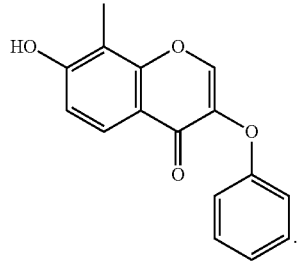

Further, the compound can be (G2 30460)

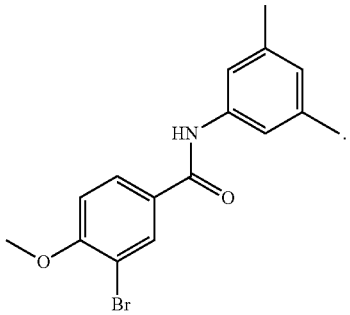

The compound can also be (G3 30390)

In these uses, the CocE can be combined with more than one thermostabilizing compound, for example one of the compounds described above, or with any other compound.

The application is additionally directed to an isolated nucleic acid encoding a CocE polypeptide comprising an amino acid sequence that has at least 85% sequence identity with the polypeptide of SEQ ID NO:1. In these embodiments, the encoded CocE polypeptide has (a) the substitutions L169K and G173Q, and (b) esterase activity with increased thermostability at 37° C. as compared to wild-type CocE. See Example 5, establishing that this polypeptide has a half life of about 72 hours at 37° C., which is more than 300× longer than the wild-type enzyme having the sequence of SEQ ID NO:1. Preferably, the amino acid sequence has at least 90% sequence identity with the polypeptide of SEQ ID NO:1. More preferably, the amino acid sequence has at least 95% sequence identity with the polypeptide of SEQ ID NO:1. Even more preferably, the amino acid sequence has at least 99% sequence identity with the polypeptide of SEQ ID NO:1. In the most preferred embodiments, the nucleic acid encodes a CocE polypeptide that has the sequence of SEQ ID NO:1 except for the substitutions L169K and G173Q.

The application is also directed to CocE polypeptides encoded by any of the above nucleic acids encoding a CocE polypeptide having the L169K and G173Q substitutions. In some embodiments, the CocE polypeptide is in a pharmaceutically acceptable carrier.

In additional embodiments, the application is directed to a method of treating a mammal undergoing a cocaine-induced condition. The method comprises administering the above-described composition comprising the CocE polypeptide having L169K and G173Q substitutions to the mammal in a manner sufficient to reduce the effects of the cocaine-induced condition on the mammal.

Further, the application is directed to the use of the above-described composition comprising the CocE polypeptide having L169K and G173Q substitutions for the manufacture of a medicament for the treatment of a cocaine-induced condition.

The application is additionally directed to the use of the above-described composition comprising the CocE polypeptide having L169K and G173Q for the treatment of a cocaine-induced condition.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE 1

Compounds that Thermostabilize CocE

Cocaine esterase is a bacterially expressed protein that catalyzes the cleavage of cocaine into two inactive byproducts: ecgonine methyl ester and benzoic acid. The protein could theoretically be used in vivo for treatment of cocaine overdose and addiction, however the wild-type protein is not stable at 37° C.

Analysis of CocE action on cocaine cleavage is performed by utilizing the spectroscopic properties of cocaine, which maximally absorbs light at a 240 nm wavelength. CocE activity is measured by monitoring for a decrease in signal at A240, using various concentrations of cocaine, and determining the initial rate of the decrease. From these values the $V_{max}$ of the enzyme can be determined. By pre-incubating the enzyme at 37° C. for various times before monitoring for activity, the half life of CocE at 37° C. can be calculated.

In an ongoing effort to improve CocE thermostability, several mutants of the protein have been made and tested for in vitro half life. Subsequent analysis using gel electrophoresis showed that under native conditions the proteins could be observed to aggregate after preincubation at 37° C. for various times (PCT Publication WO/2008/008358). The disappearance of the initial product can be measured by densitometry analysis, and this analysis supported the spectroscopic data that the mutants had an improved in vitro half-life over the WT and S167A mutant.

Figure 2:
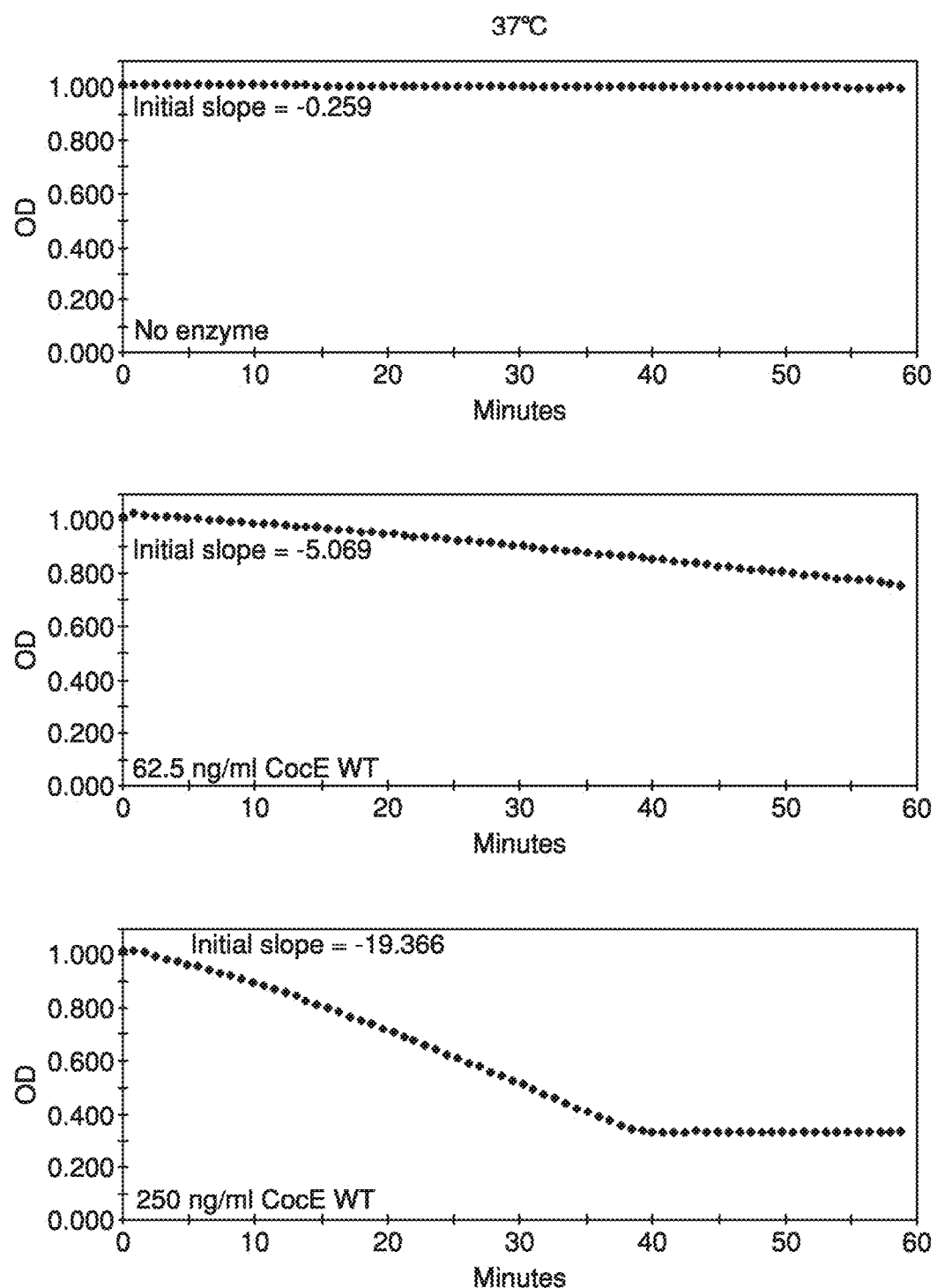
FIG. 2A-FIG. 2C are a series of graphs of cocaine denaturation over time in the presence and absence of CocE.

While pre-incubation at various times indicates that WT CocE had a short half life at 37° C. (5 minutes), it was also observed that if spectrophotometric measurements were run at 37° C., then CocE WT would continue to cleave at a linear rate for more than 60 minutes (FIG. 2, middle) or until the cocaine substrate had been exhausted (FIG. 2, bottom). This suggested that the WT enzyme was being stabilized in the presence of cocaine or it's byproducts.

Figure 3:
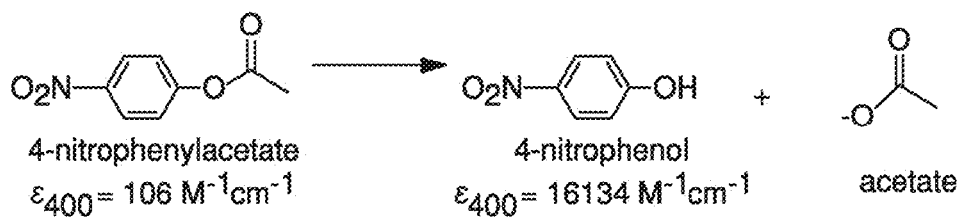
FIG. 3A shows the metabolism of 4-nitrophenyl acetate (4NPA) catalyzed by CocE.
FIG. 3B shows a graph of 4NPA denaturation over time in the absence of CocE.
FIG. 3C shows a graph of 4NPA denaturation over time in the presence of 62.5 ng/ml CocE.
FIG. 3D shows a graph of 4NPA denaturation over time in the presence of 250 ng/ml CocE.
Figure 3:
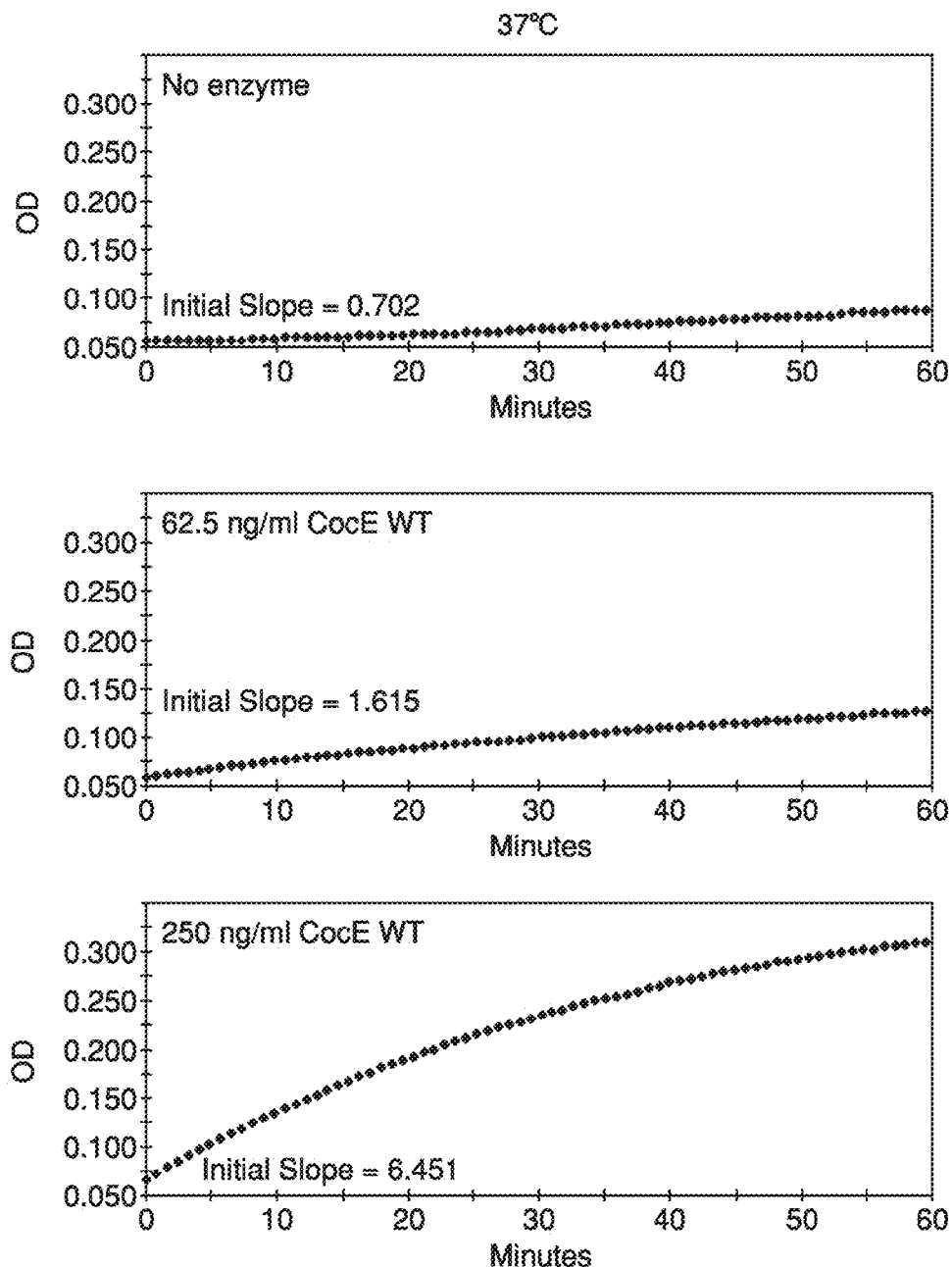

CocE is also able to cleave another substrate, 4-nitrophenyl acetate (FIG. 3). Cleavage is monitored by detection of the appearance of the 4-nitrophenol reaction product, which absorbs at 400 nm. Analysis of cleavage of this substrate at 37° C. shows the product is initially produced quickly, but the reaction slows over time (FIG. 3, middle and bottom). This indicates that the 4-nitrophenyl acetate and products are probably not stabilizing the enzyme, or at least not to the degree that the cocaine reaction is.

Figure 4:
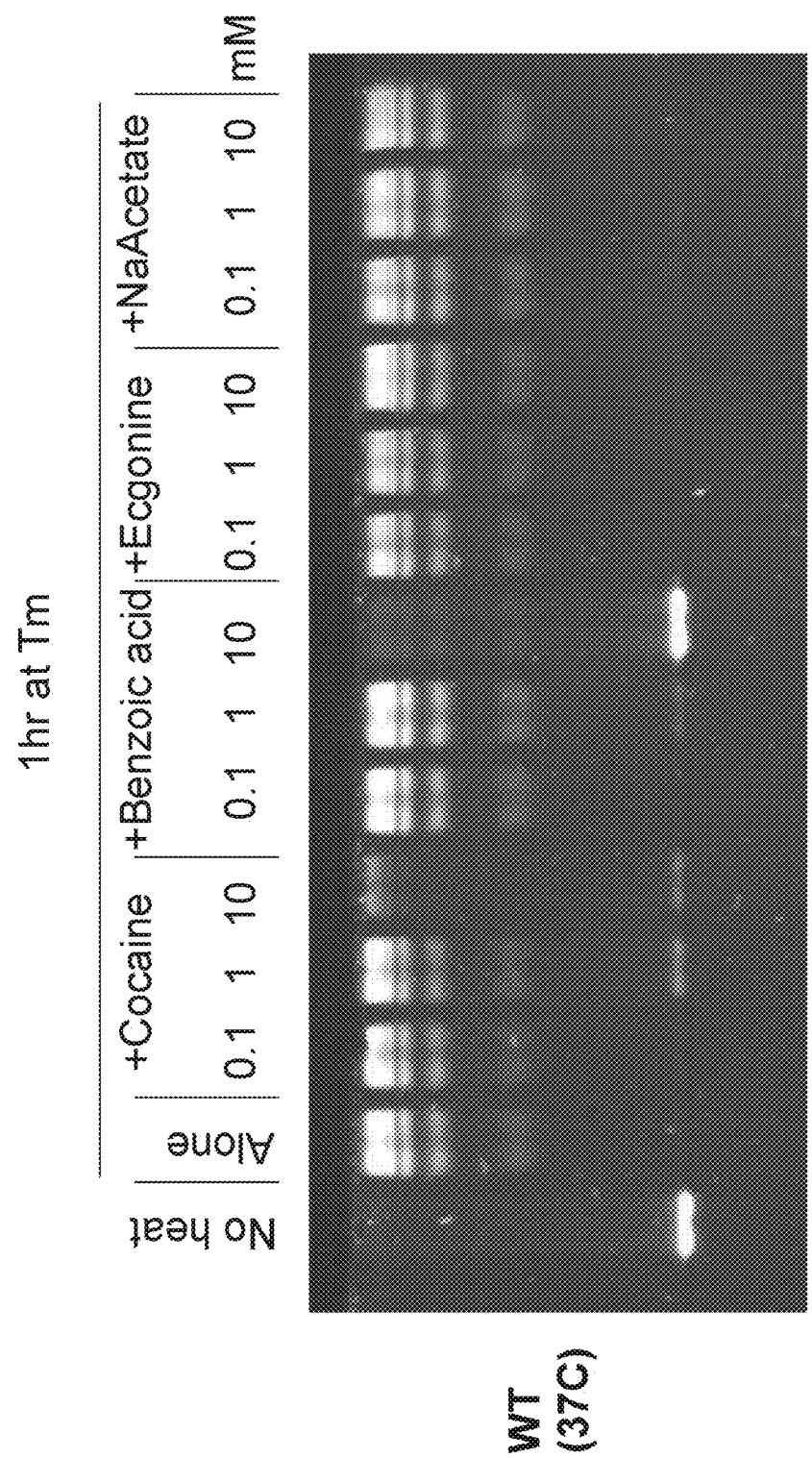
FIG. 4 is a photograph of a nondenaturing gel showing the aggregation of CocE after 1 h incubation under various conditions and in the presence or absence of substrates or products.

To analyze the stabilization of CocE WT by substrates and products, the ability of each compound to inhibit formation of CocE protein aggregates was tested after incubation for 1 hour at 37° C. Both cocaine and benzoic acid inhibited the formation of aggregates at certain concentrations, but ecognine methyl ester and sodium acetate could not (FIG. 4).

Figure 5:
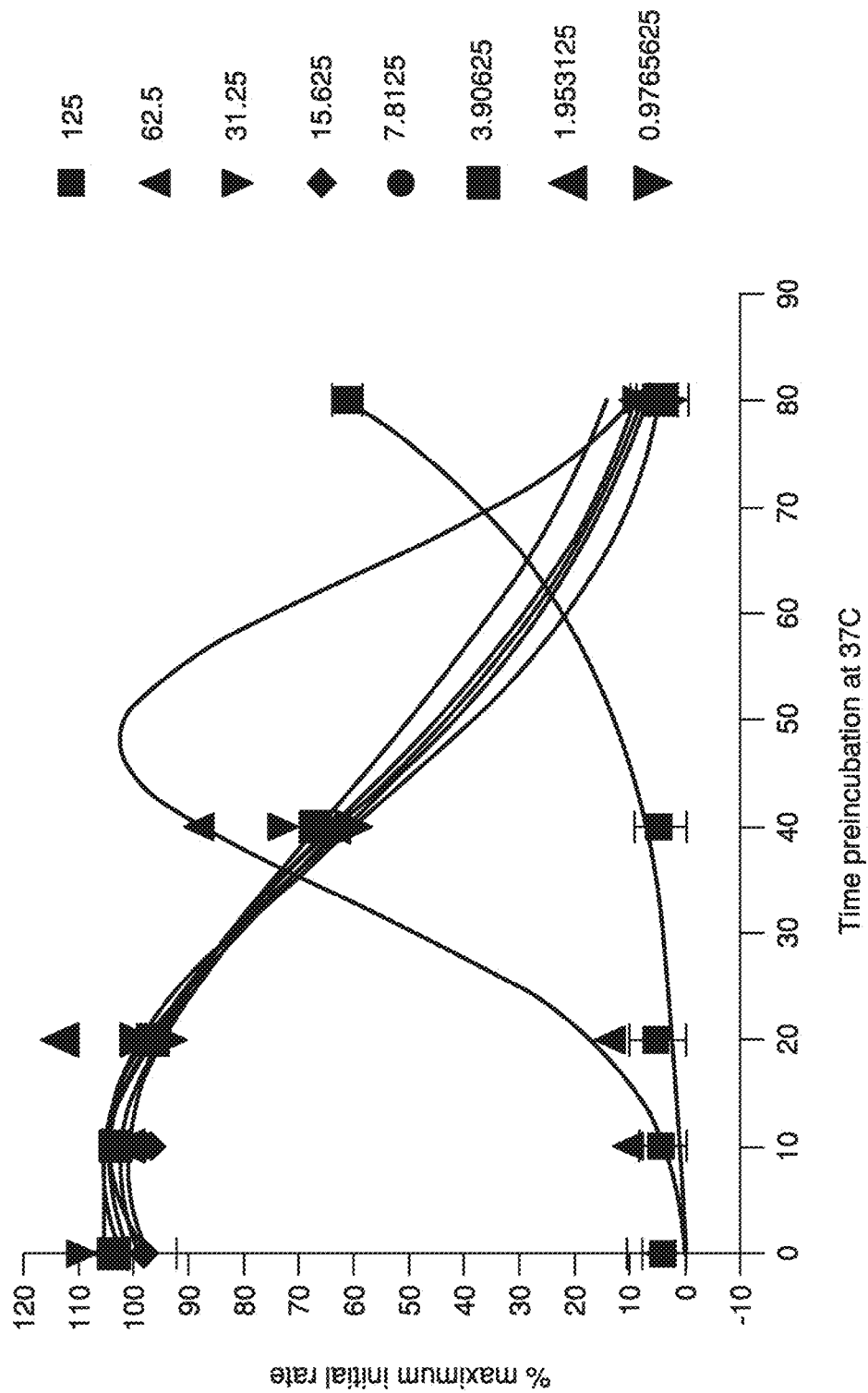
FIG. 5 is a graph of a spectrophotometric analysis of cocaine stabilization during cleavage of 4NPA in the presence of various concentrations of cocaine.

Further spectrophotometric analysis of cocaine stabilization was performed, by analyzing the ability of CocE to cleave 4-nitrophenyl acetate, after preincubation at 37° C. for various times, in the presence of various concentrations of cocaine. Cocaine was found to be a inhibitor of 4-nitrophenyl acetate cleavage at higher concentrations (62.5 and 125 µM)(FIG. 5). Concentrations lower than this were not found to be stabilizing at 37° C. However, preincubation of CocE at the higher concentrations for various times at 37° C. indicated the enzyme was stabilized enough to be able to cleave the 4-nitrophenyl substrate (FIG. 5).

Figure 6:
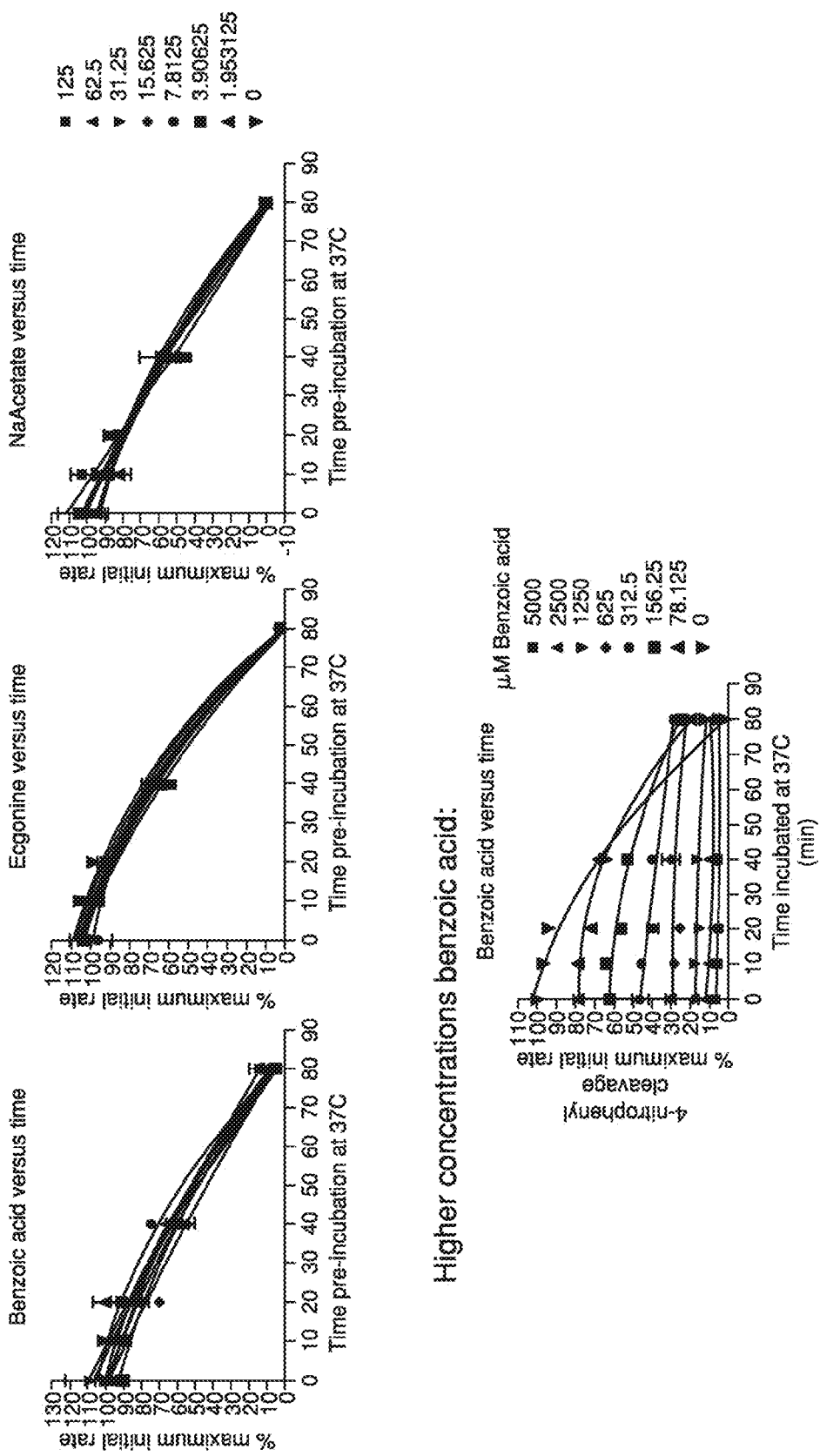
FIG. 6A is a graph showing a kinetic spectrophotometric analysis of benzoic acid stabilization of CocE.
FIG. 6B is a graph showing a kinetic spectrophotometric analysis of ecgonine methyl ester stabilization of CocE.
FIG. 6C is a graph showing a kinetic spectrophotometric analysis of sodium acetate stabilization of CocE.
FIG. 6D is a graph showing a kinetic spectrophotometric analysis of benzoic acid stabilization of CocE at higher concentrations of benzoic acid.

Kinetic spectrophotometric analysis of benzoic acid, ecgonine methyl ester and sodium acetate stabilization of CocE did not reveal any stabilization below 125 µM (FIG. 6). However benzoic acid was found to both inhibit and stabilize at higher concentrations.

Figure 7:
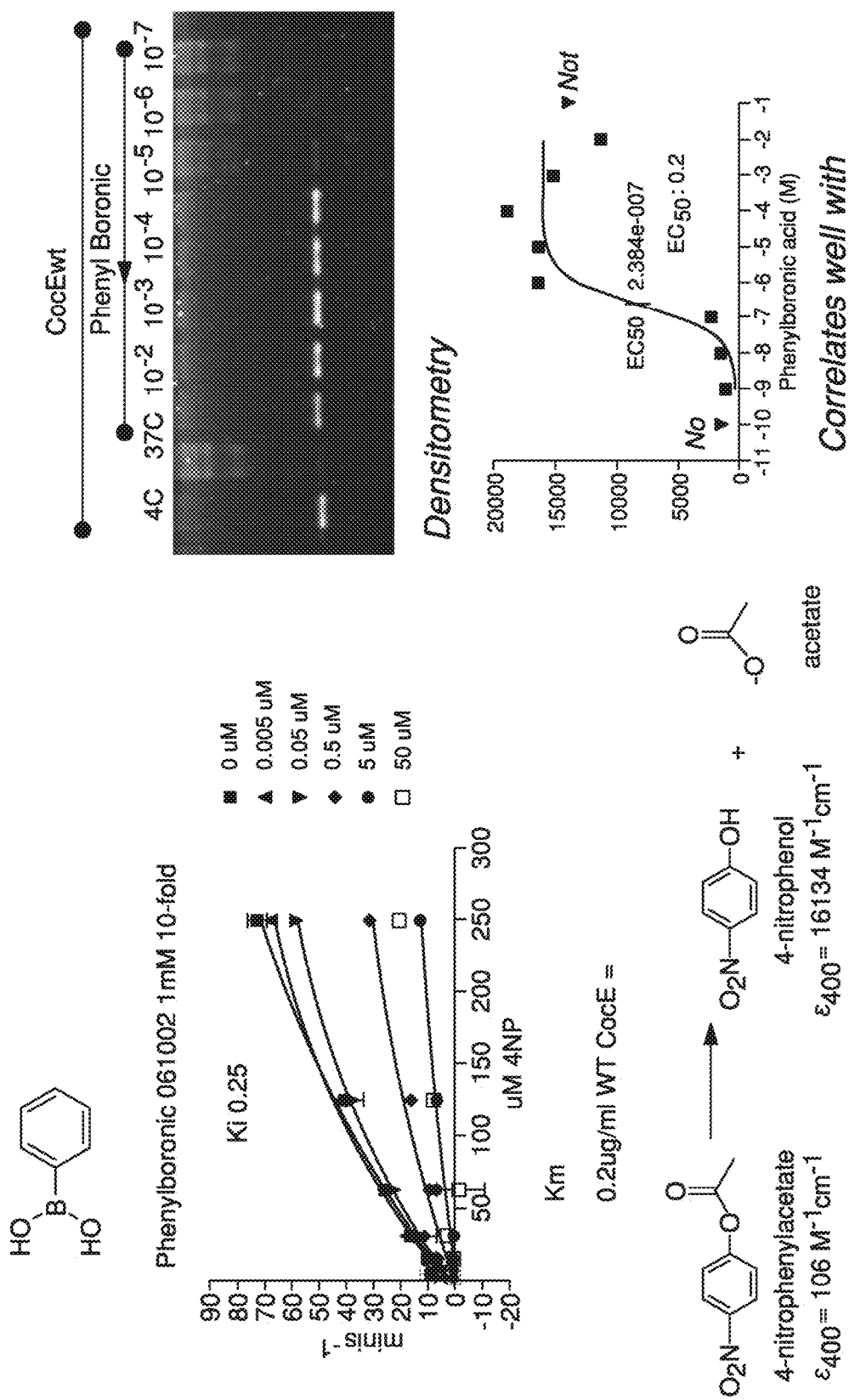
FIG. 7A-FIG. 7E are a series of graphs, chemical structures, a diagram of an enzymatic reaction and a photograph of a nondenaturing gel showing the thermostabilization of CocE by phenylboronic acid (PBA).

To further study CocE stabilization with small molecules, other inhibitors of the CocE cleavage reaction were considered. Phenylboronic acid, an irreversible inhibitor of CocE, which was able to stabilize CocE WT aggregation at 37° C. for 1 hour, with a 50% stabilization concentration of approximately 0.2 µM (FIG. 7).

Figure 8:
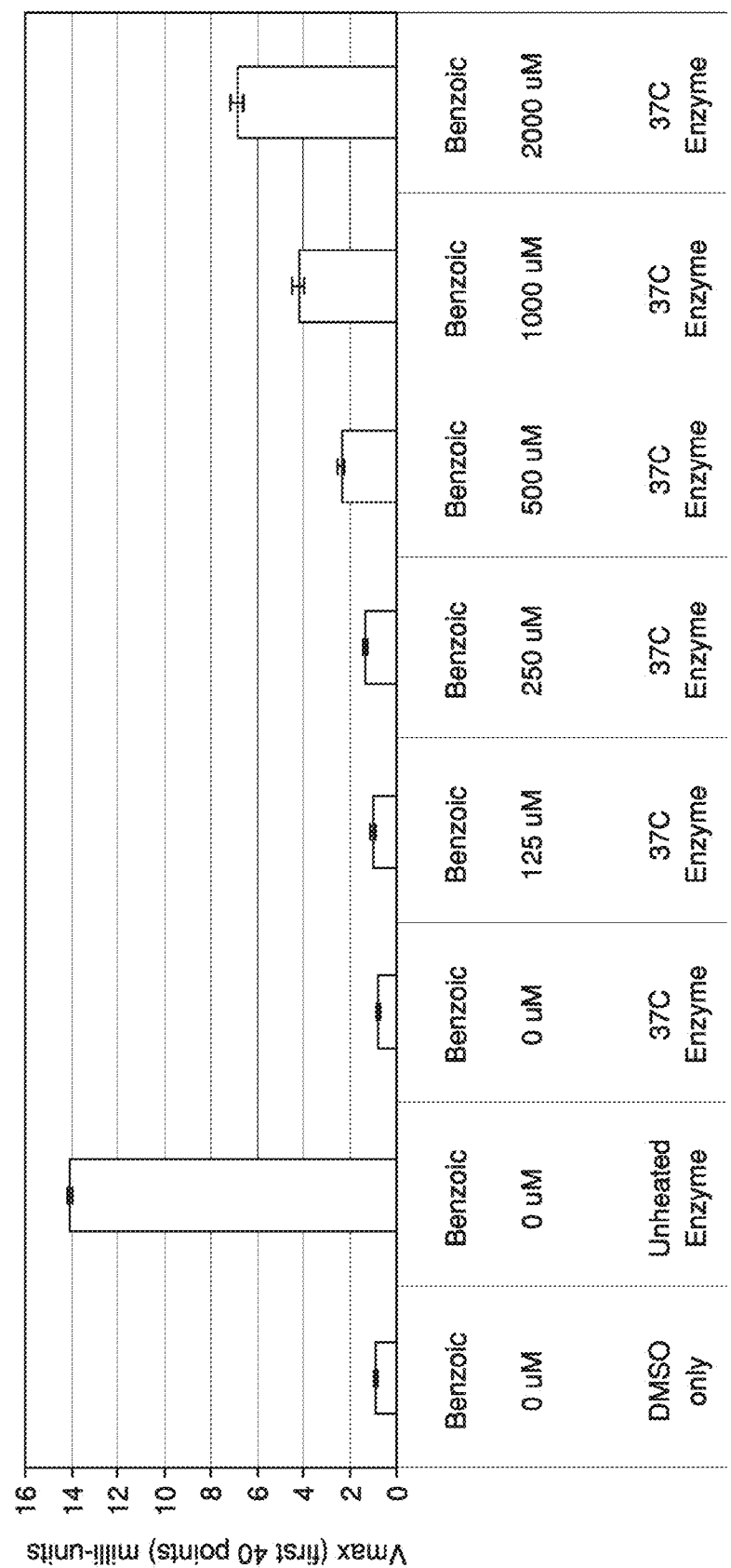
FIG. 8 is a graph showing benzoic acid thermostabilization of CocE.

The data described above indicates that wild-type CocE was able to be stabilized by the addition of substrates, products or inhibitors of the enzyme. However all of these small molecules inhibited enzyme activity to certain degrees. It was evaluated whether there might exist a small molecule that could prevent CocE aggregation, without inhibiting enzyme activity. Such a molecule could be used as a stabilizer in vitro, e.g., during enzyme preparation, and in vivo. An assay was designed to screen a library of 20,000 small molecules for stabilization of CocE. In that assay, the enzyme is mixed with the compounds in a 96-well plate format, and then incubated at 37° C. for one hour. The controls for the assay are usually the compound diluent (e.g., DMSO), unheated enzyme, and enzyme mixed with 2000 µM benzoic acid. After 37° C. incubation, the enzyme/compound mixtures are tested for the ability to cleave 4-nitrophenyl acetate (FIG. 8). Only compounds stabilized would be able to cleave after this incubation period.

Forty compounds were first tested. The compounds were assayed in duplicate with appropriate controls. A duplicate plate (without enzyme) was performed as a negative control, to check for compounds able to cause an increase in 400 nm absorbance in the absence of CocE. Several compounds were found to also increase absorbance at 400 nm. Some were able to do this in the absence of CocE. These were discarded as false positives.

Figure 9:
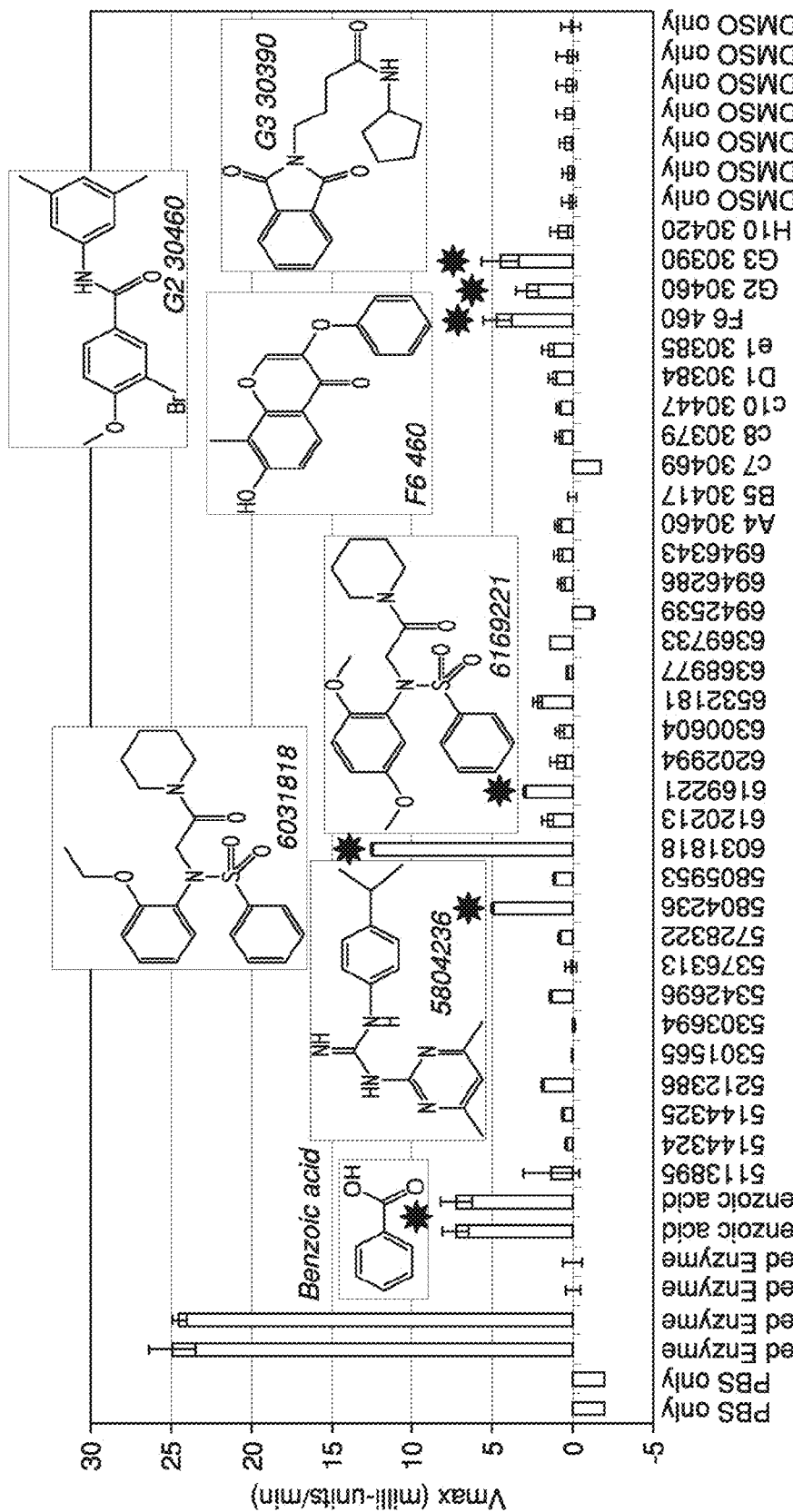
FIG. 9 is a graph showing the results of a screening of 40 compounds for the ability to thermostabilize CocE, along with the chemical structures of the most effective compounds.

FIG. 9 is a plot of the initial rate of 4-nitrophenyl acetate cleavage for all compounds, after the background "no enzyme" cleavage was subtracted. Compounds with significant activity (2 standard deviations above DMSO only controls) are marked with an asterisk and the chemical structures of those compounds are shown.

Figure 10:
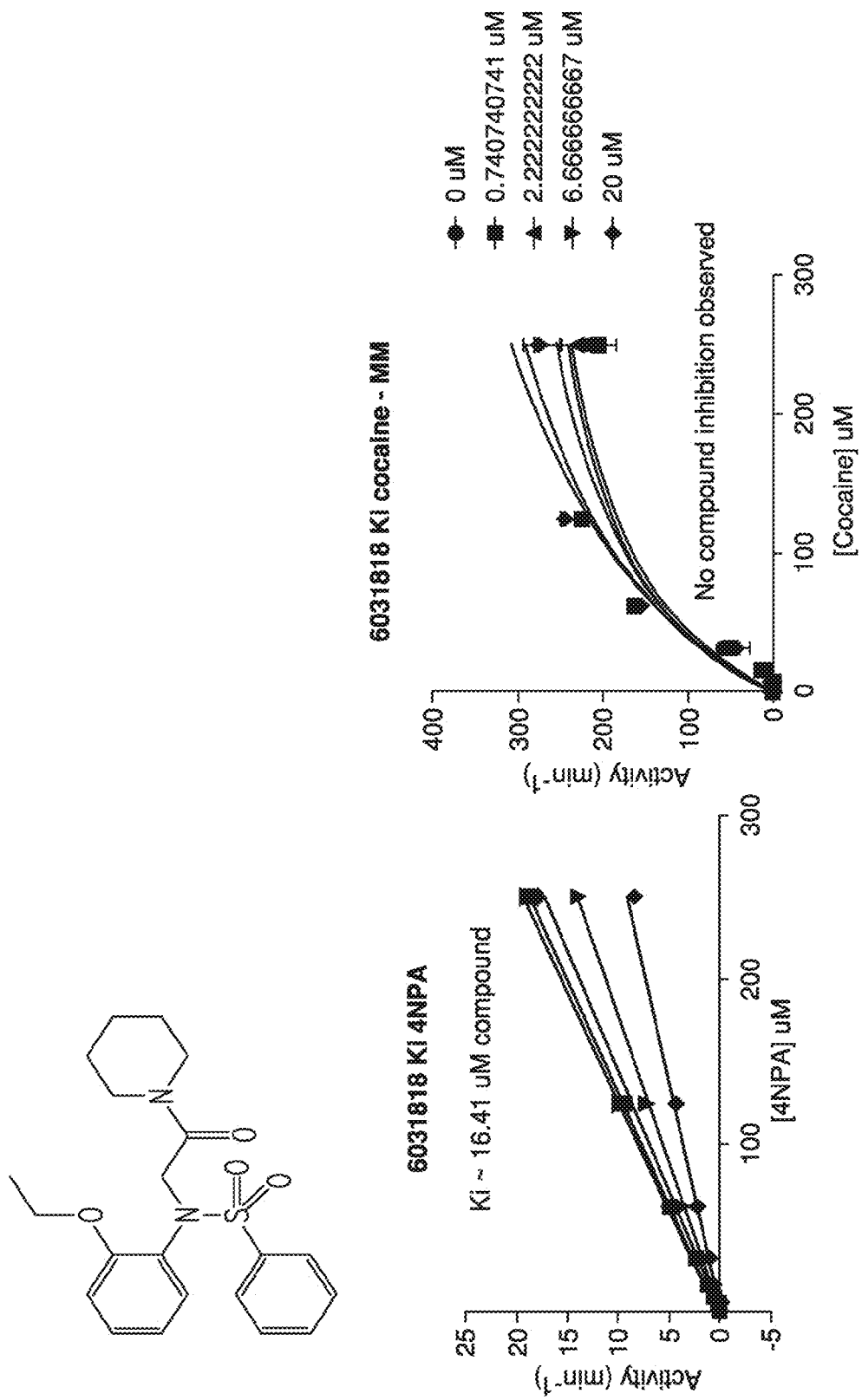
FIG. 10A-FIG. 10C are a chemcial structure and a series of graphs showing the results of studies on the ability of a compound to inhibit CocE.

The most effective compound in the assay was compound 6031818 (FIG. 10). That compound is a weak inhibitor of 4-nitrophenyl acetate cleavage (16 µM; FIG. 10, left graph), and does not inhibit cocaine cleavage at all (FIG. 10, right graph).

Figure 11:
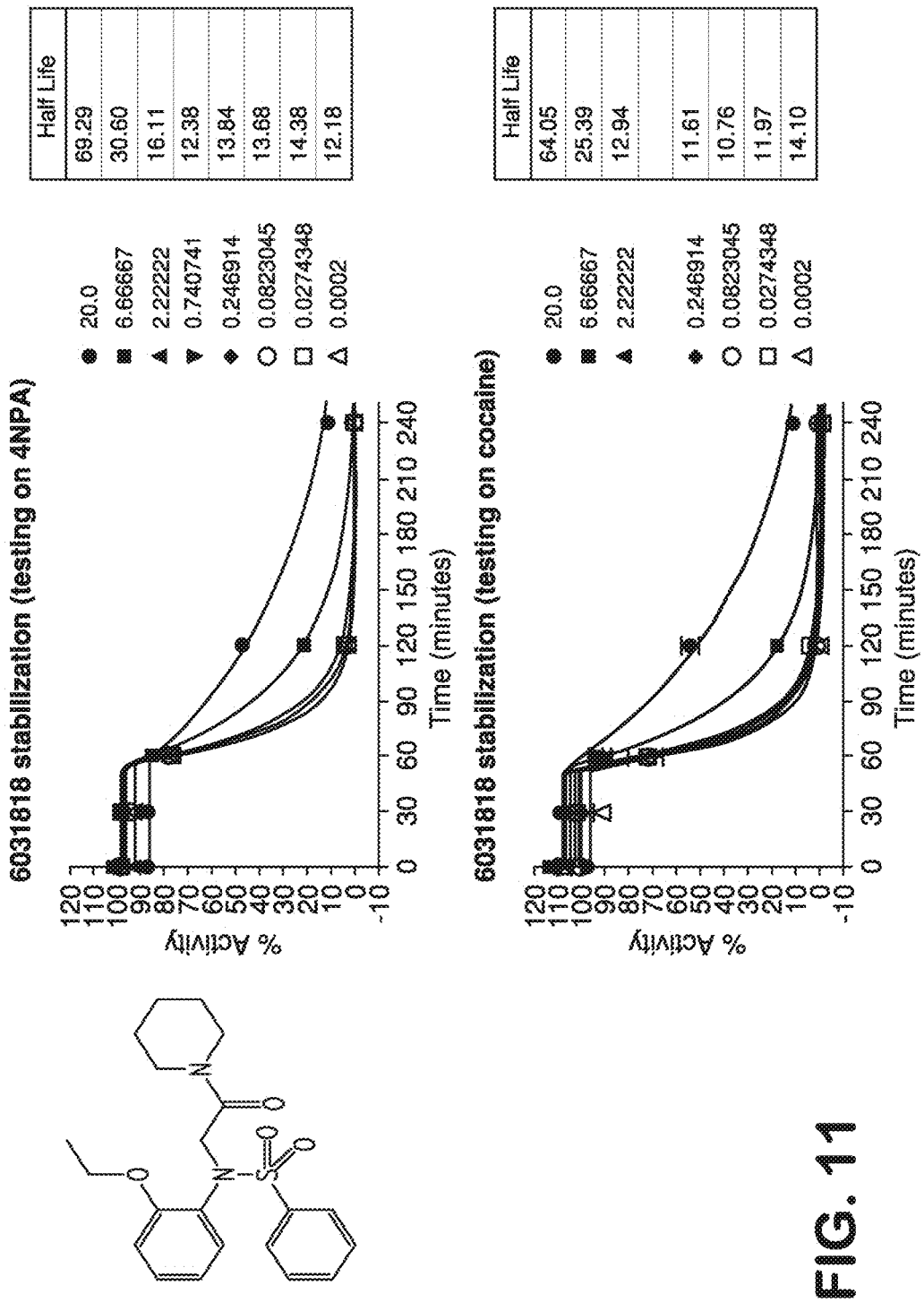
FIG. 11A-FIG. 11C are a chemical structure and a series of graphs showing the ability of that compound to thermostabilize CocE when 4NPA or cocaine are used as substrates.

The stabilization assay in the presence of high enzyme concentrations indicated that enzyme activity begins to drop after 60 minutes at 37° C. (FIG. 11). After that time, 6031818 was able to stabilize the half life of the wild-type enzyme, such that at 20 µM the half life increases from 12-14 minutes to 60-70 minutes.

Figure 12:
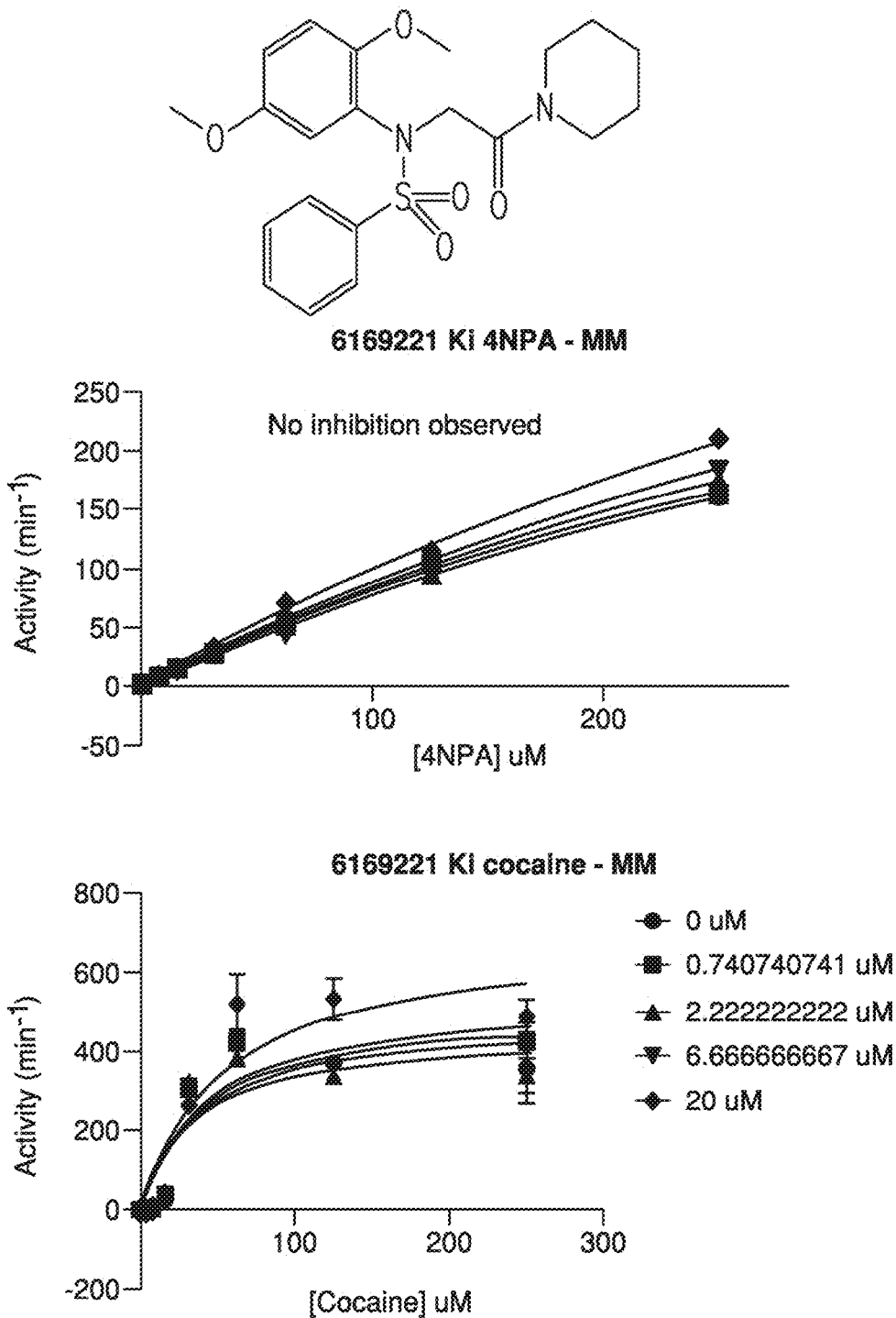
FIG. 12A-FIG. 12C are a chemical structure and a series of graphs and showing results of studies on the ability of that compound to inhibit CocE.
Figure 13:
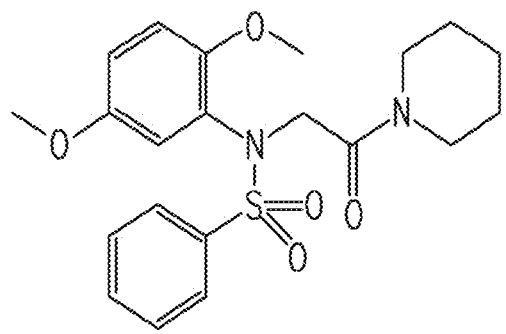
FIG. 13A-FIG. 13C are a chemical structure and a series of graphs showing the ability of that compound to thermostabilize CocE when 4NPA or cocaine are used as substrates.
Figure 13:
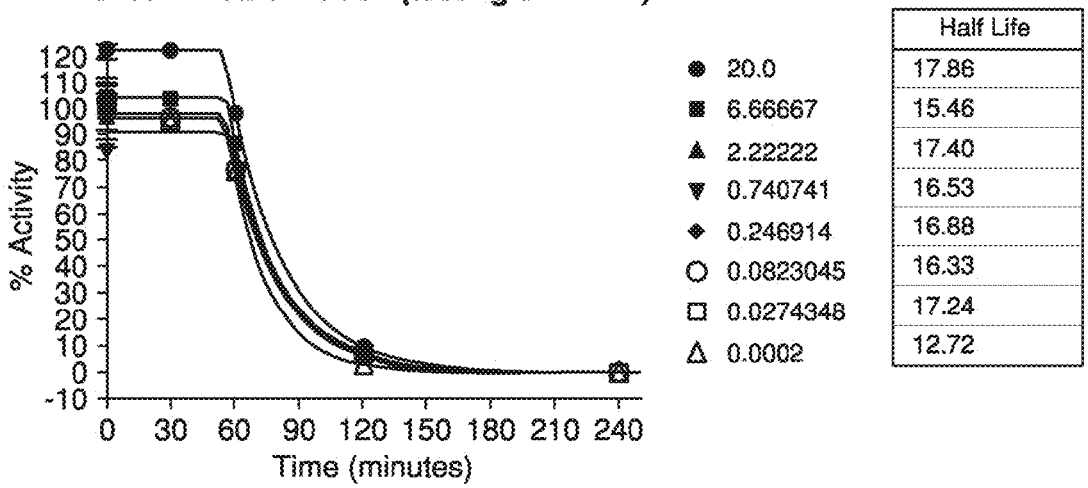
Figure 13:
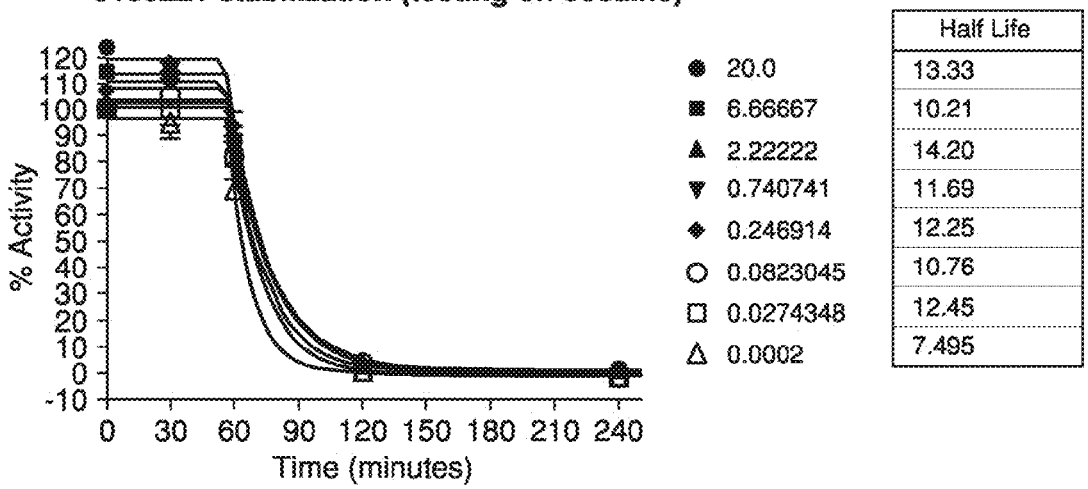

Another effective compound, 6169221, had a very similar structure to 6031818. This compound also did not inhibit 4-nitrophenyl acetate or cocaine substrate cleavage (FIG. 12). The 6169221 compound was only weakly able to stabilize the enzyme, increasing the half life from 7-12 minutes to 13-17 minutes.

Figure 14:
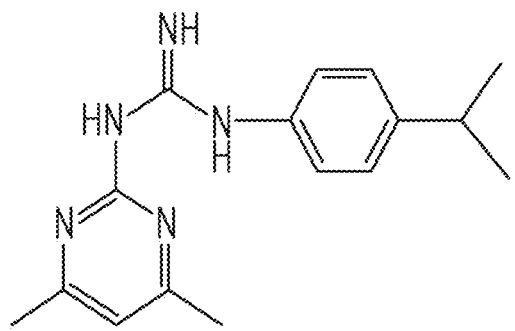
FIG. 14A-FIG. 14C are a chemical structure and a series of graphs showing results of studies on the ability of that compound to inhibit CocE.
Figure 14:
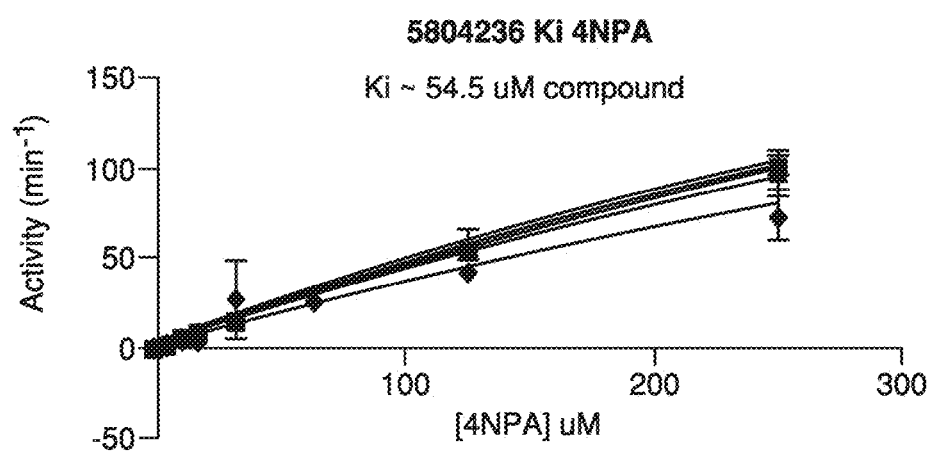
Figure 14:
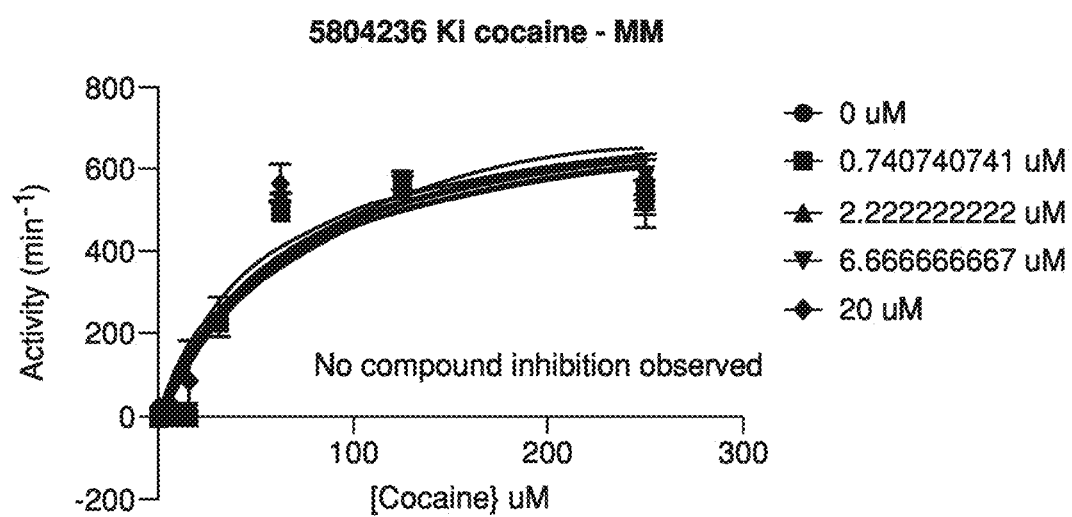
Figure 15:
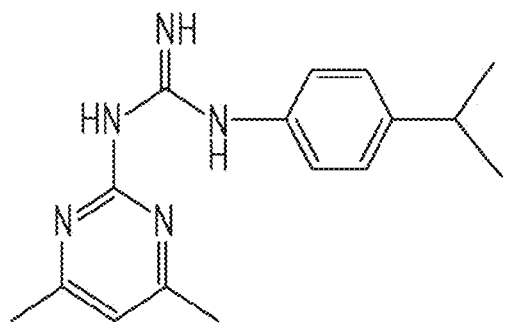
FIG. 15A-FIG. 15C are a chemical structure and a series of graphs showing the ability of that compound to thermostabilize CocE when 4NPA or cocaine are used as substrates.
Figure 15:
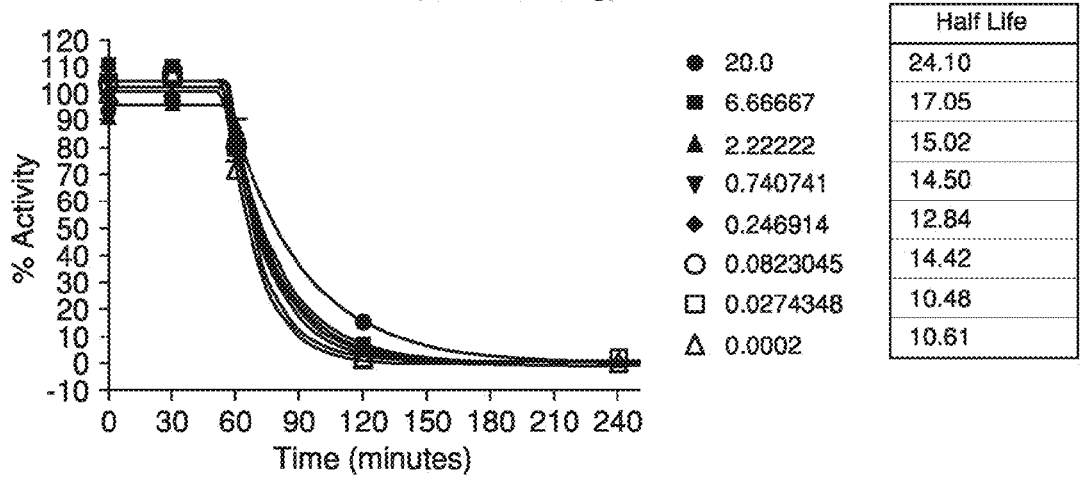
Figure 15:
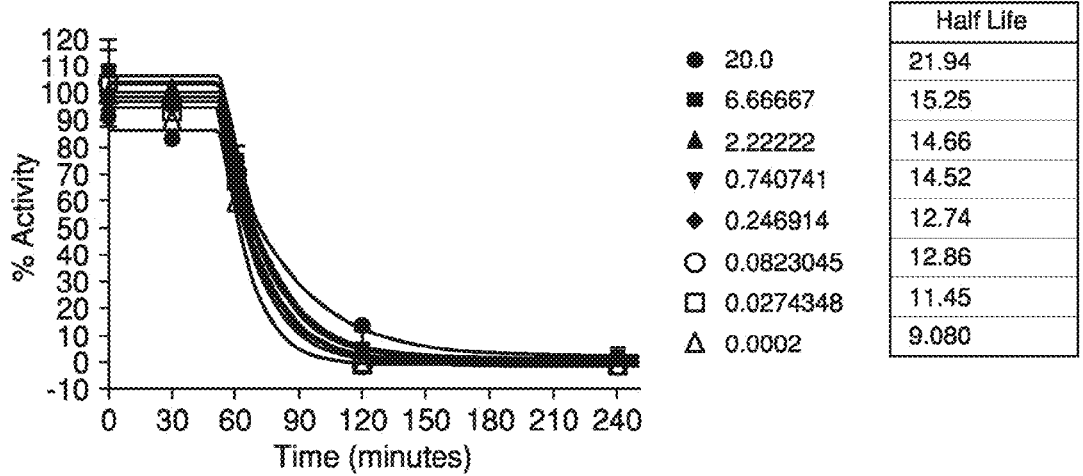

Another thermostabilizing compound is 5804238. That compound also did not inhibit either 4-nitrophenyl acetate or cocaine cleavage (FIG. 14). 5804238 was weakly able to stabilize the enzyme, increasing the half life from 9-10 minutes to 22-25 minutes (FIG. 15).

EXAMPLE 2

Circular Dichroism of Wild Type and Mutant CocE

Figure 16:
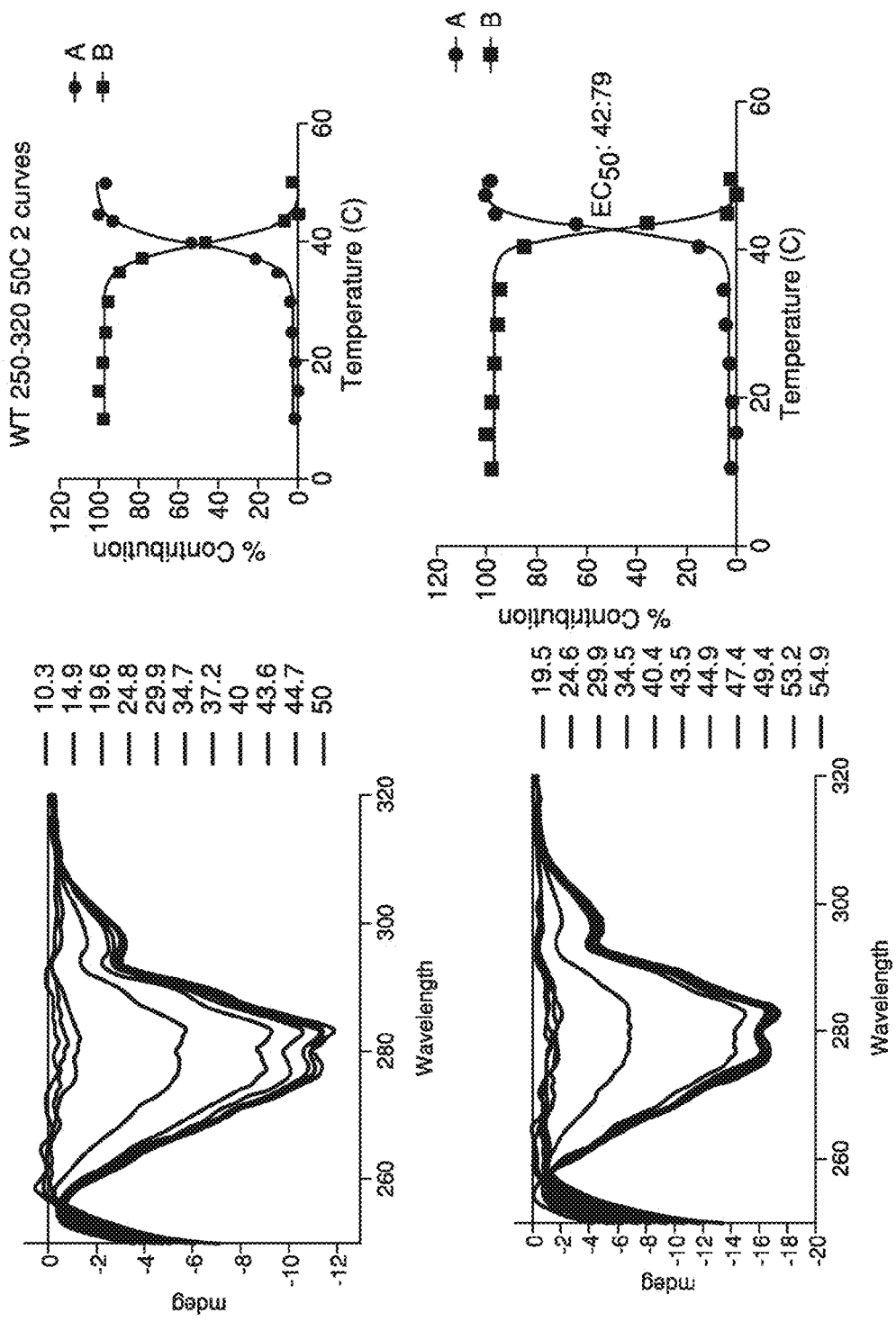
FIG. 16A-FIG. 16D are a series of graphs that further characterize, by circular dichroism, the stability of wild type CocE and mutant T172R.

Further characterization of the stability of wild type (WT) CocE and thermostable mutants was performed through circular dichroism, which detects small changes in protein conformation and structure. Analysis by repeated CD measurements at increasing temperatures allows analysis of the thermodynamics and melting temperature ($T_M$) of the protein, so long as the melting is reversible (i.e. the protein resumes it's original conformation upon cooling). Unfortunately, the melting of CocE WT is not reversible, so true thermodynamics cannot be determined. However CD is still of value in determining the temperature to unfolding. In these assays, CocE WT (FIG. 16, top) melts at approximately 39° C., whereas the T172R mutant (FIG. 16, bottom) melts at ~42° C., showing the thermostability of this mutant conferred at 37° C. is due to a melting temperature 2-3 degrees higher than the WT.

Figure 17:
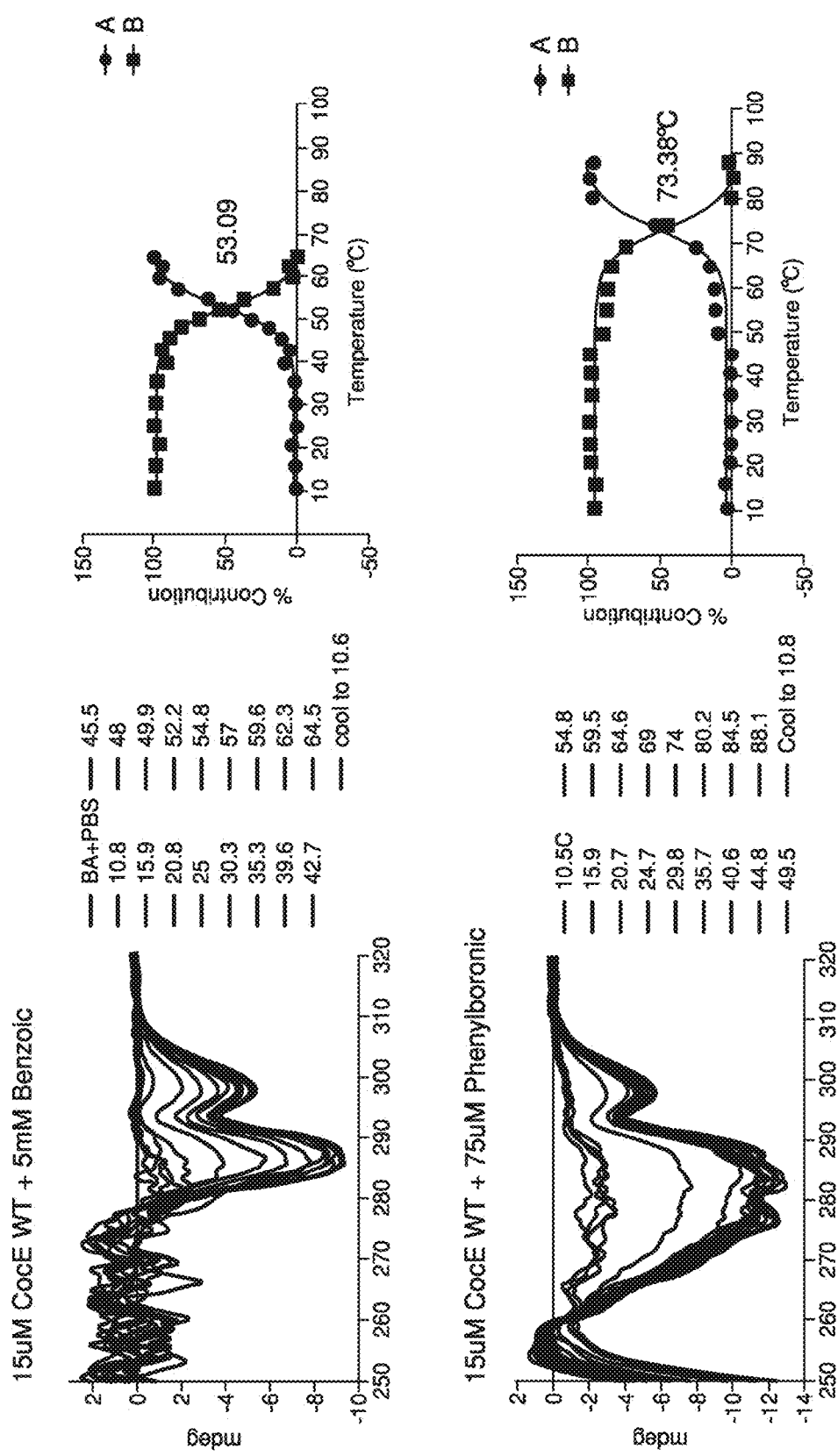
FIG. 17A-FIG. 17D are a series of graphs that further characterize, by circular dichroism, the stability of wild type CocE in the presence of benzoic acid or phenylboronic acid.

WT CocE in the presence of excess benzoic acid (FIG. 17, top) increased the melting temperature of CocE to 53° C., a full 10 degrees higher than the T172R mutant. The benzoic acid molecule at this concentration was slightly spectroscopic, affecting the spectra of the protein, but not the melt. Analysis of WT CocE in the presence of 5x molarity phenylboronic acid (FIG. 17, bottom) increased the melting temperature to 73° C., that is, more than 30 degrees higher than the WT and T172R mutant.

Figure 18:
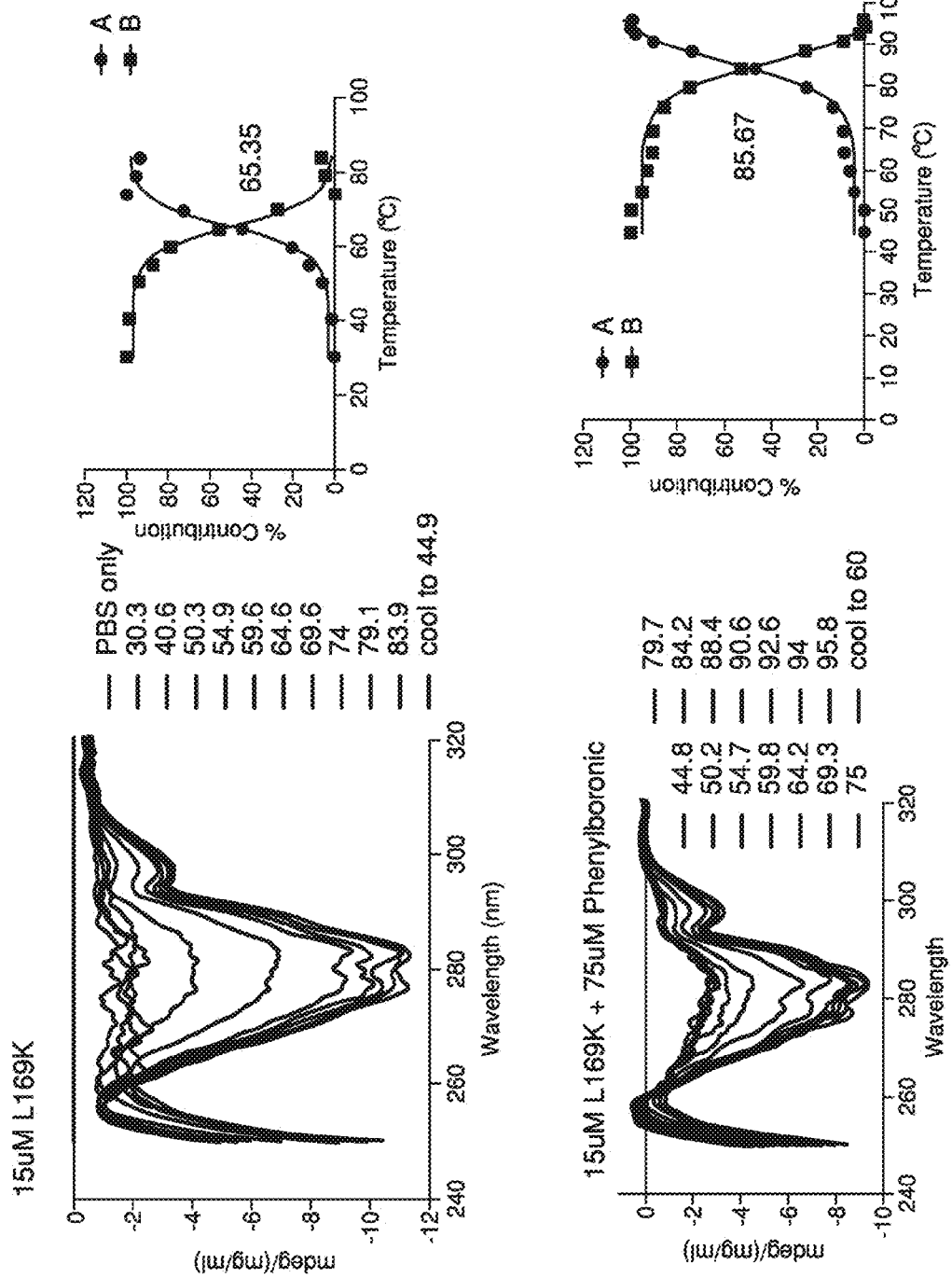
FIG. 18A-FIG. 18D are a series of graphs that further characterize, by circular dichroism, the stability of CocE mutant L169K in the absence or presence of phenylboronic acid.

CD analysis of another CocE mutant, L169K, established a ~65° C. melting temperature alone, and ~85° C. melting temperature in the presence of phenylboronic acid (FIG. 18), i.e. phenylboronic acid conferred an additional 20° C. melting to the already high original melting temperature for L169K.

Figure 19:
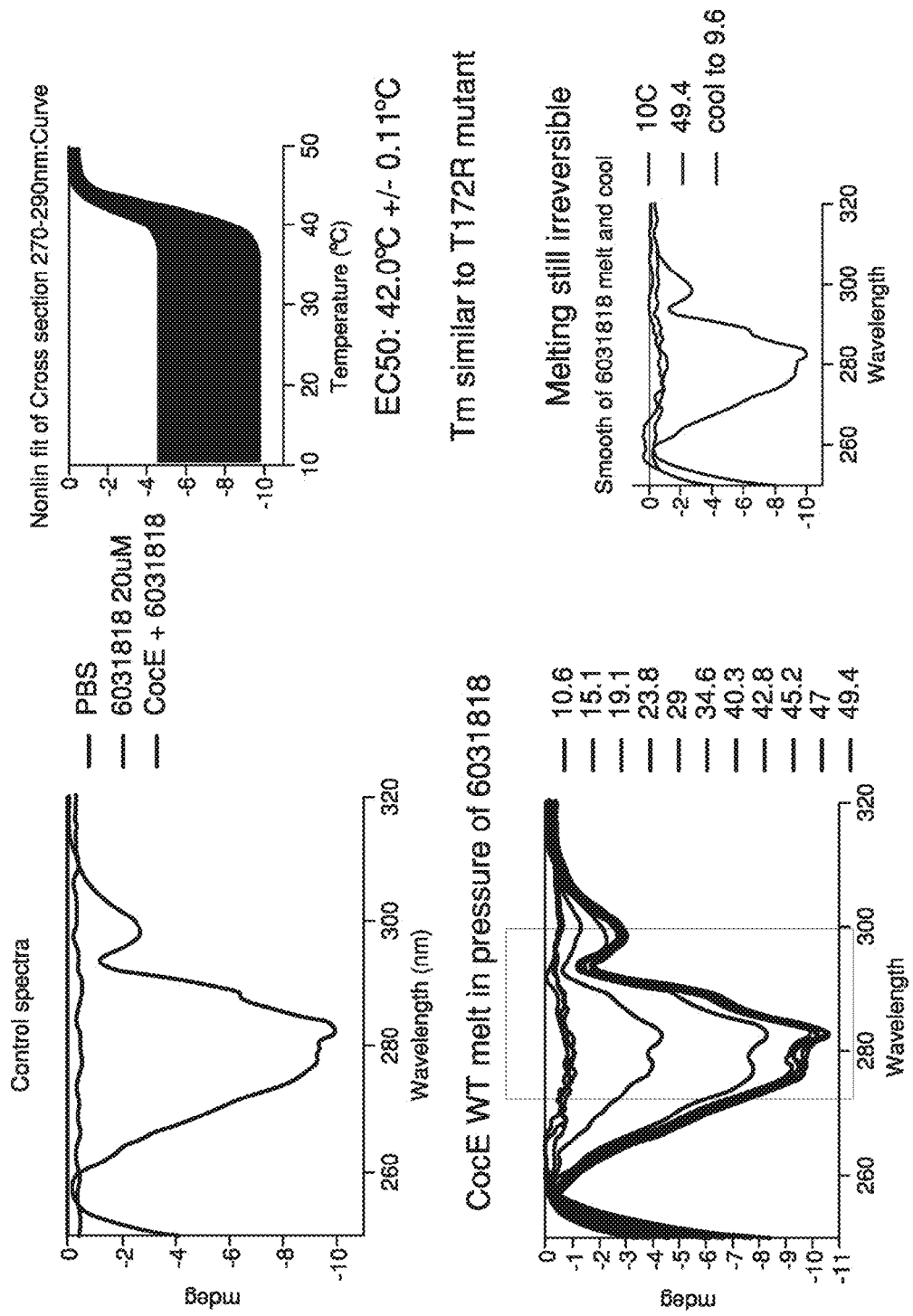
FIG. 19A-FIG. 19D are a series of graphs that further characterize, by circular dichroism, the stability of wild type CocE in the presence or absence of compound 6031818.

CD analysis of CocE WT in the presence of 6031818 established a melting temperature of ~42° C., similar to the T172R mutant (FIG. 19).

EXAMPLE 3

Figure 20:
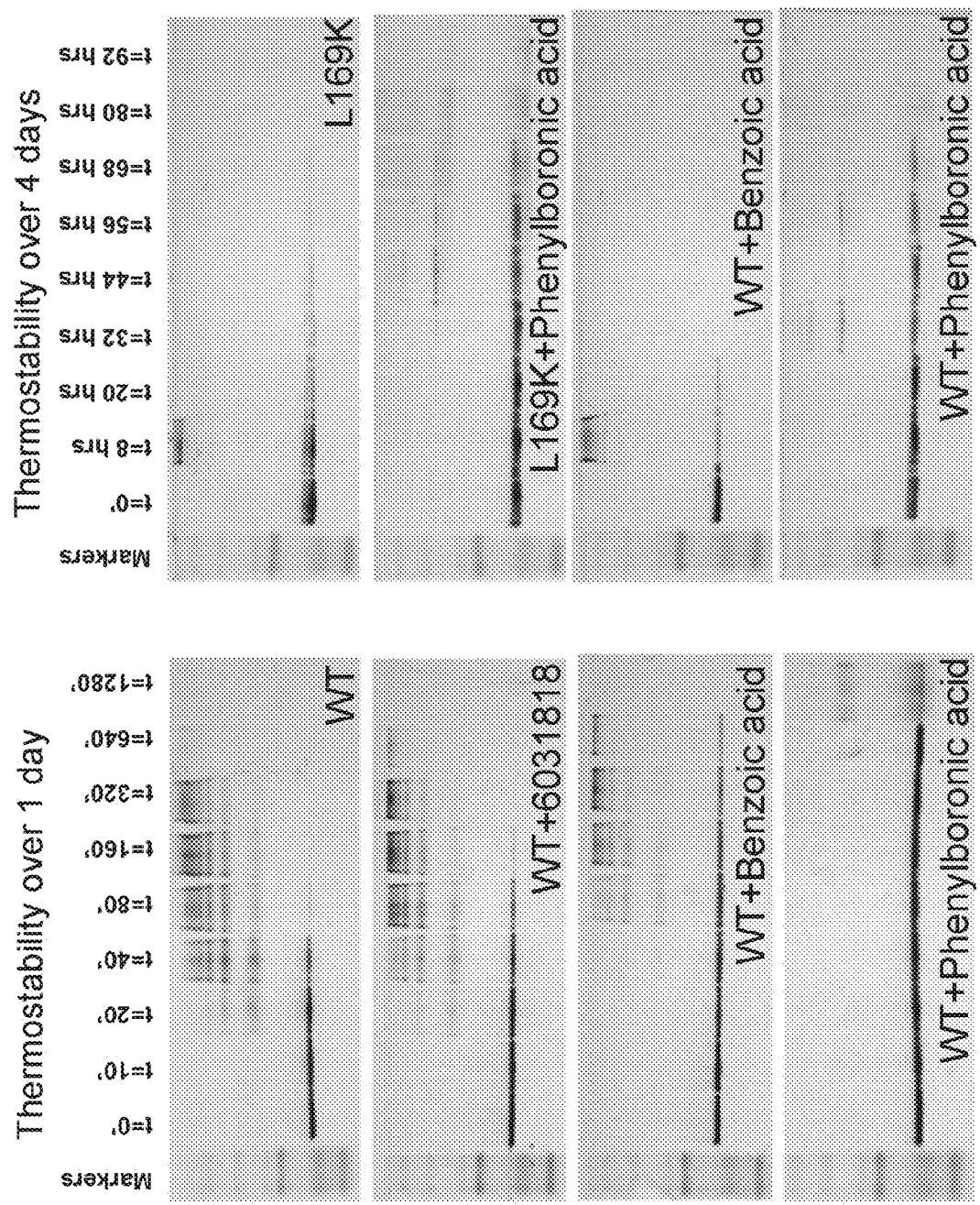
FIG. 20A is a photograph of a non-denaturing gel showing the results of an analysis of wild-type CocE in the presence of various small molecules after incubation at 37° C. for various time points.
FIG. 20B is a photograph of a non-denaturing gel showing the results of an analysis of CocE mutant L169K in the presence of various small molecules after incubation at 37° C. for various time points.
Figure 21:
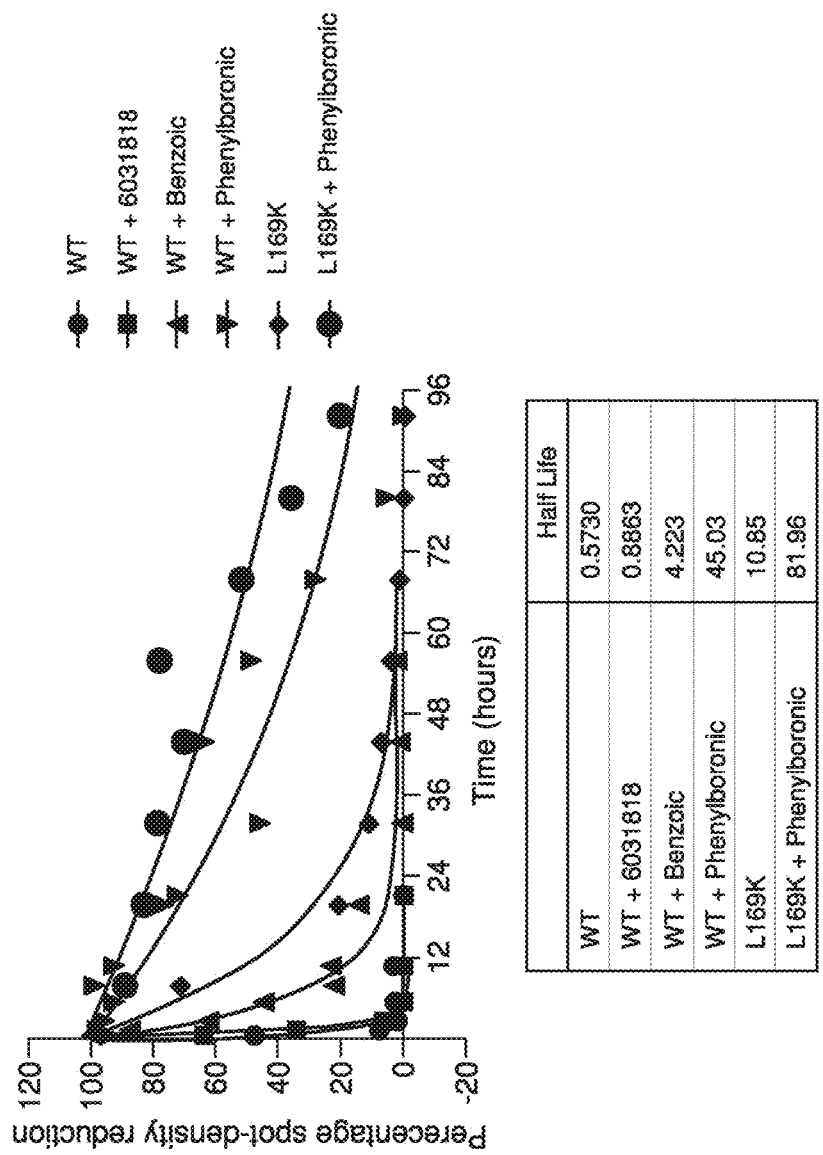
FIG. 21A is a graph showing the results of a spot densitometry half-life analysis of the gels shown in FIG. 20.
FIG. 21B is a table showing the results of a spot densitometry half-life analysis of the gels shown in FIG. 20.

Analysis of Thermostability of Various Compounds with Wild-Type and a Mutant CocE Wild-type CocE or CocE mutant L169K was incubated in the presence of various small molecules at 37° C. for various time points, then run on non-denaturing gels. The results are shown in FIG. 20. Spot densitometry was used to analyze the gels to determine the half-life of the CocE enzymes under these conditions. See FIG. 21. Phenylboronic acid increased the half-life of the CocE the most, followed by benzoic acid. Compound 6041818 increased the half-life of the wild-type enzyme by about 50%.

EXAMPLE 4

Identification of CocE Thermostable Mutants by Structure-Based Analysis

Example Summary

Despite advances in the development of therapeutics that target the dopamine transporter, the identification of therapeutics that combat cocaine abuse and overdose have been less fruitful. More classical approaches to therapeutic development against cocaine abuse and overdose have inherent challenges in that competitive and allosteric inhibitors of cocaine binding to the transporter exhibit similar behavioral effects of cocaine: inhibition of dopamine uptake. The use of cocaine esterase has been developed as a protective therapy against cocaine-induce lethality. The acceleration of enzyme-mediated digestion of systemic cocaine by exogenously added cocaine esterase represents a significant paradigm shift in cocaine abuse therapy. Here the design and generation of significantly more stable enzyme preparations using computational approaches is reported. Evidence from both in vitro and in vivo studies is provided indicating that the modified enzyme displays a prolonged half-life (up to 30-fold) and improved thermostability than the wild-type enzyme. Moreover x-ray crystallographic evidence has been obtained that provide a structural rationale for the improved enzyme stability.

Introduction

Structure-based and computational approaches were utilized to generate mutants of CocE with increased stability at 37° C. The crystal structure of CocE (Larsen et al., 2002) and a combination of molecular modeling, energy minimizations, and molecular dynamics (MD) simulations with the RosettaDesign program (Kirjegian et al., 2005; Kuhlman and Baker, 2000) and AMBER program (Case et al., 2004) were used. The expressed and purified mutants were assessed for their improved intrinsic stability using in vitro assays. Importantly, three out of 36 predicted substitutions exhibited a dramatic improvement in the half-life of the enzyme as assessed by in vitro assays and by the in vivo protection against cocaine-induced lethality. X-ray crystal structures of these mutants were determined in order to investigate their structural basis for improved thermal stability. In each case, the substitutions increase interdomain contacts of the enzyme. The dramatic improvement in stability of mutant CocE in vivo illustrates the promise of both this experimental approach, and the use of CocE in cocaine abuse and addiction.

Materials and Methods

Materials. Cocaine was purchased from Mallinckrodt Inc., St. Louis, Mo. All other reagents are of analytical grade and were obtained from Fisher Biosciences and Sigma-Aldrich Corp.

Design of Thermostable Mutations. Based on the X-ray crystal structure (PDB code 1JU3) of the bacterial cocaine esterase (cocE) (Larson et al., 2002), a complete 3D model of CocE bound to (−)-cocaine was built using energy minimizations and molecular dynamics (MD) simulations encumbered within the AMBER program (Case et al., 2004). To increase the thermostability of CocE, a computational method implemented in RosettaDesign program (Kuhlman and Baker, 2000) was used, which was capable of predicting thermostabilizing mutations within a given fold while minimizing any shift in the backbone that might structurally disrupt the active site structure or quench its flexibility. The method implemented in the RosettaDesign program uses an energy function for evaluating the fitness of a particular sequence for a given fold and a Monte Carlo search algorithm for sampling sequence space. The same method has successfully been used by other researchers to increase thermostability of an enzyme with no reduction in catalytic efficiency (Korkegian et al., 2005; Kuhlman and Baker, 2000). The computational modeling using the RosettaDesign program has allowed the prediction of a set of mutations that can potentially lower the energy and, therefore, increase the higher thermostability of CocE. As the first round of the rational design, the computation was simplified by only considering the possible mutations on the amino acid residues that have a distance of 6-25 Å from cocaine.

Site directed mutagenesis. Point mutations using CocE cDNA cloned in the bacterial expression vector, pET-22b(+), as a template were generated using a modified QuickChange (Stratagene) mutagenesis protocol and single oligonucleotide primers. For generation of double mutants, cDNAs with single point mutations were used as templates for a second round of mutagenesis. All mutants were sequenced in both directions over the entire coding region. Wild-type and CocE mutants were expressed as C-terminally-6× His-tagged proteins in *E. coli* BL-21 Gold (DE3) cells grown at 37° C. Protein expression was induced with 1 mM isopropyl-β-thiogalactopyranoside (IPTG, Fisher) for 12 hours at 18° C.

Purification of Cocaine Esterase and mutants. Cells were pelleted, resuspended in 50 mM Tris pH 8.0, 150 mM NaCl with protease inhibitors (3 μg/ml each of leupeptin and lima bean or soybean trypsin inhibitor) and lysed using a French press (Thermo Fisher Scientific Corp, USA). Wild-type or mutant CocE was enriched using Talon metal affinity chromatography (Clontech Laboratories, Inc, Mountain View Calif.), purified using anion-exchange (Q-Sepharose, GE Healthcare, Piscataway N.J.) chromatography. CocE was eluted from the Q-Sepharose column with 150-450 mM NaCl linear gradient buffers containing 20 mM Hepes pH 8.0, 2 mM $MgCl_2$, 1 mM EDTA and 1 mM DTT. The peak fractions were pooled and concentrated by Centricon-30 (Millipore), snap frozen in liquid nitrogen and stored at −80° C.

Michaelis-Menten kinetics of cocaine hydrolysis. A spectrophotometric real-time assay of cocaine hydrolysis used to monitor the hydrolysis of cocaine (Landry et al., 1993). The initial rates (of decay) were determined by following the change in the intrinsic absorbance of cocaine at 240 nm (6700 $M^1$ $cm^1$)(Xie et al., 1999) using a SpectraMax Plus 384 UV plate reader (Molecular Devices, Sunnyvale, Calif.) using SOFTmax Pro software (Version 3.1.2). The reaction was initiated by adding 100 μL of a 2× enzyme solution (100 mM phosphate buffer, pH 7.4 and 300 mM NaCl) to 100 μL of a 2× cocaine solution (50 μg/mL enzyme, 100 mM Phosphate Buffer, pH 7.4 and 300 mM NaCl). All assays were performed with 100 μM DTT unless indicated otherwise. Final cocaine concentrations were as follows: 125, 62.5, 31.25, 15.63, 7.81, 3.91, 1.95, and 0.977 μM. $V_{max}$ and $K_m$ values were calculated using Prism (GraphPad Software, San Diego). For stability measurements, wild type and mutant enzymes were diluted to 2× concentration and incubated at 37° C. for the times indicated. At the end of each time point, an aliquot was removed and kinetic behavior was observed as outlined above.

In vivo protection against cocaine lethality. Male NIH-Swiss mice (25-32 g) were obtained from Harlan Inc. (Indianapolis, Ind.) and were housed in groups of 6 mice per cage. All mice were allowed ad libitum access to food and water, and were maintained on a 12-h light-dark cycle with lights on at 06.30 AM in a room kept at a temperature of 21-22° C. Experiments were performed in accordance with the Guide for the Care and Use of Laboratory Animals as adopted and promulgated by the National Institutes of Health. The experimental protocols were approved by the University Committee on the Use and Care of Animals at the University of Michigan.

Cocaine-induced toxicity was characterized by the occurrence of lethality, as defined by the cessation of observed movement and respiration. Mice were placed individually in Plexiglas observation chambers (16×28×20 cm high) to be habituated for 15 min before drug administration. Following intra-peritoneal (i.p.) cocaine administration, the mouse was immediately placed individually in the same chamber for observation. The presence or absence of lethality was recorded for 60 min following cocaine administration. The mouse was placed in a small restraint chamber (Outer tube diameter: 30 mm; Inner tube diameter: 24 mm) that left the tail exposed. The tail was cleansed with an alcohol wipe and a 30G1/2 precision glide needle (Fisher Scientific, Pittsburgh, Pa.) was inserted into one of the side veins for infusion. The i.v. injection volume of CocE or CocE mutant was 0.2 mL per mouse. Sterile gauze and pressure were applied to the injection site to staunch the bleeding.

The potency of CocE mutants to protect against cocaine-induced toxicity was assessed following i.v. enzyme administration (0.3 or 1 mg) 1 min prior to administration of several doses of i.p. cocaine (180, 320, 560, and 1000 mg/kg, n=8/dose). Dose-response curves of cocaine-induced lethality in the absence or presence of a single dose of the enzyme were determined to demonstrate the in vivo protective effects of CocE mutants.

The duration of protection against cocaine toxicity provided by CocE and CocE mutants was assessed through monitoring lethality following i.v. enzyme administration (0.1, 0.3, and 1 mg) prior to i.p. cocaine ($LD_{100}$, 180 mg/kg). Lethality was monitored following injection at 1, 5, 10, or 30 min, or 1, 2, 3, 4, 5 hours after enzyme administration. Each treatment used 8 mice to assess the percent of lethality (i.e., protection) in mice pretreated with a single dose of an esterase at a single time point.

In the potency study, a group $LD_{50}$ value was calculated by least-squares regression using the portion of the dose-response curve spanning 50% occurrence of lethality. These values were used to compare the degree of rightward shifts of cocaine's dose-response curve in the absence or presence of the enzyme pretreatment. In the time course study, a time point for duration of protection (i.e., 50% of lethality) was estimated by using each time course curve crossing 50% occurrence of lethality.

Cocaine hydrochloride (Mallinckrodt Inc., St. Louis, Mo.) was dissolved in sterile water and was administered intraperitoneally at a volume of 0.01 mL/g. CocE or CocE mutant was diluted to different concentrations in phosphate-buffered saline and administered intravenously at a volume of 0.2 mL/mouse.

Crystallization and structure determination. Crystals were grown by the hanging drop vapor diffusion method as previously described (Larsen et al., 2002). For harvesting, 2 µL of cryoprotectant (5 mM Tris pH 7.0, 1.5 M ammonium sulfate, 10 mM HEPES pH 7.5, 2 mM $MgCl_2$, 1 mM EDTA, 825 mM NaCl, 25% glycerol and 1 mM DTT where indicated) were added to each hanging drop, and then crystals were transferred to 100% cryoprotectant and flash-frozen in liquid nitrogen. Crystals were harvested within 3 days after tray set-up.

Diffraction intensities were collected at the Advanced Photon Source at beamlines supported by GM/CA- and LS-CAT, and then reduced and scaled using HKL2000 (Otwinowski et al., 1997). Initial phases were from straightforward molecular replacement using previously published structures of CocE (Larsen et al., 2002). REFMAC5 was used for maximum likelihood refinement and model-building and water addition were performed with O and COOT. Unambiguous density was present for all mutated side-chains. Twenty-three total datasets were collected with multiple data sets for each crystal type so the behavior of the H2-H3 loop could be compared. Figures were generated with PyMol [http://www.pymol.org]. Coordinates and structure factors are deposited in the PDB under accession codes 2QAY (T172R), 2QAX (G173Q), 2QAW (T172R/G173Q), 2QAV (L169K), 2QAT (wild-type without ligand) and 2QAU (wild-type with DTT adduct).

Results

Figure 22A:
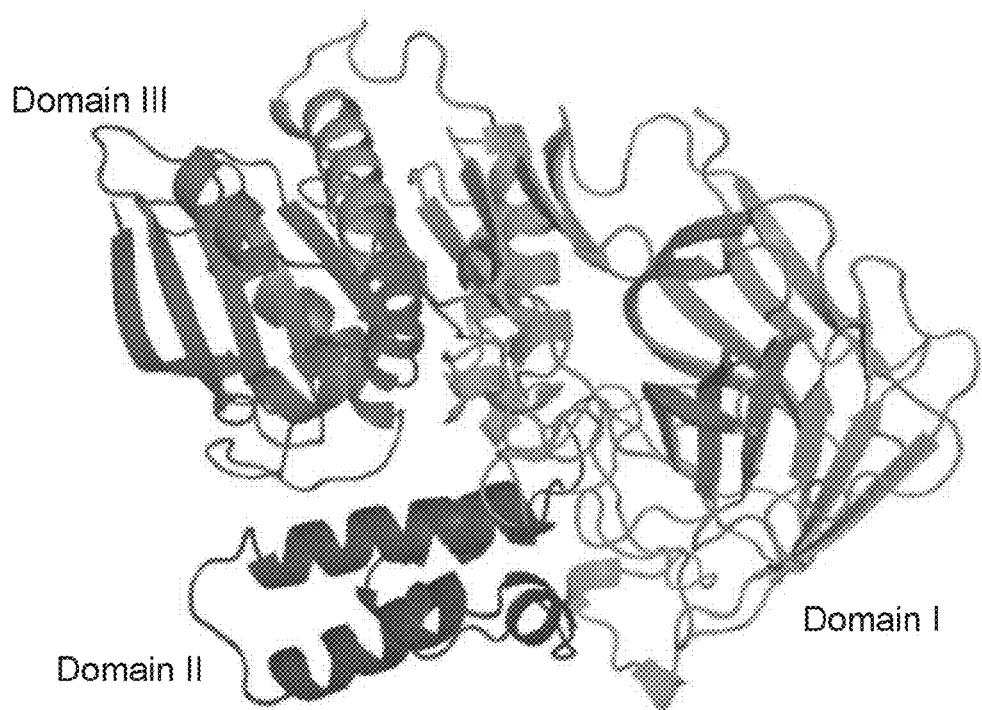
FIG. 22A-FIG. 22B are a series of diagrams showing the structure of cocaine esterase.

Design of thermostable mutations. Cocaine esterase is contains three distinct domains. Domain I (residues 1-144 and 241-354) compose the canonical α/β-hydrolase fold. Domain II (residues 145-240) is a series of 7 α-helices inserted between strands β6-β7 of Domain I. Domain III (355-574) primarily consists of β-sheets and comprises an overall jelly roll-like topology (FIG. 22A). Computational studies were performed, including MD simulation and subsequent energetic analysis to identify substitutions within the 6-25 Å shell surrounding the active site that would stabilize CocE. This structure-and-mechanism-based design of the CocE mutants combined the use of energy minimizations and MD simulations using AMBER (Case et al., 2004) and further modeling studies using the Rosetta Design program (Kuhlman and Baker, 2000). Although CocE is a dimer in solution and in crystals, the modeling was performed with a monomer. The data summarized in Table 1 suggest that the following mutations could thermodynamically stabilize the CocE structure: R41I, N42V, K46A, S56G, T74S, F84Y, L119A, V121D, T122A, Q123E, S140A, L146P, A149S, Y152H, S159A, L163V, V160A, S167A, T172R, G173Q, F189L, A193D, A194R, I218L, W220A, V225I, T254R, V262L, S265A, W285T, A310D, C477T, L508G, K531A, Y532F, and D533S. The positions of the mutations on the CocE structure are shown in FIG. 22A. Each of these single mutations is predicted to stabilize the CocE structure by 2.1 to 4.5 kcal/mol, suggesting that the half-life time of the protein should become about 30 to 1000-fold longer at room temperature (Table 1). To test these predictions, cDNAs encoding the mutations in CocE were expressed in E. coli and the resulting proteins characterized by kinetic and stability assays. Out of the 36 mutants tested, three mutations that clustered around helix 2 of Domain II appeared to improve the enzyme stability at 37° C. without significant reduction in catalytic efficiency, as described below.

TABLE 1

Mutant CocE displaying enhanced stability following incubation at 37° C.

| Mutant | Stability @ 37 ($t_{1/2}$) |
|---|---|
| T122A | No |
| Q123E | No |
| S159A | No |
| S140A | No |
| S167A/W52L | No |
| T172R | ~46 min |
| V121D | No |
| L163V | No |
| F189A | No |
| F189A/T172R | ~40 min (Similar to T172R) |
| C107S | No |
| W220A | No |
| F189L | No |
| A193D | No |
| T172R/A193D | ~40 min (to T172R) |
| G173Q | ~25 min |
| T254R | No |
| N42V | No |
| T172R/G173Q | ~326 min |
| G171Q/T172R/G173Q | No |
| G171A | No |
| G173A | No |
| wt-I175-G-D185 | No |
| wt-T176-G-G-D185 | No |
| T172R/G173Q-I175-G-D185 | |
| T172R/G173Q-I175-G-G-A186 | ~75 min |
| T172R/G173Q-T176-G-G-D185 | ~75 min |
| S177Q | No |
| D45R | No |
| F47R | No |
| L169K | ~274 min |
| L174R | No |
| A181K | No |
| S179R | No |
| F189K | 25 min |
| V190K | No |
| A194K | No |
| R182K | No |

$t_{1/2}$ were determined by preincubation of the enzyme at 37° C. for varying times. Activity measurements were determined at RT (25° C.). Mutant enzymes with $t_{1/2}$ of 12 min (i.e. the $t_{1/2}$ of wildtype [wt] CocE) or less were considered not thermally stable. This Table is also in WO/2008/008358.

Figure 22B:
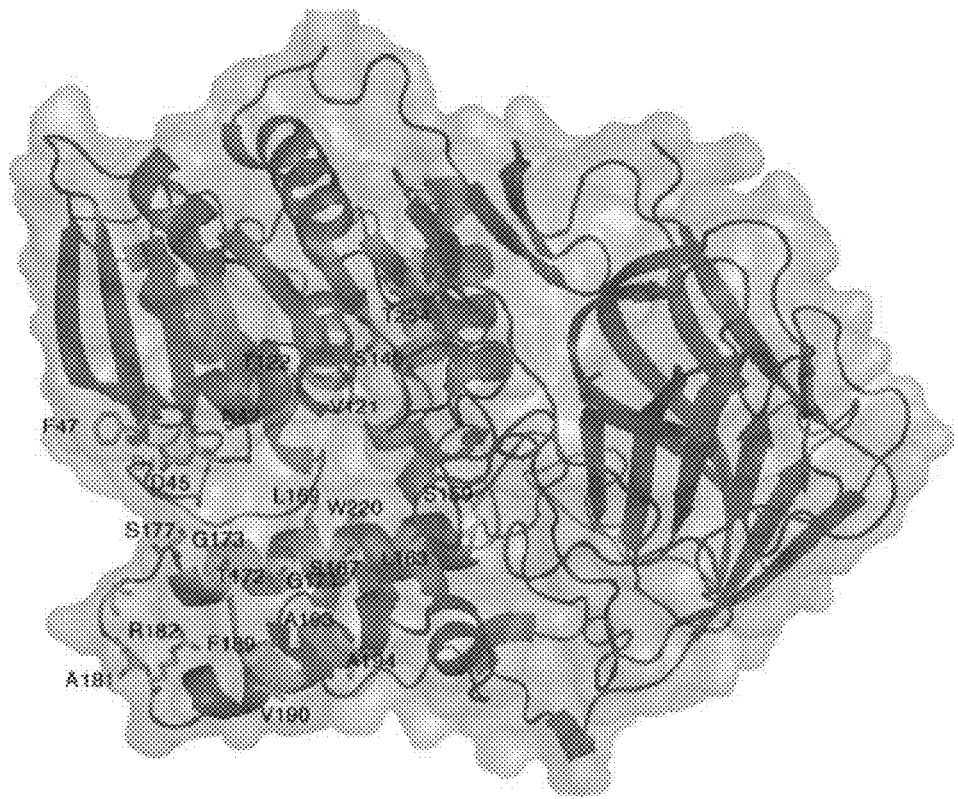
Figure 23:
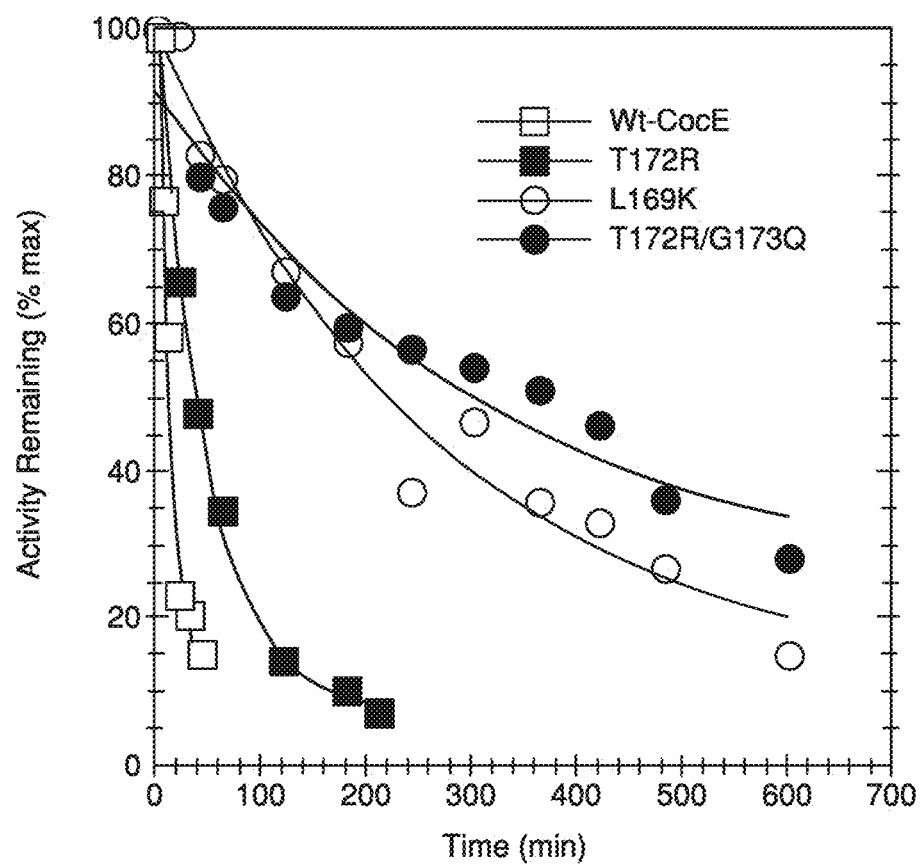
FIG. 23 is a graph showing the decay in CocE activity at 37° C. 50 ng/ml wild-type CocE and the mutants were incubated at 37° C. and activity measured (Xie et al., 1999) over time. Half-lives were measured from resulting curves. Wild-type CocE, T172R, L169K and T172R/G173Q showed 12 min, 46 min, 274 min and 326 min half-lives, respectively.
Figure 24:
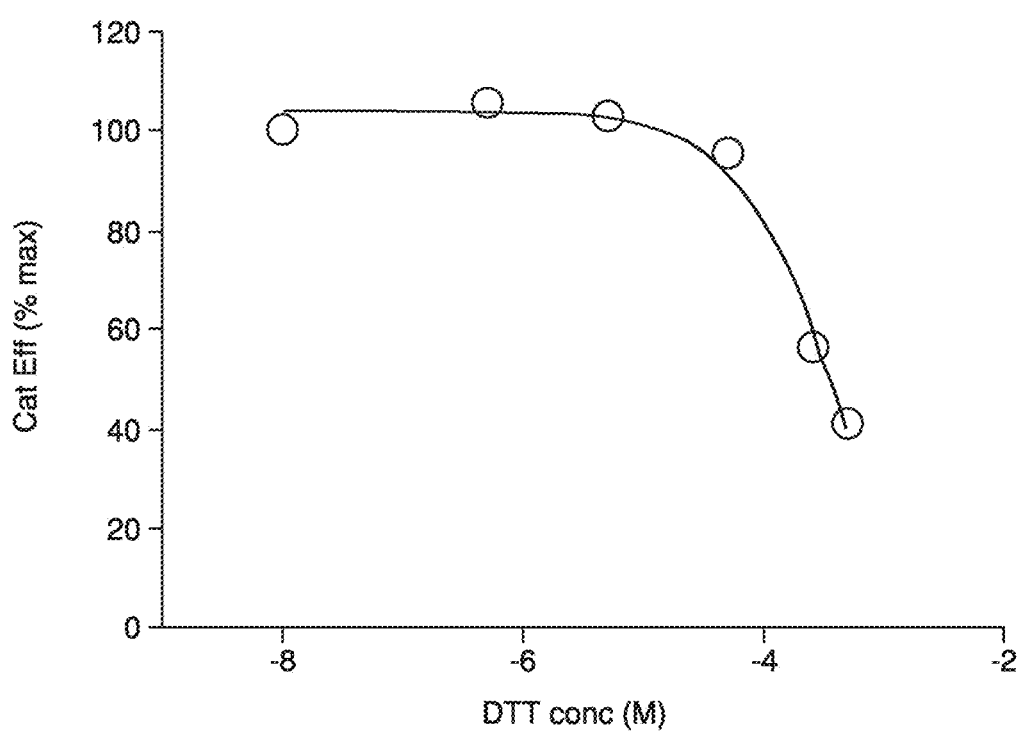
FIG. 24 is a graph showing that DTT inhibits wt-CocE in a concentration-dependent manner with an $IC_{50}$~390 µM.
Figure 25:
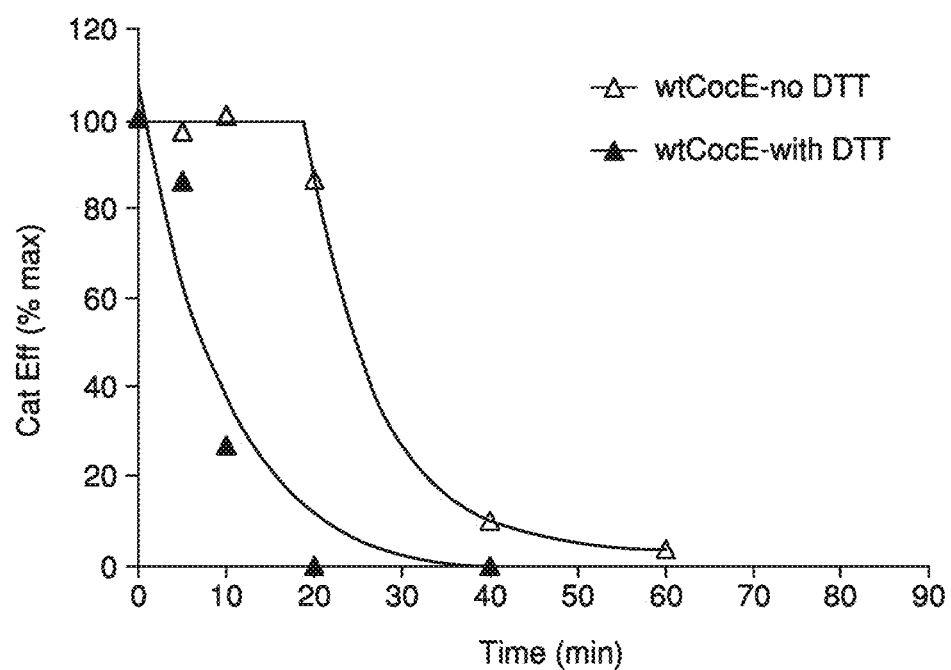
FIG. 25 is a graph showing that the presence of DTT (10 mM) shortens the in vitro $\tau_{inact}$ in wt-CocE.

In vitro kinetic assays. To assess the enzymatic activity of wt and mutant CocE, the hydrolysis of cocaine was directly measured at 37° C. using a spectrophotometic assay (Xie et al., 1999). Initial rates were then used to determine Michaelis-Menten parameters. To assess thermal stability, enzyme preparations were preincubated at 37° C. for various lengths of time, prior to measurement of residual activities (Table 1 and FIG. 23). Inactivation at 37° C. occurs in a time-dependent manner decay. In the absence of DTT, preincubation of wt-CocE at 37° C. decreases enzyme activity exponentially with a half-time of inactivation, $\tau_{inact}$, approximately 25 min. Three out of 36 of the predicted mutants increased the enzymatic stability of CocE: T172R ($\tau_{inact}$=46 min), G173Q ($\tau_{inact}$=35 min; data not shown), and L169K ($\tau_{inact}$~274 min). While T172R and G173Q mutants did not appear to deleteriously effect the enzyme's catalytic efficiency ($k_{cat}$~1×10$^8$ and 2×10$^8$, respectively), the $k_{cat}$ of L169K was diminished, largely as a result of ~5 fold increase in its $K_m$ for cocaine esterase (Table 2). Interestingly, the mutants that appear to display significant stability at 37° C. all reside on helix 2 of Domain II (FIG. 22B). Domain II is also located near to the active site and may, at least in the case of L169K, account for the effects on $k_{cat}$. Also noteworthy is the observation that incubating the enzyme with DTT appears to accelerate the decay for the wild-type enzyme, but not T172R/G173Q and L169K (FIG. 24). It was also determined that DTT can inhibit cocaine hydrolysis with a $K_i$~380 µM (FIG. 25) in a manner that appears to be mixed competitive and non-competitive (not shown). No effect of DTT was observed when combining the mutations appears to further enhance enzyme stability at 37° C. (not shown).

TABLE 2

Kinetic behavior of wild-type and redesigned CocE mutants.

| Enzyme | $t_{1/2}$ (min) | $K_{cat}$(mol · $s^{-1}$ · $mol^{-1}$) | $K_m$(M) | Catalytic Efficiency, $K_{cat}/K_m$ ($s^{-1}$) |
|---|---|---|---|---|
| wt-CocE | 12.2 | 2323 | 0.021 | 1.11E+08 |
| T172R | 46.8 | 2502 | 0.024 | 1.05E+08 |
| T172R/G173Q | 326 | 2247 | 0.024 | 9.40E+07 |
| L169K | 274 | 3104 | 0.105 | 2.90E+07 |

The metabolism of cocaine by purified preparations of wt-CocE, T172R, T172R/G173Q or L169K was measured as described in the Methods Section. The Michaelis constant, $K_M$, and $K_{cat}$ were estimated using Prism (Graphpad, San Diego, CA).

The activity of T172R/G173Q, while still sensitive to incubation at 37° C. displays an enhanced stability and decays $\tau_{inact}$~326 min. However, the observed catalytic activity plateaus to approximately 35% of its maximal catalytic rate (i.e. at t=10 hours). This inactivation profile was qualitatively and quantitatively different than the behavior of the T172R and G173Q single mutants and wt-CocE, but similar to that of L169K. Surprisingly, the triple mutant (L169K/G173Q/T172R) did not display an enhanced stabilization (data not shown).

Figure 26:
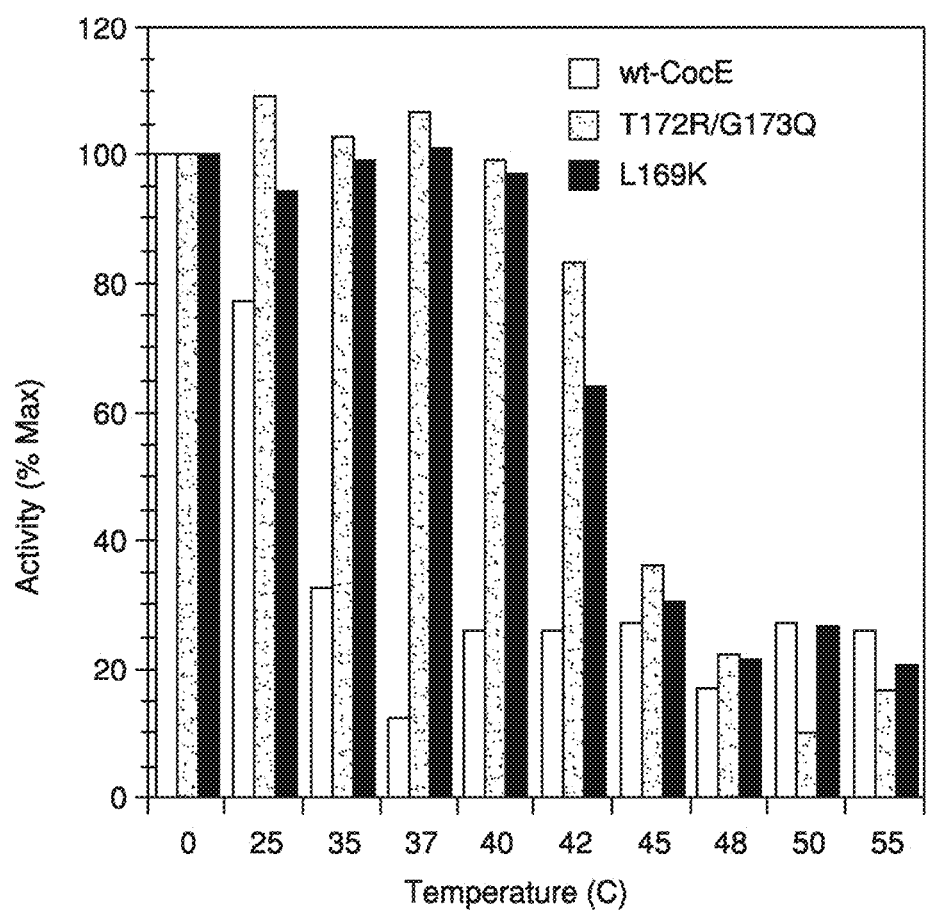
FIG. 26 is a graph showing temperature-dependent decay in esterase activity. 50 ng/ml wild-type CocE and the mutants were pre-incubated for 30 min at temperatures indicated (° C.) and activity measured (Xie et al., 1999). The activity of each mutant remaining (as a percentage of the maximal activity, $V_{max}$, without preincubation) following pre-incubation are illustrated. Wild-type CocE (open bars) appears to inactivate between 30-35° C. whereas T172R/G173Q (shaded bars) and L169K (solid) both display enhance thermal stability (inactivation at 40-45° C.).

To test whether the improved enzymatic stability at 37° C. represents improved thermal stability of the protein fold, the capacity of the CocE at progressively higher temperatures were assessed (FIG. 26). The activity of wt CocE plummets precipitously after 30 min at approximately 30-35° C. Both L169K and T172R/G173Q each are inactivated at a higher temperature (40-45° C.). Circular dichroism analysis (near UV analysis) at varying temperatures, comparing wt-CocE and T172R/G173Q have melting temperatures in concordance with the loss of catalytic activity.

Figure 27:
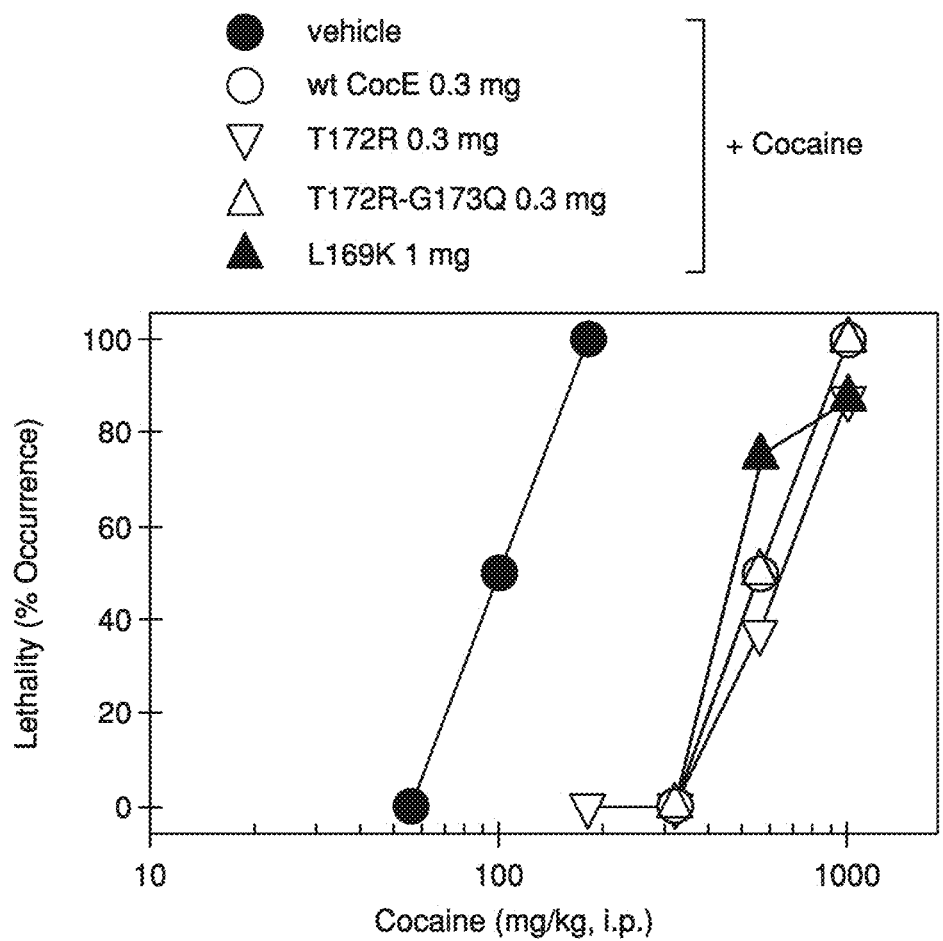
FIG. 27 is a graph showing protective effects of CocE against cocaine-induced toxicity. CocE (1 mg) was administered intravenously 1 min before cocaine administration (mg/kg, i.p.). Dose-response curves of cocaine-induced lethality in the absence or presence of CocE or mutants were plotted. Each data point represents the percentage of mice (n=6 for each dosing condition) exhibiting cocaine-induced lethality.
Figure 28:
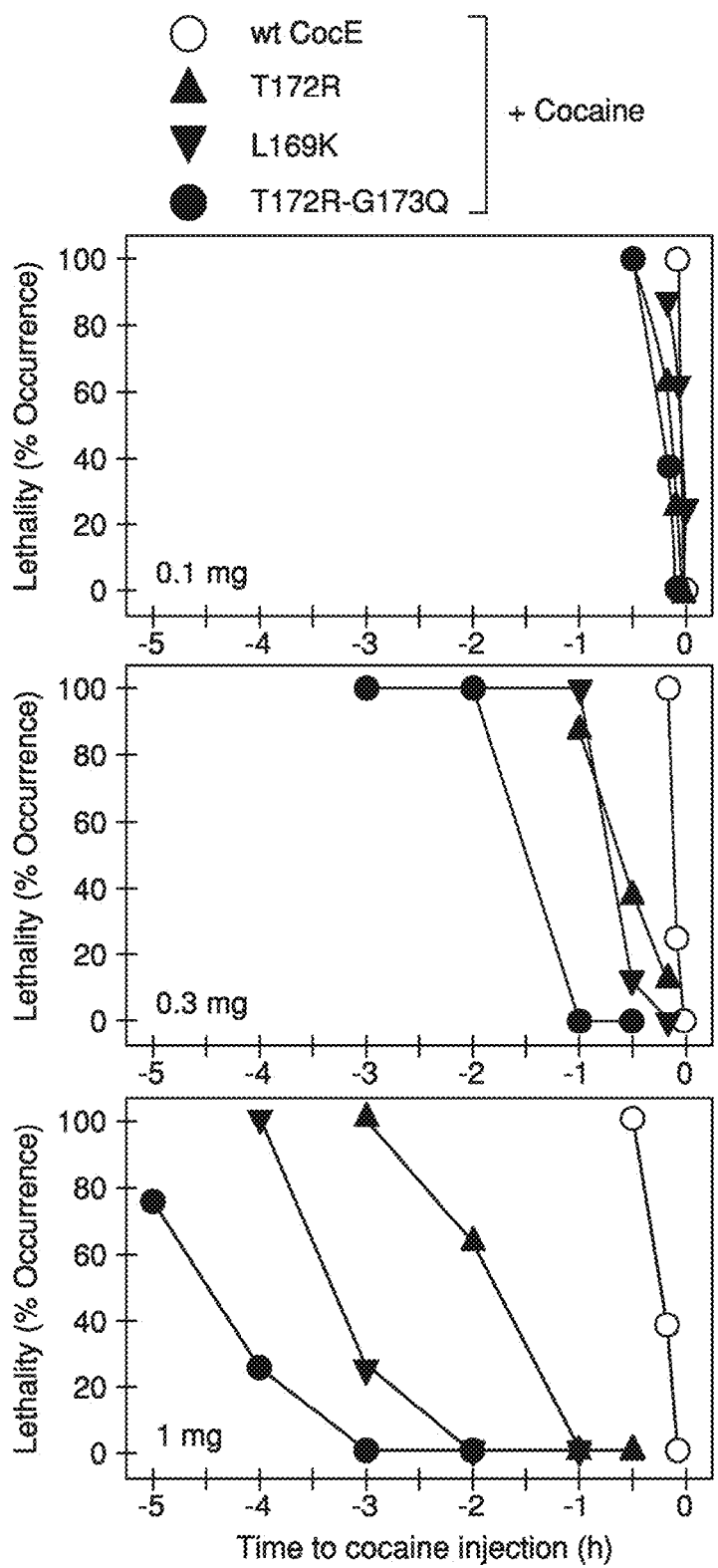
FIG. 28A-FIG. 28C are a series of graphs showing the time course of protective effects of CocE against cocaine toxicity. Each data point represents the percentage of mice (n=6 for each dosing condition) exhibiting cocaine-induced lethality.

In vivo assays. Pretreatment with wt-CocE, L169K, T172R, or T172R-G173Q 1 min prior to cocaine administration protected mice against cocaine-induced lethality (FIG. 27). The enzyme protection (at 0.3 mg, or 9 mg/kg) altered the $LD_{50}$ value of cocaine of 100 mg/kg, for the vehicle-treated group, to 560 and 670 mg/kg for wt-CocE, T172R, or T172R-G173Q (FIG. 28). L169K was slightly less effective and required larger doses (1 mg, or 30 mg/kg) to produce a similar 6-7-fold rightward shift in the cocaine dose-response curve, consistent with the decreased catalytic efficiency observed in in vitro assays.

Figure 29:
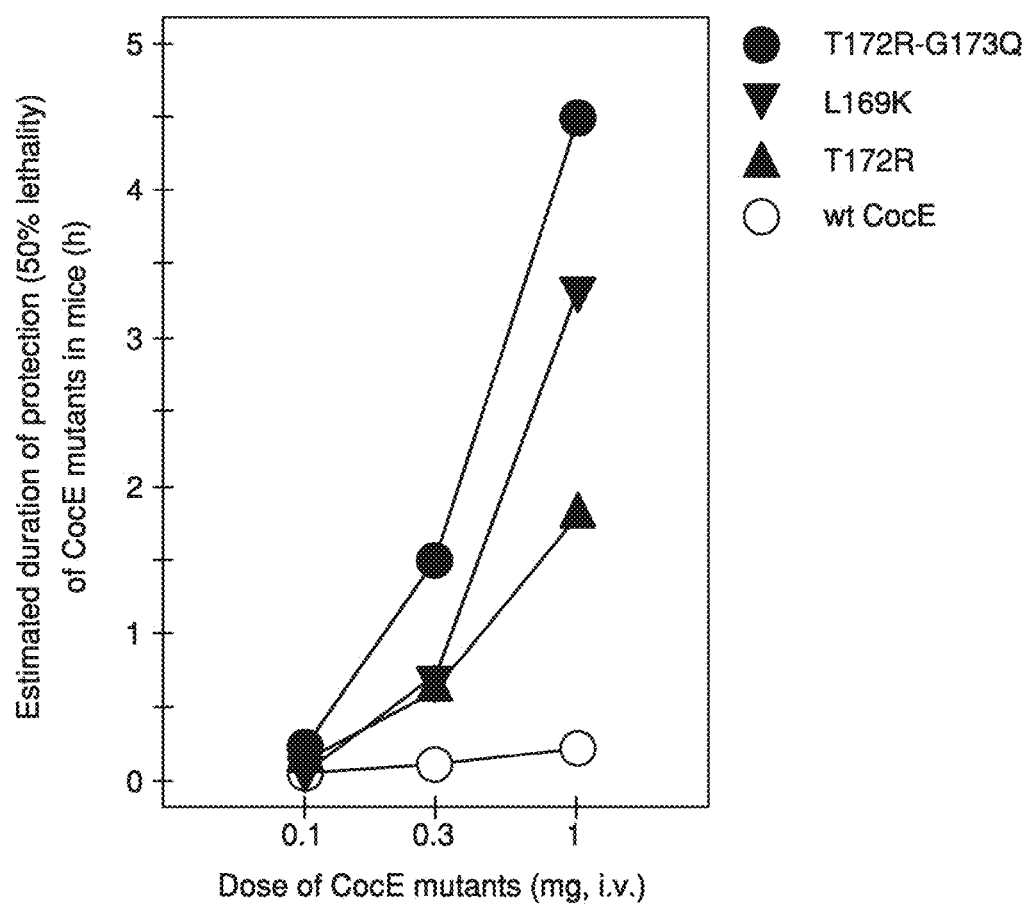
FIG. 29 is a graph showing the estimated duration of protection for 50% lethality. Time required to reach 50% lethality for CocE and each mutant was measured from the data in FIG. 28 and was plotted against dosage.

Although pretreatment (greater than 30 min) with low doses of either enzyme (0.1 mg) were ineffective against the lethal effects of cocaine, larger doses (0.3 mg and 1 mg) appeared to be effective, the durations of which were dependent on the mutation (FIG. 28 and summarized in FIG. 29). At the largest doses tested (1 mg) the enzyme pretreatment time necessary to protect to 50% lethality, $LT_{50}$, for wt-CocE was approximately 14 min. Considerably longer $LT_{50}$s were observed for T172R ($LT_{50}$~1.8 hr), L169K ($LT_{50}$~3.3 hr) and T172R-G173Q ($LT_{50}$~4.5 h), consistent with the in vitro data.

Figure 30:
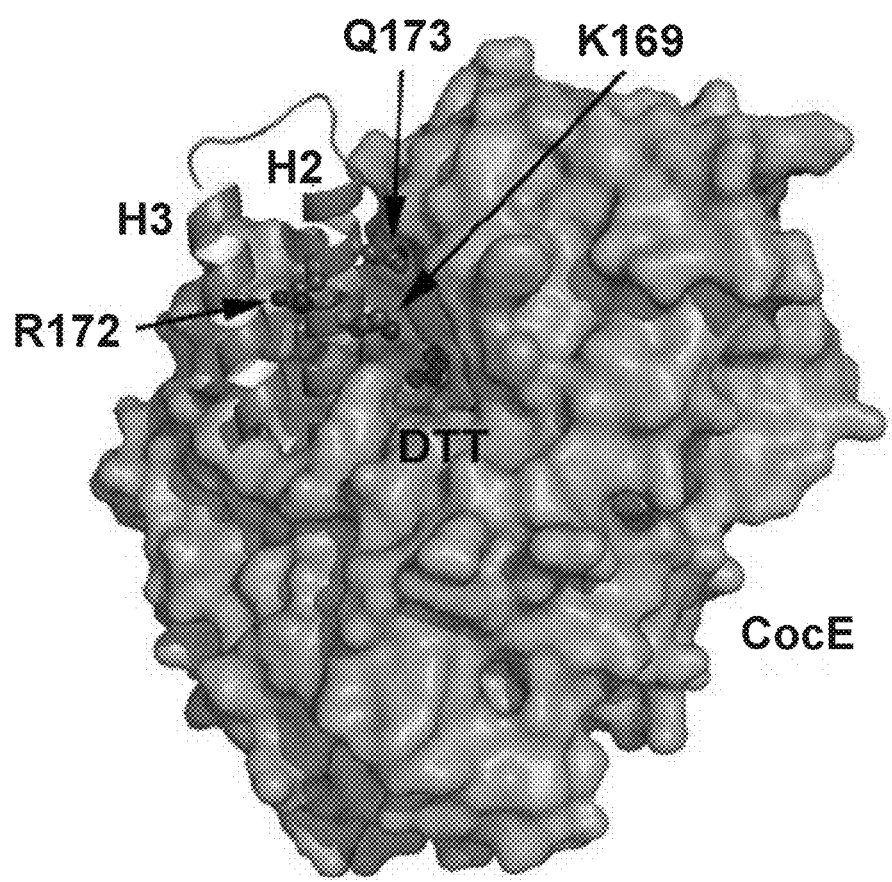
FIG. 30 is a diagram showing an overview of CocE and thermostabilizing mutations. The H2 and H3 helices of CocE are shown as coils, and the remainder of CocE as a molecular surface. The molecule of DTT observed bound in our crystal structures indicates the relative position of the active site, in a cavity adjacent to the H2 helix. The three identified stabilizing mutations are indicated. The T172R mutation leads to van der Waals interactions between R172 (H2 helix) and F189 (H3 helix). The G173Q mutation bridges the active site cleft with a new hydrogen bond (dashed lines). The L169K mutation impinges on the active site. Both DTT and glycerol are observed in the active site in this crystal structure, with K169 exhibiting multiple conformations and forming hydrogen bonds with glycerol. Note that L169 is poorly ordered in the native structure. K169 forms additional direct contacts with Y44. Glycerol binds where the tropane ring of cocaine is expected to bind, while DTT occupies the benzyl moiety binding site. Structure model was generated and rendered with PyMol (DeLano Scientific, Palo Alto, Calif.).

Structural Analysis of Stabilizing Mutants. High-resolution X-ray crystal structures of wt-CocE (1.5 Å), as well as thermal-stable mutants L169K (1.6 Å), T172R (2.0 Å), G173Q (2.5 Å), and T172R/G173Q (2.0 Å) were determined. FIG. 30 summarizes some of the results. Delineation of the structure of unliganded wt-CocE has not previously been reported and was necessary for comparison in our study.

Figure 31:
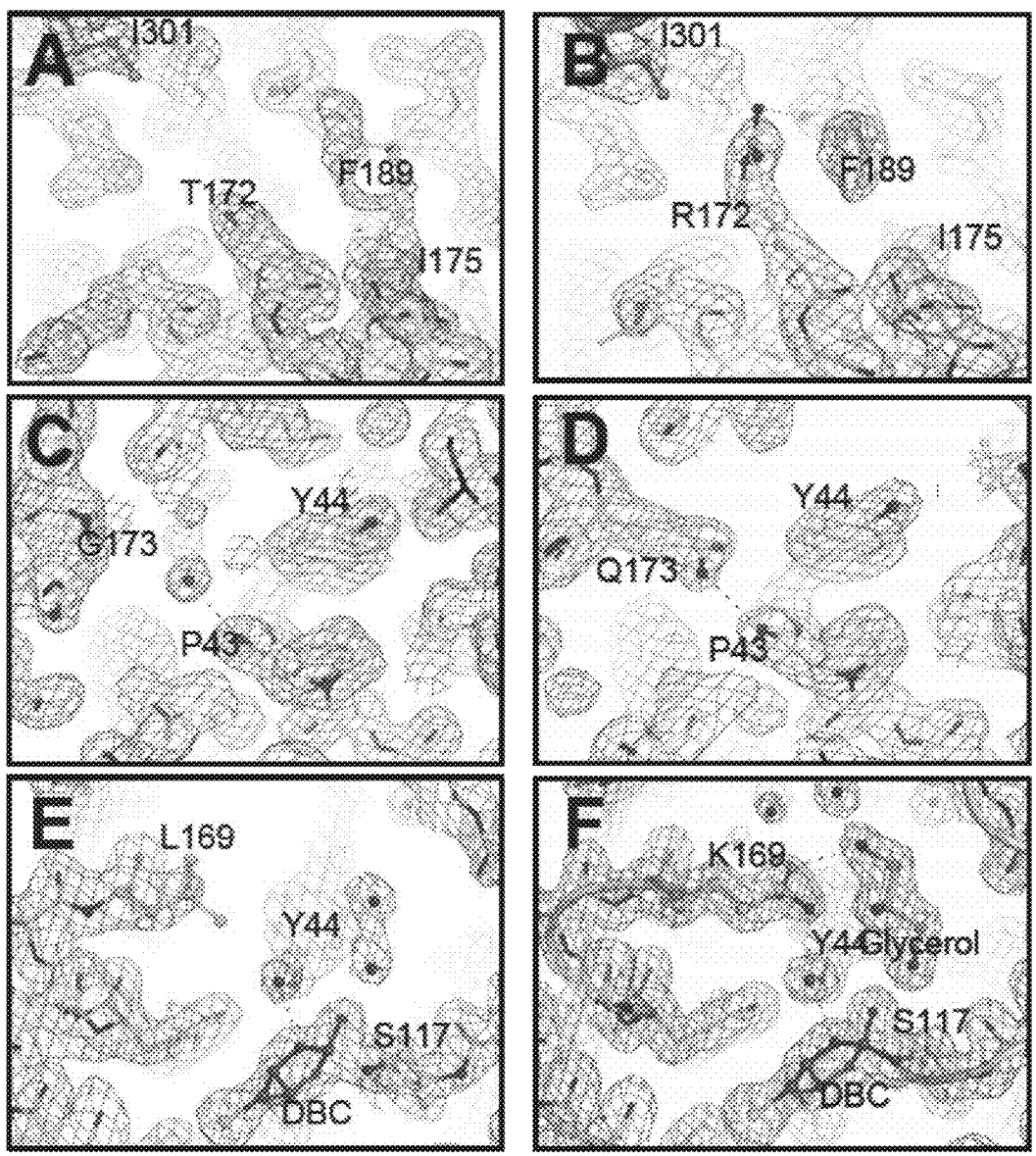
FIG. 31A-FIG. 31F are diagrams showing the structure of the thermal stable mutants. The high resolution crystal structures of T172R (B), G173Q (D) and L169K (F) are compared to the structures of wt-CocE (A, C, and E, respectively). The overall effect of the mutants appears to result from enhanced interactions between the helix 1 and 2 of domain II (R172 and F189) or interdomain interactions (Q173 with P44 and K169 with the active site). The structures of L169K in comparison with wt-CocE in the presence of 2-oxo-dioxolane butyryl carbonate (DBC) in the active site illustrates and enhanced interaction of the lysine residue with a water and the active site. The $2F_oF_c$ electron densities were contoured at 1 sigma.
Figure 32:
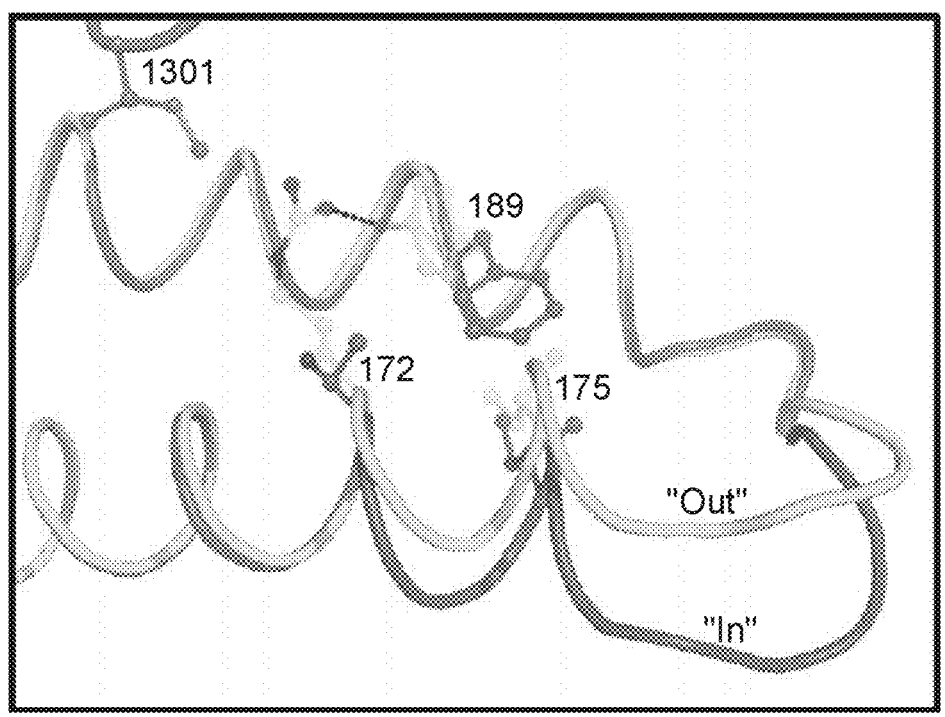
FIG. 32 is a diagram showing the stabilization of the H1-H2 loop in Domain II by R172. The substitution of arginine for threonine at residue 172 stabilizes helix 1 and helix 2 through enhancing interactions with F189. Although both the 'in' (dark) and "out" (light) conformations can be found in the wt-CocE structures, only the "out" conformation is found with T172R.

The structures of L169K, T172R, G173Q, and T172R/G173Q all show well-ordered density for their mutated side-chains (FIG. 31). In each case, the substitutions appear to increase the number of contacts/buried surface area between domains of CocE. Elongation of the side group alkyl chain and the addition of a guanidinium moiety through substitution of arginine in T172R generates both van der Waals contacts with the aromatic ring of F189 in helix H3 and a hydrogen bond between the guanidinium moiety to the backbone oxygen of F189 (FIG. 31A, B). The guanidinium side chain also packs against the I205 side chain donated by the dimer-related subunit. The side chain of G173Q forms a trans-domain hydrogen bond with the backbone carbonyl of P43 in domain I, and van der Waals contacts with Y44, whose hydroxyl contributes to the oxyanion hole of the active site (FIG. 31C,D). The L169K substitution also forms contacts with the phenyl ring of Y44 in domain I (FIG. 31E,F). The longer side chain of lysine could impinge upon the binding site of the tropane ring of cocaine, perhaps accounting for the higher $K_m$ exhibited by this mutant.

In previously reported structures (1JU3 and 1JU4) and in ours, we observe multiple distinct conformations for a region encompassing the C-terminus of the H2 and the H2-H3 loop (residues 171-183, as illustrated in FIG. 32). These two conformations are likely to be in equilibrium while in solution, but the population of these two states appears to be influenced by the mutations within the H2. Because the stabilizing mutants are found in the H2 helix, it was hypothesized that the mutants may help reduce the conformational flexibility of this region, and thus thermally protect the fold of the enzyme. For this analysis, the "out" conformation of this region was defined as that typified by the 1JU3 phenyl boronic acid adduct crystal structure, wherein this region bends away from the H5-H6 helices of domain I by up to 3.3 Å compared to the "in" conformation, typified by the 1JU4 benzoic acid crystal structure. A third conformation of this loop region was also observed, which is similar to that of 1JU4 except that residues 178-181 have a unique conformation.

The apparent global flexibility of H2-H3 mandates distinct side chain conformations within each helix. For example, in the 'out' conformation, I175 moves towards H3, forcing F189 out of the hydrophobic interface between H2 and H3, while the 'in' conformation allows F189 to be either in or out of this interface.

The structure of the T172R mutant reveals a tendency of F189 to adopt an "out" position via the close contacts of the R172 and F189 side chains, a tendency that is more prevalent in the T172R/G173Q mutant. These data would suggest that locking the planar conformation of F189 may contribute toward the thermal stabilizing effects of the T172R substitution. Substitution of alanine for phenylalanine at 189 does not reveal any enhancement or diminution of thermal stability in the T172R or wildtype background. Thus, the interactions of R172 with the H3 helix itself or perhaps with the dimer related subunit appear responsible for the enhanced stability.

Figure 33:
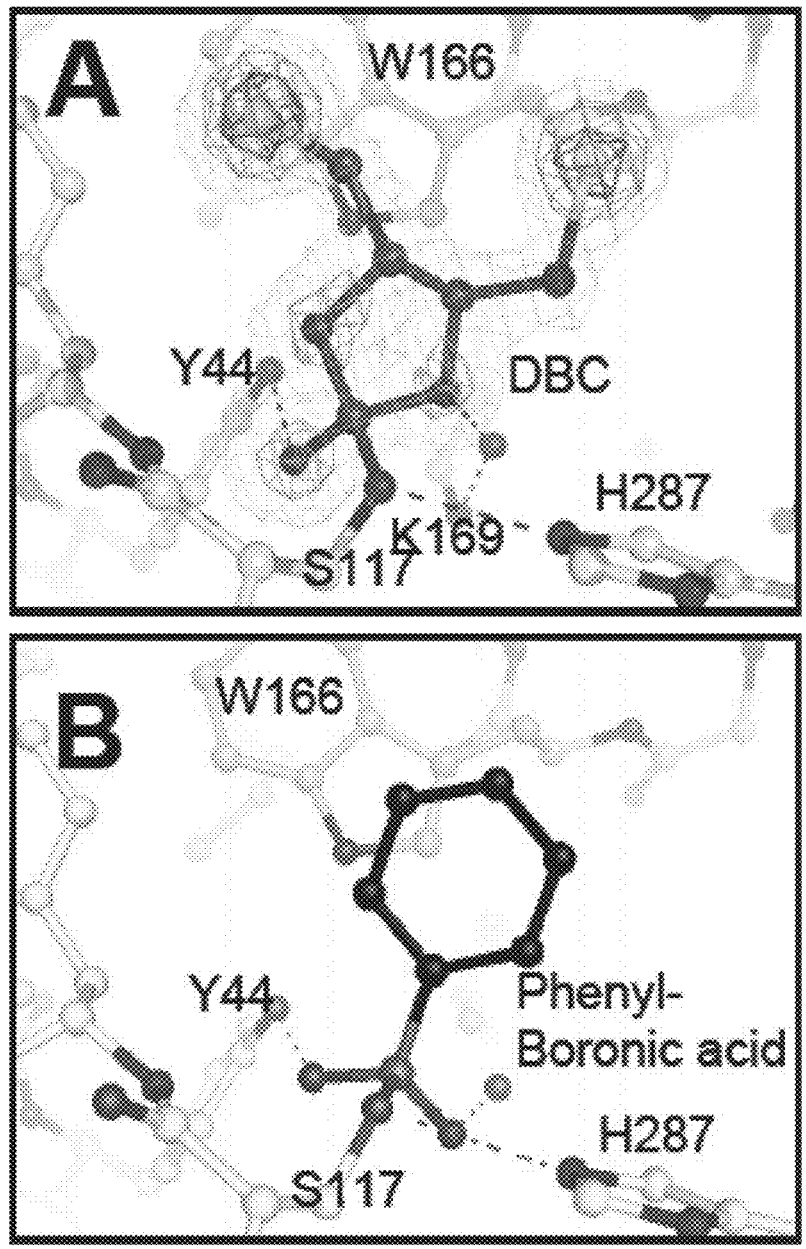
FIG. 33A-FIG. 33B are a series of diagrams showing a comparison of DBC and phenyl boronic acid in the active site of wt-CocE. DBC was found covalently bound to the active site serine 117 of crystals grown from protein isolated with DTT.

Formation of a DTT-carbonate adduct in the active site of CocE. Complicating these studies was exceptionally strong density in the active site that appeared to correspond to a covalent adduct with the catalytic serine of CocE (Ser117). Such density was not previously reported (FIG. 33) (Larsen et al., 2002). The electron density corresponded to a five membered ring with two substituent arms. Anomalous difference Fourier maps confirmed the presence of sulfur in each of the arms, and $2F_o$—$F_c$ omit maps contoured at different levels identified the oxygen atoms in the adduct (FIG. 33). Thus, it was concluded that the density corresponds to DTT, which was included in the crystallization and harvesting solutions (at 10 mM), that was reacted with bicarbonate in the active site. The 2-oxo-dioxolane ring appears trapped as a tetrahedral intermediate dead-end complex, with one of the tetrahedral oxygens occupying the oxyanion hole forming the adduct, 2-oxo-dioxolane butyryl carbonate, or DBC. In the highest resolution structure (L169K), the carbon presumably donated by carbonate in the dioxolane ring is ~1.6 Å (distance was not restrained in refinement of the high resolution structures) from the S117 γ-oxygen, the oxygen in the oxyanion hole, and 1.4-1.5 Å from the oxygen in the oxyanion hole and the two oxygen atoms donated by DTT, most consistent with covalent bounds. The electron density of this tetrahedral carbon is weaker than that of the other carbons in the DTT ligand, suggesting electron withdrawal. The 2-oxo-dioxolane adduct adopts a similar conformation to the 2-phenylboronate adduct with CocE (Larsen et al., 2002), except that the tetrahedral center is rotated.

To confirm that formation of this adduct complex was not a consequence of our stabilizing mutants, the wt-CocE structure was determined in the presence and absence of DTT, and the structures of stabilizing mutants of CocE were also determined in the absence of DTT. In all cases where DTT was co-crystallized with CocE, the adduct was observed, and the position of the H2-H3 insert was essentially the same with or without DTT. Under the in vitro conditions tested here, i.e. relatively short incubation times with DTT (<60 min), DTT inhibits CocE activity competitively with substrate. Note that crystal growth conditions are considerably different with incubation times in the days to weeks, a time scale that could conceivably allow for the formation of the DBC adduct. Adduct formation should also display markedly different inhibition patterns and appear as a non-competitive inhibitor. Crystals grown without DTT, or grown with DTT and subsequently soaked in the cocaine analog atropine which appeared to displace the adduct, instead showed a water molecule near S117 and high B-factors for active site residues including S117 and H287 of the catalytic triad.

Discussion

To date, CocE is the most efficient catalyst for hydrolyzing cocaine and for decreasing cocaine levels in vivo and to protect against cocaine-induced lethality in mice and rats (Turner et al., 2002; Ko et al., 2007; Cooper et al., 2006; Garrera et al., 2005; Gasior et al., 2000; Daniels et al., 2006; WO/2008/08358). The effectiveness of this "antidote" for cocaine toxicity in rodents indicates that CocE is a potential therapeutic in humans. However, wt-CocE displays considerable instability as its effective half-life in the blood stream is ~10 min. In comparison, tetrameric BchE, remains in mice plasma for 16 hours and active for up to 7 hour post injection (Duysen et al., 2002) while anti-cocaine Ab, remains in mouse circulation for 8.1 days (Norman et al., 2007). Even so, the clinical potential of wt-CocE suggests that its duration of protection is likely sufficient in acute overdose cases, such as those due to snorting or injection (Landry et al., 1993).

In cases involving massive overdoses, as is the case for "cocaine mules" wherein large amounts of cocaine will be released into the bloodstream over a long period of time, a longer acting CocE is desired. The short effective plasma half-life of CocE therefore represents a major obstacle in developing this protein-based therapeutic for acute treatment of cocaine-induced lethality and for chronic treatment of cocaine abuse.

Here, in vitro data is provided demonstrating that the relatively short half-life in vivo may be a result of the thermal inactivation of CocE readily observed in vitro. The thermal sensitivity of CocE may reflect the fact that Rhodococcus sp., the microorganism which CocE was isolated from, thrives in the soil beneath coca plants under moderate temperatures around 20° C. (Mackay, 1886; Martin, 1952), much lower than the body temperature of rodents (37-38° C.).

Of the 36 mutants predicted computationally, three mutations displayed an enhanced thermal stability. A number of the mutants were not stable and could not be overexpressed and purified as a functional enzyme (Table 1). By combining two of the thermal stable point mutants, a thermally quite stable mutant of CocE was created, G173Q/T172R, which extends the in vitro $\tau_{inact}$ at 37° C. from 10 min to 4½ hours, or approximately 27-fold. In vivo analysis of the mutants in rodents, as a function of their capacity to protect against acute cocaine-induced lethality, were in concordance with the in vitro assays.

The results of computational modeling studies were striking in that several stable mutants were identified in an enzyme of 574 amino acid residues. Unfortunately, the resolution of these methods were not sufficient enough to elucidate the precise mechanism underlying the thermal stabilizing effects of the mutants. In combination with x-ray crystallography, however, it was possible to ascertain a reasonable model to account for the enhance stability at an atomic resolution. In general the substitution of larger or charged residues such as glutamine (for glycine), lysine (for leucine) or arginine (for threonine), helped to stabilize domain-domain interactions. The most thermally unstable domain in the enzyme was identified as Domain II, which contains the H2 and H3 helices.

The location of the thermally stable substitutions in the H2-H3 helices, and the structural heterogeneity of the H2-H3 loop itself, suggests that the H2-H3 helical region is inherently unstable and may ultimately nucleate or at least contribute strongly to the aggregation or unfolding of CocE. CocE orthologs from Listeria and Pseudomonas sp., both of which are capable of surviving at 37° C., have significantly shorter H2 & H3 helices and therefore a potentially more stable domain 2 (Genbank Accession codes ZP 01928677 and YP 660510, respectively). Truncation or complete removal of the loop between the H2 and H3 helices in CocE, however, inactivated the enzyme (see Table 1).

The presence of a DTT-carbonate adduct in the active site of CocE is apparently catalyzed by the enzyme. Other carbonates, such as propylene carbonate (4-methyl-2-oxo-1,3-dioxolane), are reported to decompose into propylene glycol and $CO_2$ in water. The reverse synthesis from DTT, a vicinal diol, and $CO_2$ is thus conceivable. The DTT adduct appears to be bound covalently to the catalytic S117 much in the overall manner as phenyl boronic acid (Larsen et al., 2002), although its bond length of 1.6 Å (as opposed to the expected distance of ~1.43 Å) suggests partial covalent character. The plane of the dioxolane ring of DBC overlaps the plane of the phenyl ring of both phenyl boronic acid- and benzoic acid-bound forms of CocE (Larsen et al., 2002). Because the conformation of the active site residues of wt-CocE bound to DBC differs very little from the phenyl boronic acid-bound form, its possible that the adduct was not observed in the crystal structure by Larson et al. (2002) due to the mutually exclusive binding of benzoic acid or phenyl boronate.

The crystal structure of CocE suggests that the enzyme exists as a dimer, and preliminary studies suggest that the dimer is stable enough at low concentrations to be resolved by gel filtration, although pre-treatment at 37° C. induces protein aggregation and elution from a size exclusion column in the column void. Interestingly, careful analysis of the kinetics of inactivation of both T172R/G173Q and L169K reveal that the activity diminishes exponentially in the first phase the activity but appears to reach a plateau at approximately 35% of their maximal activity. This activity remains even after greater than 8 hr, in contrast to wt-CocE, G173Q and T172R where the activity decays to less than 10% activity within 90 min. One plausible explanation for this behavior (of T172R/G173Q and L169K) is that there still remains a thermally-sensitive portion of the enzyme that does not result in complete enzyme inactivation. The remaining thermally-sensitive region may be located at the dimer interface, the disruption of which could lead to aggregation. The gel filtration chromatography data mentioned earlier would concur with this notion. Indeed, further studies and the characterization of additional mutants within the dimer interface are ongoing.

Perhaps the most dramatic effect of the mutations is revealed by their in vivo ability to protect against cocaine-induced lethality. The effect of the mutations paralleled our in vitro data through extending the duration of pretreatment that the enzyme is capable of withstanding. In the case of T172R/G173Q the pretreatment duration in which the enzyme was still capable of protecting against cocaine-induced lethality by 50% was extended by greater than 20-fold, or up to 4.5 hours. This strongly suggests that the cause of the in vivo instability of CocE is the same as that observed for the enzyme in vitro.

In summary, the present work shows that a multi-pronged approach combining computational, biochemical and structural analysis can be used to rationally develop variants of CocE that are significantly more stable than the native enzyme.

EXAMPLE 5

CocE Mutant L169K/G173Q

A mutant of CocE, L169K/G173Q, was created and characterized as follows.

Design of thermostable mutations. Based on the X-ray crystal structure (PDB code 1JU3) of the bacterial cocaine esterase (CocE) (Larsen et al., 2002), a complete 3D model of CocE bound to (−)-cocaine was built using energy minimizations and molecular dynamics (MD) simulations encumbered within the AMBER program (Case et al., 2004) (See Example 4 above). To increase the thermostability of CocE, a computational method implemented in the RosettaDesign program was used (Kuhlman and Baker, 2000; Korkegian et al., 2005). This method was capable of predicting thermostabilizing mutations within a given fold while minimizing any shift in the backbone that might structurally disrupt the active site structure or quench its flexibility. The method implemented in the RosettaDesign program uses an energy function for evaluating the fitness of a particular sequence for a given fold and a Monte Carlo search algorithm for sampling sequence space. The same method has successfully been used by other researchers to increase thermostability of an enzyme with no reduction in catalytic efficiency (Kuhlman and Baker, 2000; Korkegian et al., 2005). The computational modeling using the RosettaDesign program has allowed the prediction of a set of mutations that can potentially lower the energy and, therefore, increase the higher thermostability of CocE. As the first round of the rational design, the computation was simplified by only considering the possible mutations on the amino acid residues that have a distance of 6-25 Å from the catalytic site.

Site directed mutagenesis. Point mutations at positions 169 and 173 were introduced into the CocE cDNA cloned in the bacterial expression vector, pET-22b(+). Mutations were generated using a modified QuickChange (Stratagene) mutagenesis protocol and single oligonucleotide primers. For generation of the double mutant, cDNAs with the single G173Q point mutation was used as a template for the second round of mutagenesis to introduce L169K. The mutant was sequenced in both directions over the entire coding region. Wild-type and CocE mutants were expressed as C-terminally-6× His-tagged proteins in E. coli BL-21 Gold (DE3) cells grown at 37° C. Protein expression was induced with 1 mM isopropyl-β-thiogalactopyranoside (IPTG, Fisher) for 12 hours at 18° C.

Purification of cocaine esterase and mutants. Cells were pelleted, resuspended in 50 mM Tris pH 8.0, 150 mM NaCl with protease inhibitors (3 µg/ml each of leupeptin and lima bean or soybean trypsin inhibitor) and lysed using a French press (Thermo Fisher Scientific Corp, USA). Wild-type or mutant CocE was enriched using Talon metal affinity chromatography (Clontech Laboratories, Inc, Mountain View Calif.), followed by anion-exchange (Q-Sepharose, GE Healthcare, Piscataway N.J.) chromatography. CocE was eluted from the Q-Sepharose column with 150-450 mM NaCl linear gradient buffers containing 20 mM Hepes pH 8.0, 2 mM $MgCl_2$, 1 mM EDTA and 1 mM DTT. The peak fractions were pooled and concentrated by Centricon-30 (Millipore), snap frozen in liquid nitrogen and stored at −80° C.

Figure 34:
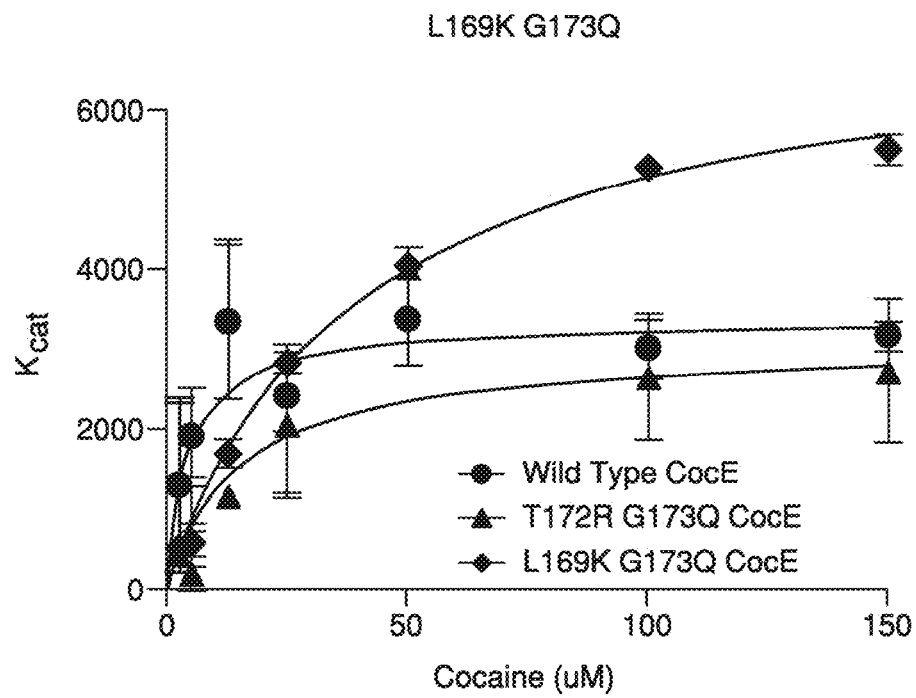
FIG. 34A is a graph showing catalytic parameters of wt-CocE and two double mutants.
FIG. 34B is a table showing catalytic parameters of wt-CocE and two double mutants.

Determination of Catalytic Efficiency. To determine the catalytic activity a spectrophotometric assay was performed. Samples of L169K/G173Q CocE were added to a 96-well UV permeable plate containing increasing cocaine concentrations (0.5, 2.5, 5, 12.5, 25, 50, 100, and 150 µM) to give a final concentration of 10 ng/ml CocE in a final volume of 200 µl. The change in absorbance at 240 nm was measured over 20 minutes, with readings every 10 seconds, by a SpectraMax Plus 384 UV plate reader (Molecular Devices, Sunnyvale, Calif.) using SOFTmax Pro software (Version 3.1.2). The change in absorbance was converted to the change in concentration and furthermore the rate of decay per mole enzyme is determined ($K_{cat}$). $K_{cat}$ and $K_m$ of the enzyme are determined using Prism (GraphPad software, San Diego). The L169K/G173Q mutation allows each molecule of the enzyme to turn over approximately 6000 molecules of cocaine per minute into inactive metabolites. The increase in $K_{cat}$ over the wildtype and the previous T172R/G173Q mutation is accompanied by an increase in $K_m$, which results in a similar catalytic efficiency to both the wild type and T172R/G173Q mutation (FIG. 34).

Determination of in vitro half life. To mimic body temperature and enzyme concentration in the NIH Swiss mouse, CocE was incubated in a 37° C. water bath at a concentration of 60 µg/ml in either human plasma or phosphate buffered saline (PBS) pH 7.4. The samples were added to the 37° C. water directly from −80° C. storage at varying times (0, 24, 48, 77, 96, 120 hours) and all were assayed at a final concentration of 10 ng/ml as described above.

Figure 35:
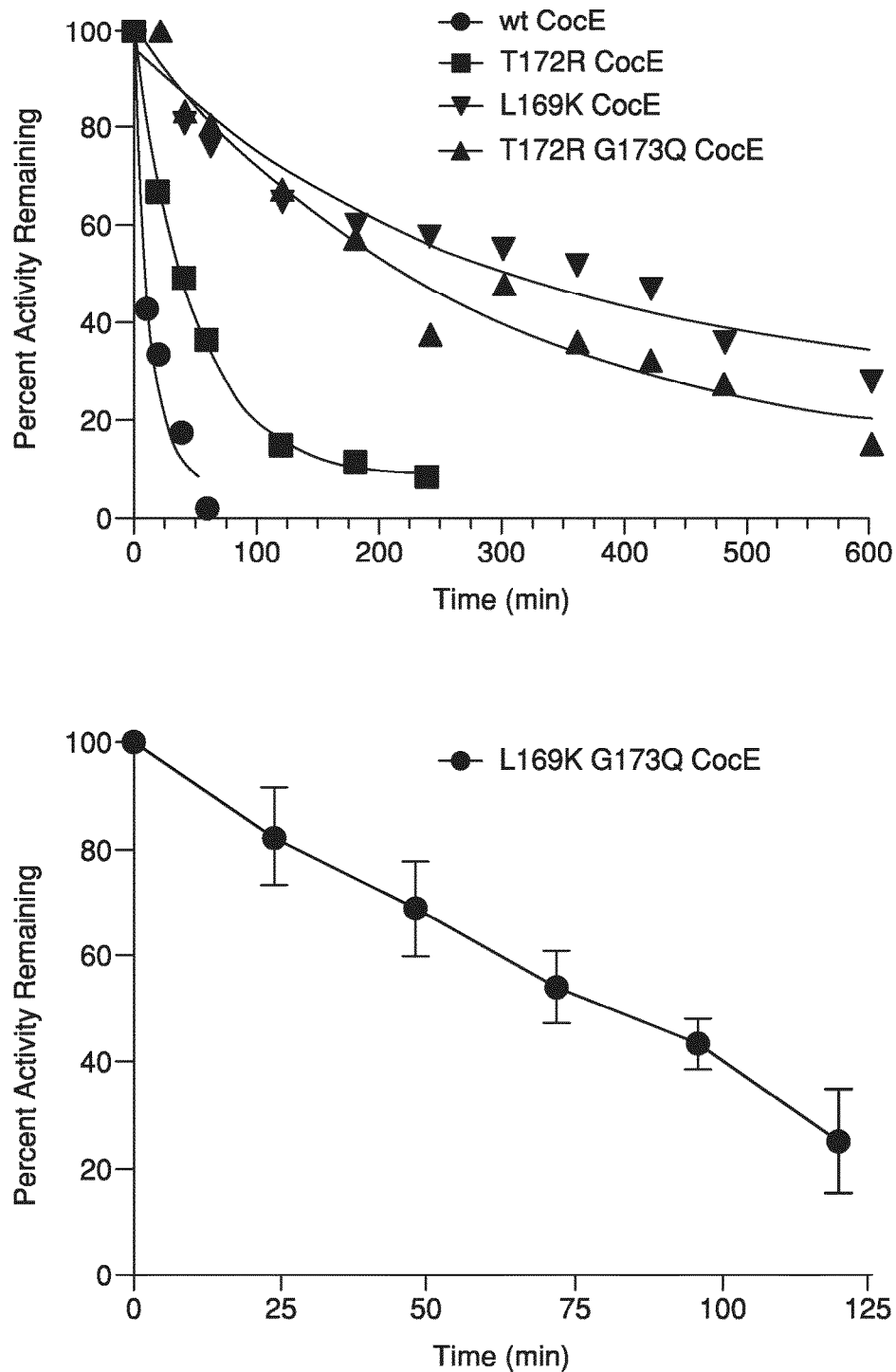
FIG. 35A is a graph showing in vitro loss of activity of wt-CocE, two CocE mutants (T172R and L169K), and a double mutant combining T172R and G173Q mutations.
FIG. 35B is a graph showing in vitro loss of activity of a double mutant combining two single mutations, L169K and G173Q.

The substitution of a lysine and a glutamate and positions 169 and 173 respectively extends the in vitro half life to approximately 72 hours, which is 332 times longer than the wild type enzyme and 17 times longer than the T172R/G173Q mutation (FIG. 35).

Figure 36:
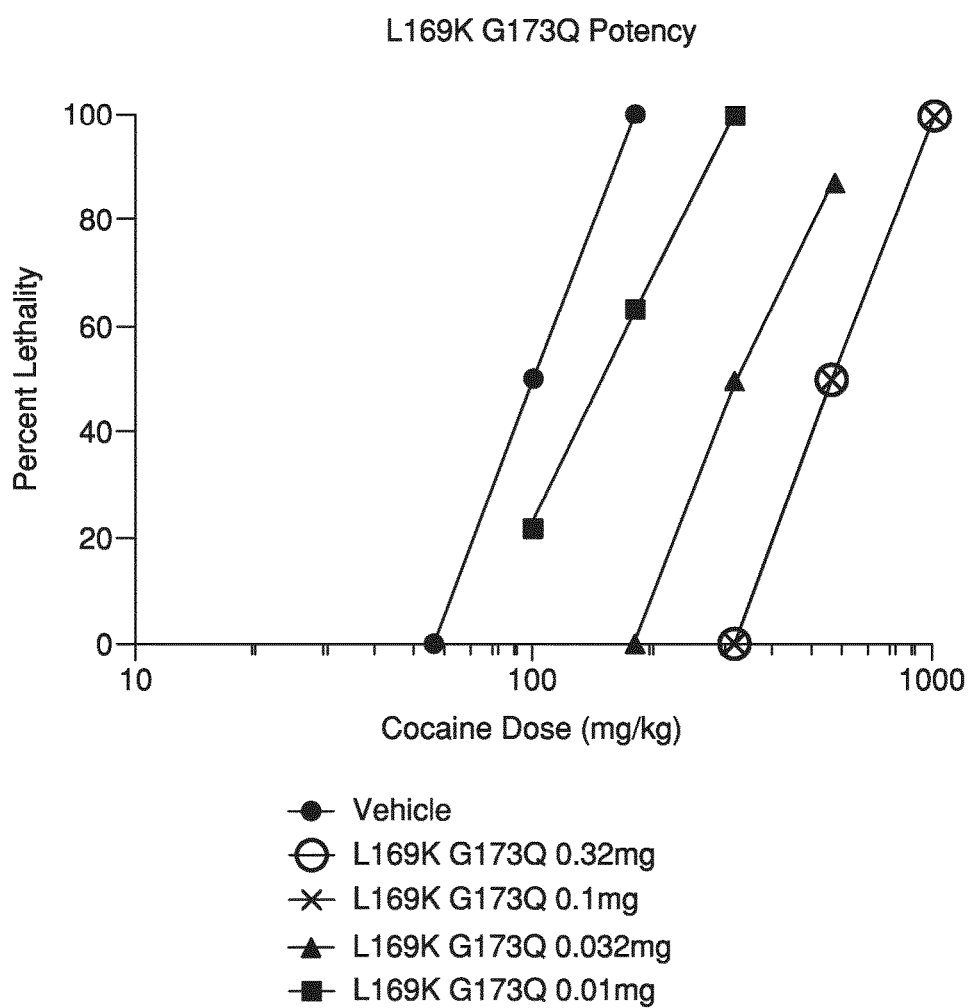
FIG. 36 is a graph showing protection of mice from a lethal cocaine dose by the CocE L169K/G173Q mutant.

Determination of in vivo potency. The increase in $K_{cat}$ has been shown in vivo as well. The L169K/G173Q mutated CocE dose-dependently protected mice from increasing lethal doses of cocaine (FIG. 36). CocE was administered IV into the tail vein of NIH Swiss mice in a volume of 0.2 ml. Varying concentrations of cocaine were delivered into the intraperitoneal cavity 1 min later. This mutant has shown to be more potent than previous CocE mutants, maintaining some degree of protection at doses as low as 0.01 mg. The increased potency should allow less enzyme to be used and therefore should decrease the innate immunological responses of the animals to the protein. Increased potency also makes this enzyme more effective against extreme doses of cocaine that may be seen in a human overdose, at equivalent concentrations to other enzyme mutation.

Figure 37A:
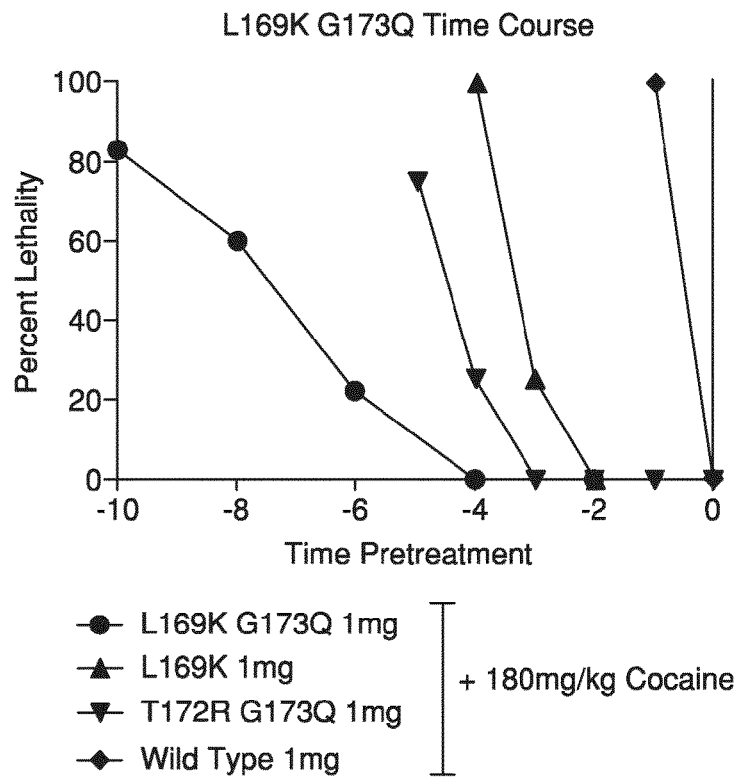
FIG. 37A-FIG. 37B are a series of graphs showing a time course of protection of mice from a lethal cocaine dose by the CocE L169K/G173Q mutant.
Figure 37B:
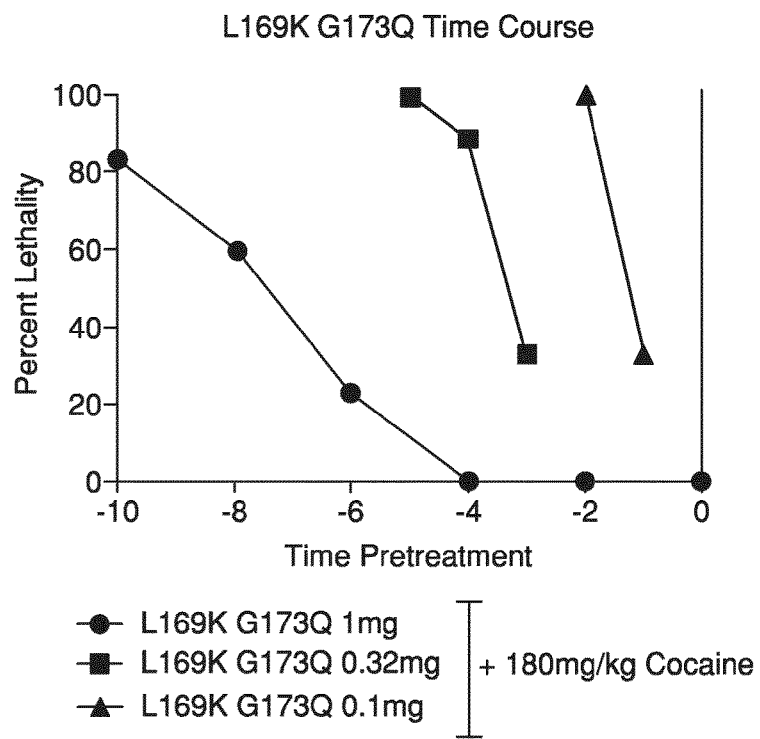

Evaluation of in vivo half life. CocE is administered IV to the tail vein in a volume of 0.2 ml. Animals are challenged with 180 mg/kg cocaine delivered intraperitoneally at a given time after CocE administration. The L169K/G173Q mutant of CocE was tested at 1 mg against the other mutants because 1 mg of CocE showed the greatest separation between in vivo thermostabilities of different CocE mutants in preliminary studies (data not shown). The L169K/G173Q mutant of CocE (1 mg) protected 50% of NIH Swiss mice from death for up to 7.5 hrs. Lower does of the L169K/G173Q mutation show extended protection against lethality as compared to previous mutations as well (FIG. 37).

```
Rhodococcus CocE amino acid sequence
                                                   SEQ ID NO: 1
    1  mvdgnysvas  nvmvpmrdgv  rlavdlyrpd  adgpvpvllv
       rnpydkfdvf  awstqstnwl 61  efvrdgyavv  iqdtrglfas  egefvphvdd  eadaedtlsw
       ileqawcdgn  vgmfgvsylg 121  vtqwqaaysg  vgglkaiaps  masadlyrap  wygpggalsv
       eallgwsali  gtglitsrsd 181  arpedaadfv  qlaailndva  gaasvtplae  qpllgrlipw
       vidqvvdhpd  ndeswqsisl 241  ferlgglatp  alitagwydg  fvgeslrtfv  avkdnadarl
       vvgpwshsnl  tgrnadrkfg 301  iaatypiqea  ttmhkaffdr  hlrgetdala  gvpkvrlfvm
       gidewrdetd  wplpdtaytp 361  fylggsgaan  tstgggtlst  sisgtesadt  ylydpadpvp
       slggtllfhn  gdngpadqrp 421  ihdrddvlcy  stevltdpve  vtgtvsarlf  vsssavdtdf
       taklvdvfpd  graialcdgi 481  vrmryretlv  nptlieagei  yevaidmlat  snvflpghri
       mvqvsssnfp  kydrnsntgg 541  viareqleem  ctavnrihrg  pehpshivlp  iikr
```

REFERENCES

Administration, S.A.a.M.H.S. Drug Abuse Warning Network, 2005: National Estimates of Drug-Related Emergency Department Visits. (ed. Office of Applied Studies, U.D.o-.H.a.H.S.) (2005).

Baird, T. J., Deng, S. X., Landry, D. W., Winger, G. & Woods, J. H. Natural and artificial enzymes against cocaine. I. Monoclonal antibody 15A10 and the reinforcing effects of cocaine in rats. J Pharmacol Exp Ther 295, 1127-34 (2000).

Bauman J L and DiDomenico R J. J Cardiovasc Pharmacol Ther 7, 195-202 (2002).

Benowitz, N. L. Clinical pharmacology and toxicology of cocaine. Pharmacol Toxicol 72, 3-12 (1993).

Bresler, M. M., Rosser, S. J., Basran, A. & Bruce, N. C. Gene cloning and nucleotide sequencing and properties of a cocaine esterase from Rhodococcus sp. strain MB 1. Appl Environ Microbiol 66, 904-8 (2000).

Browne, S. P., Slaughter, E. A., Couch, R. A., Rudnic, E. M. & McLean, A. M. The influence of plasma butyrylcholinesterase concentration on the in vitro hydrolysis of cocaine in human plasma. Biopharm Drug Dispos 19, 309-14 (1998).

Carmona, G. N. et al. Plasma butyrylcholinesterase activity and cocaine half-life differ significantly in rhesus and squirrel monkeys. Life Sci 59, 939-43 (1996).

Carmona et al. Drug Metabolism & Disposition 28, 367-371 (2000).

Carrera, M. R., Ashley, J. A., Wirsching, P., Koob, G. F. & Janda, K. D. A second-generation vaccine protects against the psychoactive effects of cocaine. Proc Natl Acad Sci USA 98, 1988-92 (2001).

Carrera, M. R. et al. Treating cocaine addiction with viruses. Proc Natl Acad Sci USA 101, 10416-21 (2004).

Carrera, M. R., Trigo, J. M., Wirsching, P., Roberts, A. J. & Janda, K. D. Evaluation of the anticocaine monoclonal antibody GNC92H2 as an immunotherapy for cocaine overdose. Pharmacol Biochem Behav 81, 709-14 (2005).

Carroll F I, Howell L L and Kuhar M. J. J Med Chem 42, 2721-2736 (1999).

Case, D. A. et al. AMBER 8. University of California, San Francisco (2004).

The CCP4 suite: programs for protein crystallography. Acta Crystallogr D Biol Crystallogr 50, 760-3 (1994).

Comer, S. D. et al. Depot naltrexone: long-lasting antagonism of the effects of heroin in humans. Psychopharmacology (Berl) 159, 351-60 (2002).

Cooper, Z. D. et al. Rapid and robust protection against cocaine-induced lethality in rats by the bacterial cocaine esterase. Mol Pharmacol 70, 1885-91 (2006).

Daniels, A., Ayala, E., Chen, W., Coop, A. & Matsumoto, R. R. N-[2-(m-methoxyphenyl)ethyl]-N-ethyl-2-(1-pyrrolidinyl)ethylamine (UMB 116) is a novel antagonist for cocaine-induced effects. Eur J Pharmacol 542, 61-8 (2006).

Deng, S. X., de Prada, P. & Landry, D. W. Anticocaine catalytic antibodies. J Immunol Methods 269, 299-310 (2002).

Duysen, E. G., Bartels, C. F. & Lockridge, O. Wild-type and A328W mutant human butyrylcholinesterase tetramers expressed in Chinese hamster ovary cells have a 16-hour half-life in the circulation and protect mice from cocaine toxicity. J Pharmacol Exp Ther 302, 751-8 (2002).

Emsley, P. & Cowtan, K. Coot: model-building tools for molecular graphics. Acta Crystallogr D Biol Crystallogr 60, 2126-32 (2004).

Gao Y and Brimijoin S. Journal of Pharmacology & Experimental Therapeutics 310, 1046-1052 (2004).

Gao, Y. et al. Gene transfer of cocaine hydrolase suppresses cardiovascular responses to cocaine in rats. Mol Pharmacol 67, 204-11 (2005).

Gasior, M., Ungard, J. T. & Witkin, J. M. Chlormethiazole: effectiveness against toxic effects of cocaine in mice. J Pharmacol Exp Ther 295, 153-61 (2000).

Gorelick, D. A. Enhancing cocaine metabolism with butyrylcholinesterase as a treatment strategy. Drug Alcohol Depend 48, 159-65 (1997).

Grabowski et al. Addictive Behaviors 29, 1439-1464 (2004).

Inaba T. Canadian Journal of Physiology & Pharmacology 67, 1154-1157 (1989).

Kantak, K. M. Anti-cocaine vaccines: antibody protection against relapse. Expert Opin Pharmacother 4, 213-8 (2003).

Knuepfer M M. Pharmacol Ther 97, 181-222 (2003).

Ko, M. C. et al. Cocaine esterase: interactions with cocaine and immune responses in mice. J Pharmacol Exp Ther 320, 926-33 (2007).

Korkegian, A., Black, M. E., Baker, D. & Stoddard, B. L. Computational thermostabilization of an enzyme. Science 308, 857-60 (2005).

Kosten et al. Vaccine 20, 1196-1204) (2002).

Krissinel, E. & Henrick, K. Secondary-structure matching (SSM), a new tool for fast protein structure alignment in three dimensions. Acta Crystallogr D Biol Crystallogr 60, 2256-68 (2004).

Kuhlman, B. & Baker, D. Native protein sequences are close to optimal for their structures. Proc Natl Acad Sci USA 97, 10383-8 (2000).

Landry, D. W., Zhao, K., Yang, G. X., Glickman, M. & Georgiadis, T. M. Antibody-catalyzed degradation of cocaine. Science 259, 1899-901 (1993).

Larsen, N. A. et al. Crystal structure of a bacterial cocaine esterase. Nat Struct Biol 9, 17-21 (2002).

Lynch, T. J. et al. Cocaine detoxification by human plasma butyrylcholinesterase. Toxicol Appl Pharmacol 145, 363-71 (1997).

Mackay, J. B. L. Erythroxylon coca. *Tropical Agriculturist* 6, 249 (1886).

Martin, L. A. Brief notes on the cultivation of coca. *Agronomia* 17, 77-80 (1952).

Mattes, C. E. et al. Therapeutic use of butyrylcholinesterase for cocaine intoxication. Toxicol Appl Pharmacol 145, 372-80 (1997).

Meijler, M. M. et al. Fluorescent cocaine probes: a tool for the selection and engineering of therapeutic antibodies. J Am Chem Soc 127, 2477-84 (2005).

Mets, B. et al. A catalytic antibody against cocaine prevents cocaine's reinforcing and toxic effects in rats. Proc Natl Acad Sci USA 95, 10176-81 (1998).

Murshudov, G. N., Vagin, A. A. & Dodson, E. J. Refinement of macromolecular structures by the maximum-likelihood method. Acta Crystallogr D Biol Crystallogr 53, 240-55 (1997).

Newman, A. H. & Rothman, R. B. *Addiction*, 169-192 (Elsevier, Amsterdam, London, 2007).

Norman, A. B. et al. A chimeric human/murine anticocaine monoclonal antibody inhibits the distribution of cocaine to the brain in mice. J Pharmacol Exp Ther 320, 145-53 (2007).

Otwinowski, Z., Minor, W. & Charles W. Carter, Jr. [20] Processing of X-ray diffraction data collected in oscillation mode. in Methods in Enzymology, Vol. Volume 276 307-326 (Academic Press, 1997).

Rogers, C. J., Mee, J. M., Kaufmann, G. F., Dickerson, T. J. & Janda, K. D. Toward cocaine esterase therapeutics. J Am Chem Soc 127, 10016-7 (2005).

Sun et al. Molecular Pharmacology (2002a).

Sun et al. Pharmacology & Experimental Therapeutics 302, 710-716 (2002b).

Turner, J. M. et al. Biochemical characterization and structural analysis of a highly proficient cocaine esterase. Biochemistry 41, 12297-307 (2002).

Veronese, F. M. & Harris, J. M. Introduction and overview of peptide and protein pegylation. Adv Drug Deliv Rev 54, 453-6 (2002).

Wilson L D and Shelat C. J Toxicol Clin Toxicol 41, 777-788 (2003).

Xie, W. et al. An improved cocaine hydrolase: the A328Y mutant of human butyrylcholinesterase is 4-fold more efficient. Mol Pharmacol 55, 83-91 (1999).

Yang, G. et al. Anti-Cocaine Catalytic Antibodies: A Synthetic Approach to Improved Antibody Diversity. J. Am. Chem. Soc. 118, 5881-5890 (1996).

PCT publication WO/2008/008358.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of treating a cocaine-induced condition, the method comprising:

administering to a mammalian subject in need thereof an effective amount of a composition comprising a cocaine esterase (CocE) polypeptide comprising an amino acid sequence at least 85% identical to SEQ ID NO: 1 having esterase activity; and at least one thermostabilization compound selected from

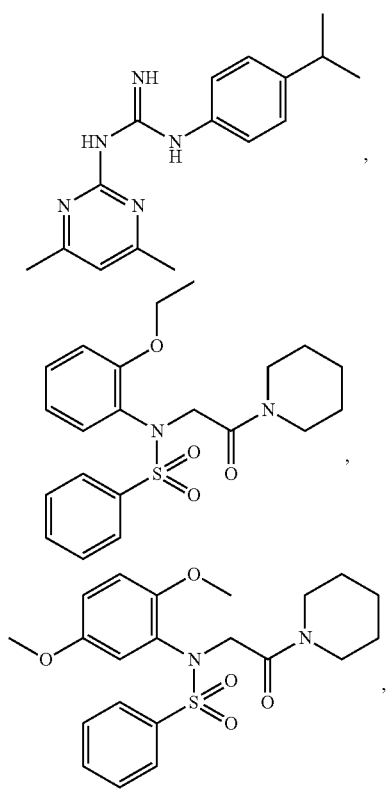

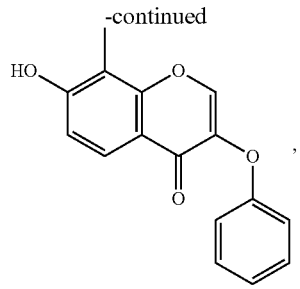

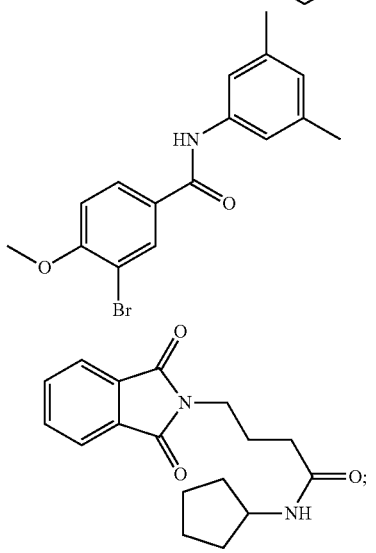

or wherein,
the CocE in the presence of the compound is more thermostable than the CocE in the absence of the compound and
the subject is diagnosed with, or at risk for, a cocaine-induced condition selected from the group consisting of cocaine overdose, cocaine toxicity, cocaine addiction, or cocaine dependence.

2. The method of claim 1, wherein the CocE polypeptide comprises
an amino acid sequence at least 90% identical to SEQ ID NO: 1 having esterase activity; or an amino acid sequence at least 90% identical to SEQ ID NO: 1 with one or more substitutions selected from the group consisting of L163V, V225I, I218L, A310D, A149S, S159A, S265A, S56G, W220A, S140A, F189L, A193D, T254R, N42V, V262L, L508G, Y152H, V160A, T172R, Y532F, T74S, W285T, L146P, D533S, A194R, G173Q, C477T, K531A, R41I, L119A, K46A, F84Y, T172R/G173Q, L169K, F189A, N197K, R182K, F189K, V190K, Q191K, A194K, and L169K/G173Q, or a combination thereof; and having esterase activity.

3. The method of claim 1, wherein the composition is administered by intravenous, intramuscular, subcutaneous, or intraperitoneal injection.

4. The method of claim 2, wherein the at least one thermostabilization compound is selected from:

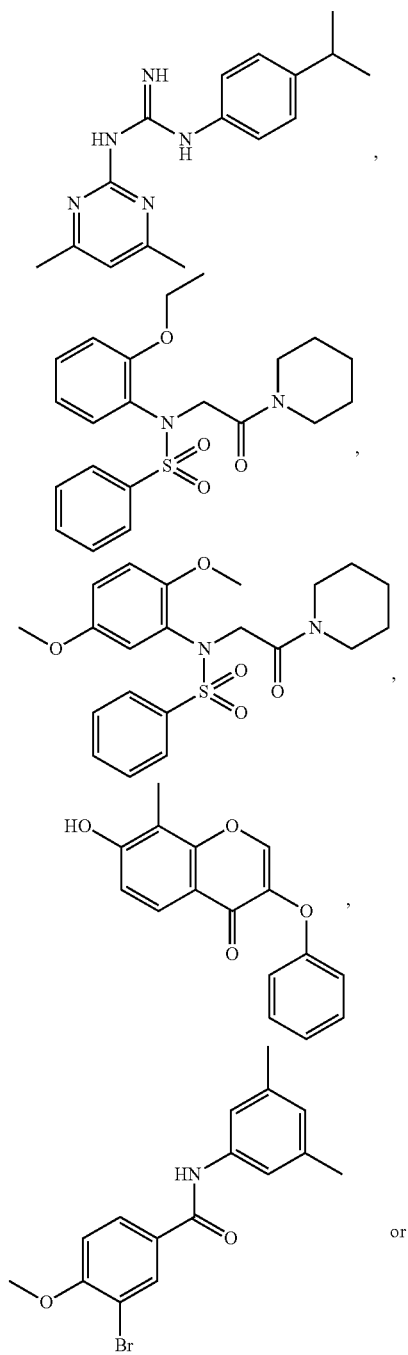

5. The method of claim 1, wherein the at least one thermostabilization compound is selected from:

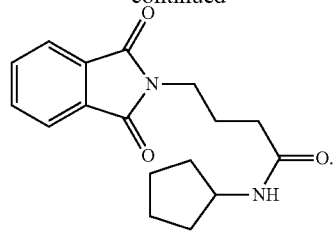

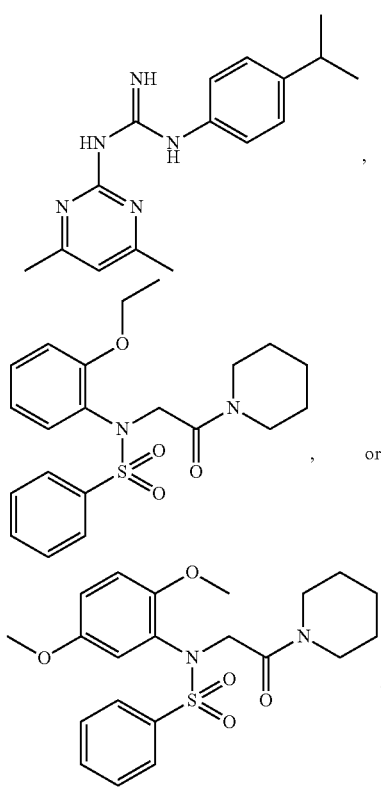

6. The method of claim 1, wherein the at least one thermostabilization compound is:

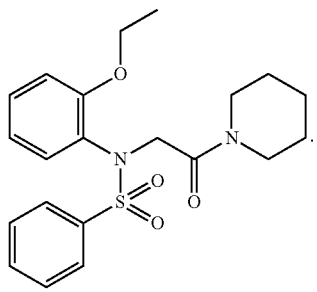

7. The method of claim 1, wherein the CocE polypeptide cocaine esterase comprises an amino acid sequence at least 90% identical to SEQ ID NO: 1 with one or more substitutions selected from the group consisting of L163V, V225I, I218L, A310D, A149S, S159A, S265A, S56G, W220A, S140A, F189L, A193D, T254R, N42V, V262L, L508G, Y152H, V160A, T172R, Y532F, T74S, W285T, L146P, D533S, A194R, G173Q, C477T, K531A, R41I, L119A, K46A, F84Y, T172R/G173Q, L169K, F189A, N197K, R182K, F189K, V190K, Q191K, A194K, and L169K/G173Q, or a combination thereof; and having esterase activity.

8. The method of claim 1, wherein the CocE polypeptide cocaine esterase comprises an amino acid sequence of SEQ ID NO: 1 with one or more substitutions selected from the group consisting of: T172R, S159A, N197K, L169K, F189K, G173Q, and T172R/G173Q.

9. The method of claim 1, wherein the CocE polypeptide comprises an amino acid sequence having at least 85% sequence identity with SEQ ID NO:1, having substitutions L169K/G173Q, esterase activity, and increased thermostability at 37 °C. as compared to wild-type CocE.

10. The method of claim 1, wherein the CocE polypeptide comprises an amino acid sequence of SEQ ID NO:1 with substitutions L169K/G173Q.

11. The method of claim 1, wherein the CocE polypeptide cocaine esterase comprises an amino acid sequence of SEQ ID NO: 1.

12. The method of claim 1, wherein the CocE polypeptide is a pegylated CocE polypeptide.

13. The method of claim 1, wherein the composition comprises a pharmaceutically acceptable carrier.

14. The method of claim 1, wherein the composition is administered by intravenous injection.

15. The method of claim 1, wherein the composition is administered via a mini-infusion pump.

16. The method of claim 1, wherein the mammalian subject is selected from the group consisting of a rodent, rabbit, guinea pig, horse, cow, dog, cat, sheep, pig, and human.

17. The method of claim 1, wherein the mammalian subject is a human.

* * * * *

```
SEQUENCE LISTING

<160> NUMBER OF SEQ ID NOS: 1

<210> SEQ ID NO 1
<211> LENGTH: 574
<212> TYPE: PRT
<213> ORGANISM: Rhodococcus sp.

<400> SEQUENCE: 1

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30
```

-continued

```
Gly Pro Val Pro Val Leu Leu Val Arg Asn Pro Tyr Asp Lys Phe Asp
             35                  40                  45

Val Phe Ala Trp Ser Thr Gln Ser Thr Asn Trp Leu Glu Phe Val Arg
 50                  55                  60

Asp Gly Tyr Ala Val Val Ile Gln Asp Thr Arg Gly Leu Phe Ala Ser
 65                  70                  75                  80

Glu Gly Glu Phe Val Pro His Val Asp Asp Glu Ala Asp Ala Glu Asp
                     85                  90                  95

Thr Leu Ser Trp Ile Leu Glu Gln Ala Trp Cys Asp Gly Asn Val Gly
                100                 105                 110

Met Phe Gly Val Ser Tyr Leu Gly Val Thr Gln Trp Gln Ala Ala Val
                115                 120                 125

Ser Gly Val Gly Gly Leu Lys Ala Ile Ala Pro Ser Met Ala Ser Ala
                130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
                180                 185                 190

Ala Ala Ile Leu Asn Asp Val Ala Gly Ala Ala Ser Val Thr Pro Leu
                195                 200                 205

Ala Glu Gln Pro Leu Leu Gly Arg Leu Ile Pro Trp Val Ile Asp Gln
                210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
                260                 265                 270

Lys Asp Asn Ala Asp Ala Arg Leu Val Val Gly Pro Trp Ser His Ser
                275                 280                 285

Asn Leu Thr Gly Arg Asn Ala Asp Arg Lys Phe Gly Ile Ala Ala Thr
                290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
                340                 345                 350

Leu Pro Asp Thr Ala Tyr Thr Pro Phe Tyr Leu Gly Ser Gly Ala
                355                 360                 365

Ala Asn Thr Ser Thr Gly Gly Gly Thr Leu Ser Thr Ser Ile Ser Gly
                370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
                420                 425                 430

Glu Val Leu Thr Asp Pro Val Glu Val Thr Gly Thr Val Ser Ala Arg
                435                 440                 445
```

-continued

| | | | | | | | | | | | | | | | |
|---|---|---|---|---|---|---|---|---|---|---|---|---|---|---|---|
| Leu | Phe 450 | Val | Ser | Ser | Ala 455 | Val | Asp | Thr | Asp 460 | Phe | Thr | Ala | Lys | Leu | |
| Val 465 | Asp | Val | Phe | Pro 470 | Asp | Gly | Arg | Ala | Ile 475 | Ala | Leu | Cys | Asp | Gly | Ile 480 |
| Val | Arg | Met | Arg | Tyr 485 | Arg | Glu | Thr | Leu | Val 490 | Asn | Pro | Thr | Leu | Ile 495 | Glu |
| Ala | Gly | Glu | Ile | Tyr 500 | Glu | Val | Ala | Ile 505 | Asp | Met | Leu | Ala | Thr 510 | Ser | Asn |
| Val | Phe | Leu 515 | Pro | Gly | His | Arg | Ile 520 | Met | Val | Gln | Val | Ser 525 | Ser | Ser | Asn |
| Phe | Pro 530 | Lys | Tyr | Asp | Arg | Asn 535 | Ser | Asn | Thr | Gly | Gly 540 | Val | Ile | Ala | Arg |
| Glu 545 | Gln | Leu | Glu | Glu | Met 550 | Cys | Thr | Ala | Val | Asn 555 | Arg | Ile | His | Arg | Gly 560 |
| Pro | Glu | His | Pro | Ser 565 | His | Ile | Val | Leu | Pro 570 | Ile | Ile | Lys | Arg | | |